(12) United States Patent
Costantino et al.

(10) Patent No.: US 8,445,239 B2
(45) Date of Patent: May 21, 2013

(54) FERMENTATION PROCESSES FOR CULTIVATING STREPTOCOCCI AND PURIFICATION PROCESSES FOR OBTAINING CPS THEREFROM

(75) Inventors: Paolo Costantino, Colle Val d'Elsa (IT); Francesco Norelli, Siena (IT); Francesco Berti, Colle Val d'Elsa (IT); Roberto Olivieri, Siena (IT); Giulia Bazzocchi, Vicenza (IT); Concetta Maria Cicala, Castellina Scalo (IT); Silvia Fontani, Siena (IT)

(73) Assignee: Novartis AG, Basel (CH)

( * ) Notice: Subject to any disclaimer, the term of this patent is extended or adjusted under 35 U.S.C. 154(b) by 316 days.

(21) Appl. No.: 12/747,914

(22) PCT Filed: Dec. 19, 2008

(86) PCT No.: PCT/IB2008/003729
§ 371 (c)(1),
(2), (4) Date: Jun. 13, 2010

(87) PCT Pub. No.: WO2009/081276
PCT Pub. Date: Jul. 2, 2009

(65) Prior Publication Data
US 2010/0272755 A1    Oct. 28, 2010

Related U.S. Application Data

(60) Provisional application No. 61/008,941, filed on Dec. 20, 2007.

(30) Foreign Application Priority Data

Oct. 8, 2008  (GB) .................................. 0818453.3

(51) Int. Cl.
*C12P 19/04*    (2006.01)
(52) U.S. Cl.
USPC ........................................................ 435/101
(58) Field of Classification Search
None
See application file for complete search history.

(56) References Cited

FOREIGN PATENT DOCUMENTS

| WO | 2004/033623 | 4/2004 |
|----|-------------|--------|
| WO | 2006/082527 | 8/2006 |
| WO | 2007/052168 | 5/2007 |

OTHER PUBLICATIONS

Paoletti et al., "Cell growth rate regulates expression of group b Streptococcus type III capsular polysaccharide," Infection and Immunity 64, 1220-26, Jan. 1, 1996.
International Search Report and Written Opinion for PCT/IB2008/003729, dated Jul. 20, 2009.

*Primary Examiner* — James Martinell
(74) *Attorney, Agent, or Firm* — Banner & Witcoff, Ltd.

(57) ABSTRACT

This invention is in the field of bacterial cultures and specifically relates to the optimization of culture conditions to improve the production of bacterial capsular polysaccharides from *Streptococcus* strains in fed batch culture and to novel purification methods suitable for production scale purification of bacterial capsular polysaccharides from *Streptococcus* strains resulting in higher levels of purity than previously obtained for production scale.

17 Claims, 35 Drawing Sheets

FIGURE 3A
Type Ia (090)
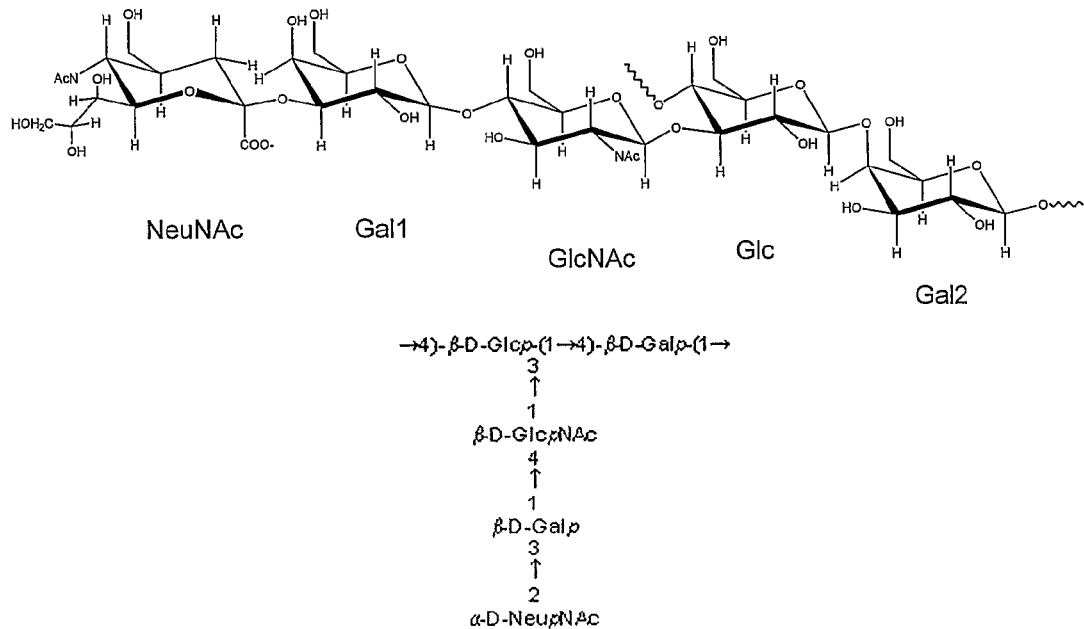
Type Ib (H36b)
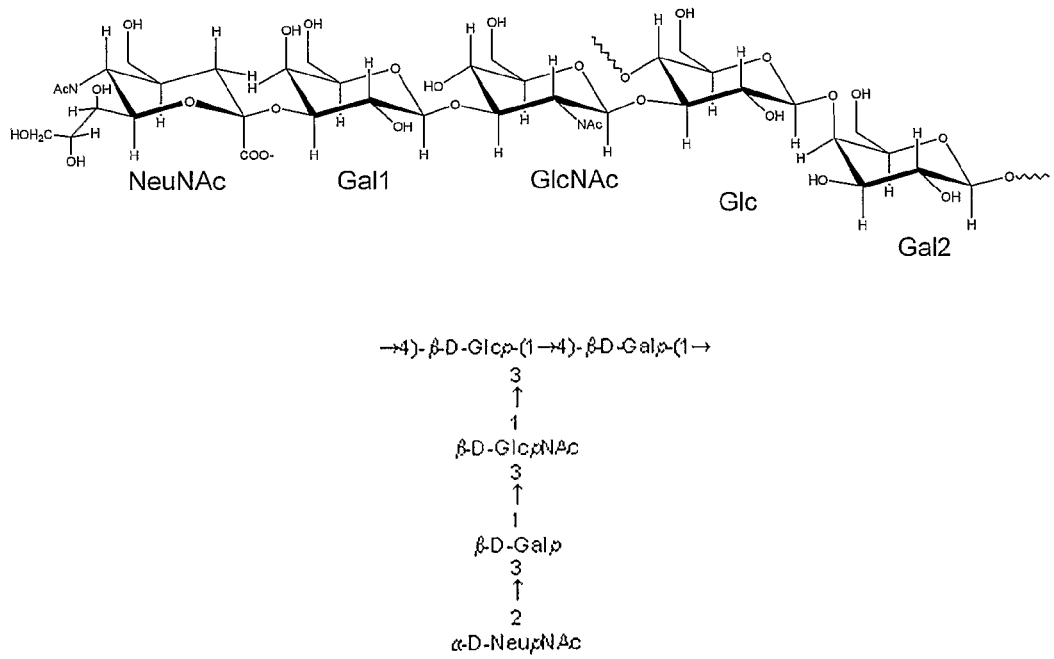

FIGURE 3B
Type III (M781)
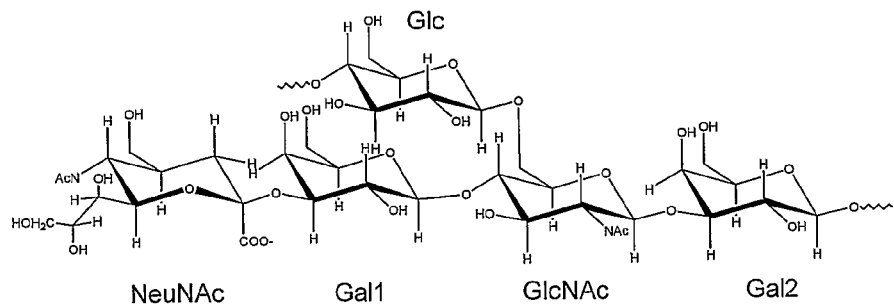
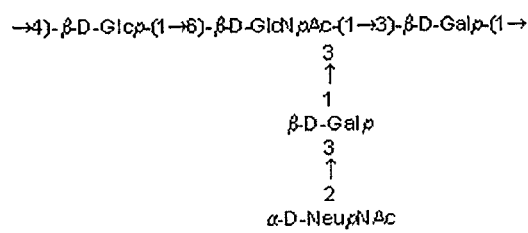
Type V (CJB111)
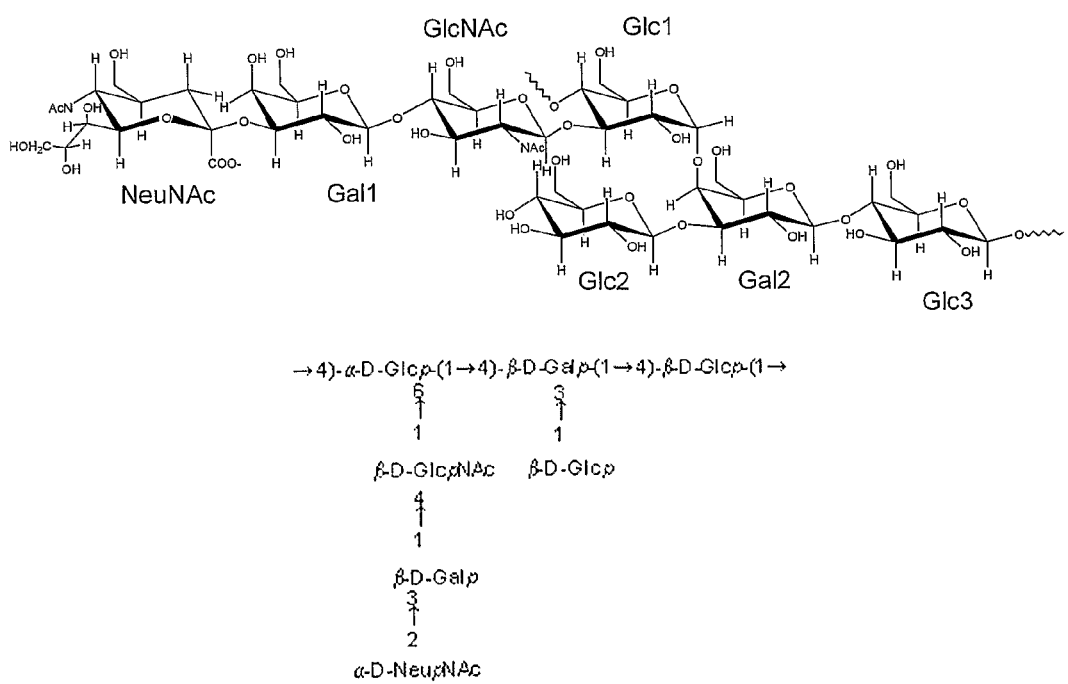

Growth curve and pH of medium for the M781 strain (μ was calculated with OD values in a range 0.1-2.4)

Growth curve and pH of medium for the CJB111 strain (μ was calculated with OD values in a range 0.1-2.4)

(A) 090 Growth curve

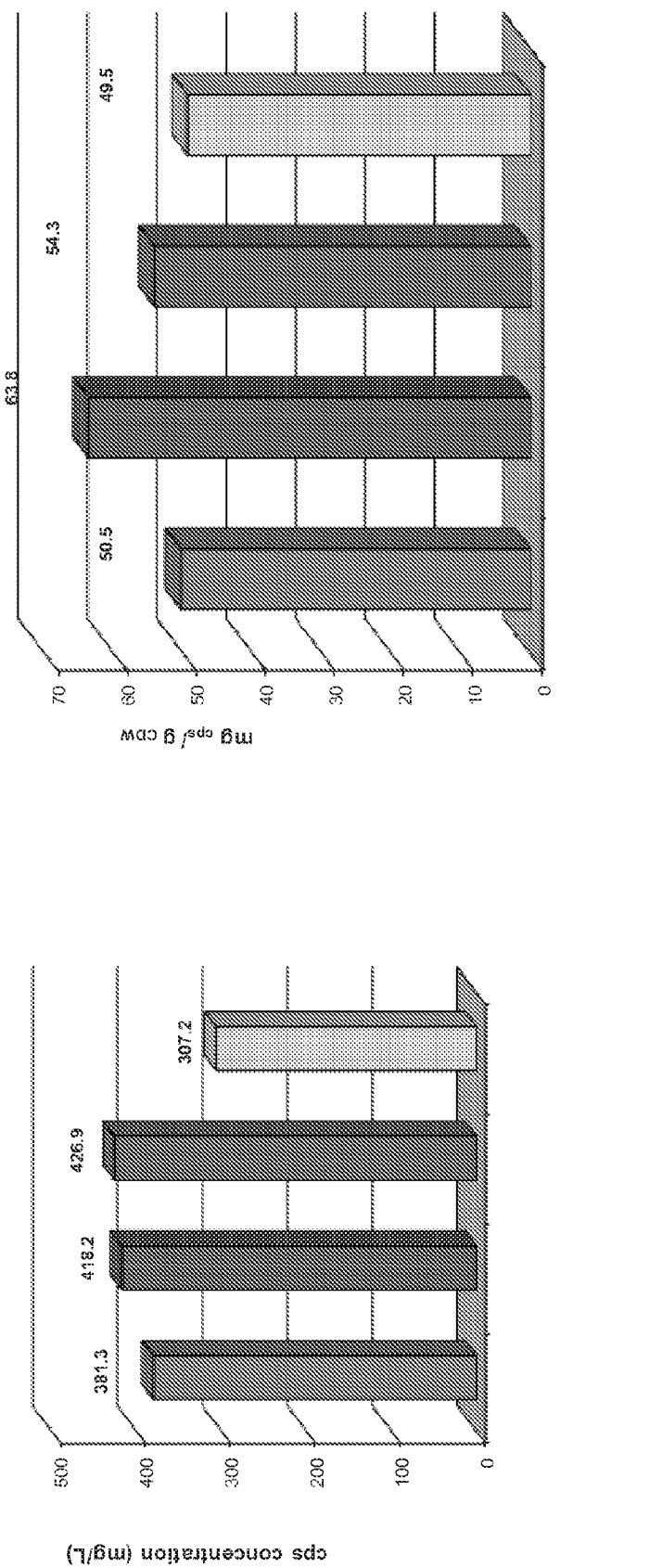
FIGURE 6, cont.
(B) Cps concentration by 090 strain
(C) Cps production by gram CDW for 090 strain

FIGURE 7
H36b Strain:
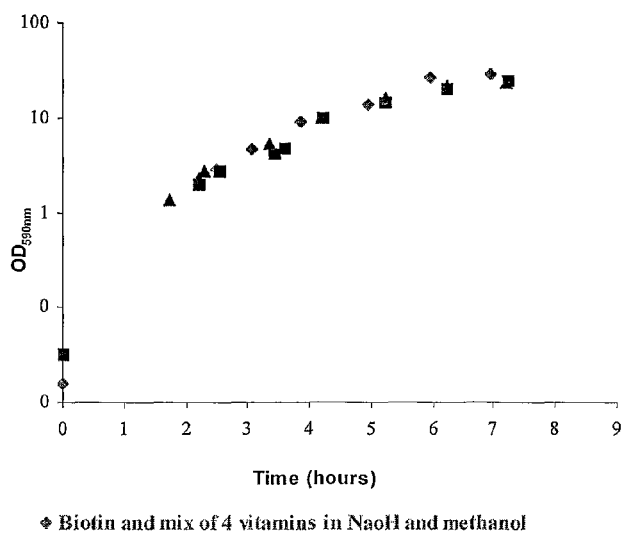
(A) H36b growth curve
♦ Biotin and mix of 4 vitamins in NaoH and methanol
■ Biotin and mix of 3 vitamins in water (without riboflavin)
▲ Only biotin
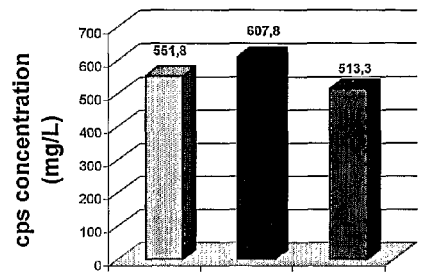
(B) Cps concentration by H36b strain
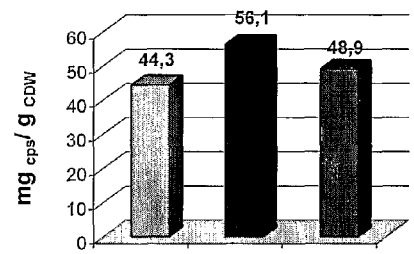
(C) Cps production by gram CDW for H36B

FIGURE 8
M781 Strain:
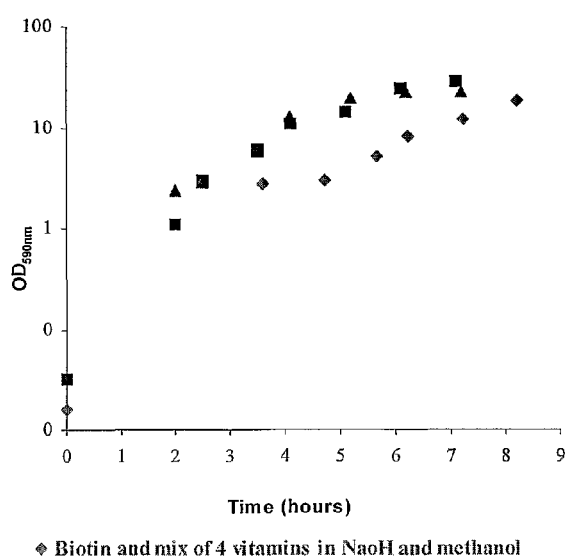
(A) M781 growth curve
♦ Biotin and mix of 4 vitamins in NaoH and methanol
■ Biotin and mix of 3 vitamins in water (without riboflavin)
▲ Only biotin
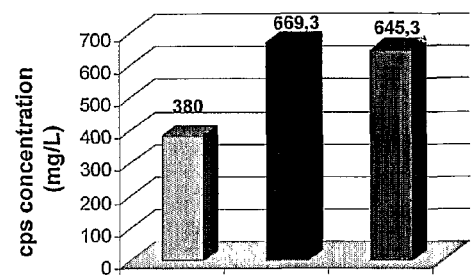
(B) Cps concentration by M781 strain
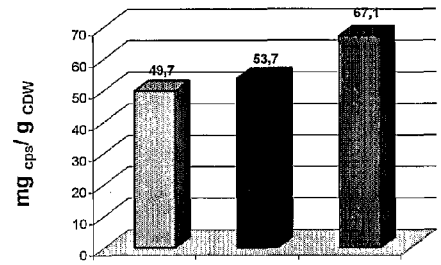
(C) Cps production by gram CDW for M781 strain Cps production by CJB111 and
Cps production by gram CDW for CJB111 strain

FIGURE 10
090 Strain:
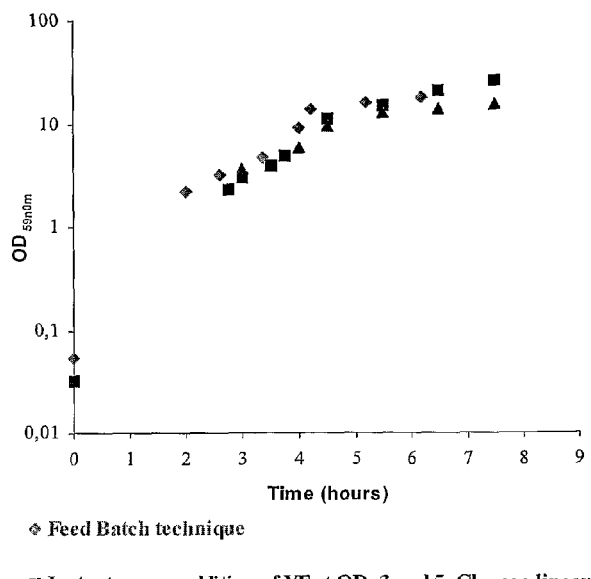
(A) 090 Growth curve
◆ Feed Batch technique
■ Instantaneous addition of YE at OD=3 and 5, Glucose linear
▲ All Yeast axtract in batch medium, Glucose linear
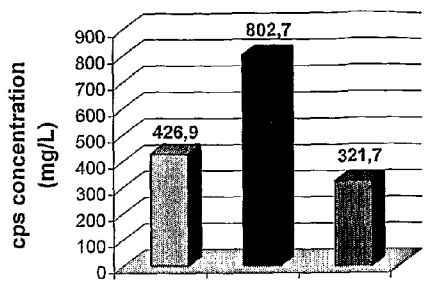
(B) Cps concentration by 090 strain
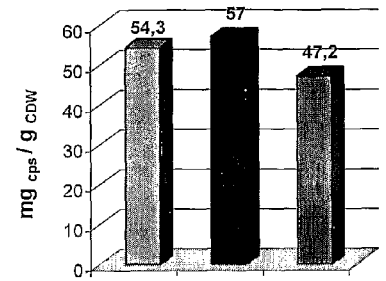
(C) Cps production by gram CDW for 090 strain

FIGURE 11
H36b Strain:
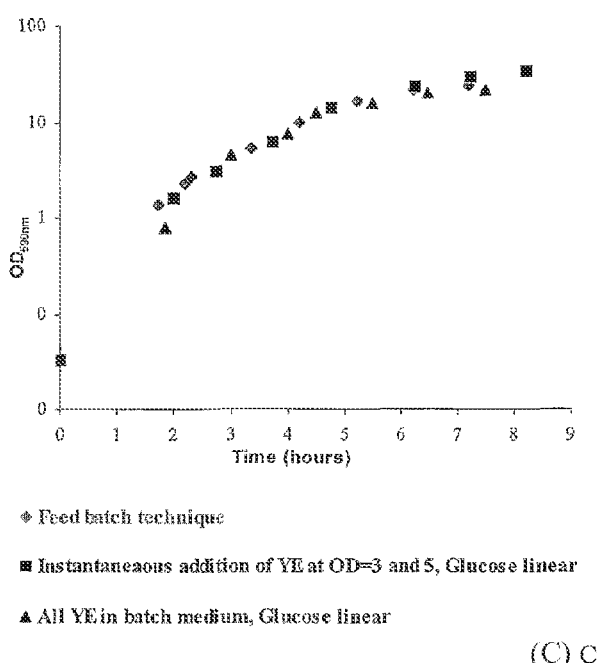
♦ Feed batch technique
■ Instantaneous addition of YE at OD=3 and 5, Glucose linear
▲ All YE in batch medium, Glucose linear
(A) H36b growth curve
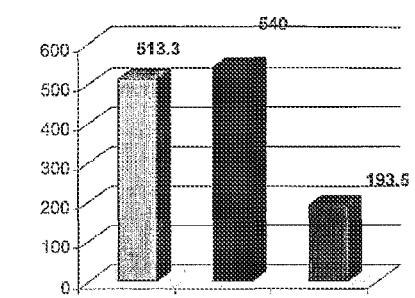
(B) Cps concentration by H36b strain
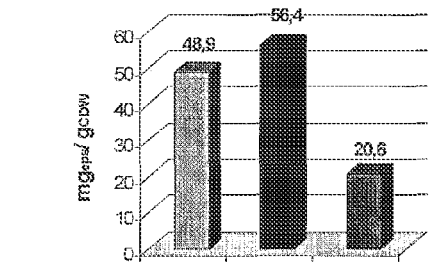
(C) Cps production by gram CDW for H36b

FIGURE 12
M781 Strain:
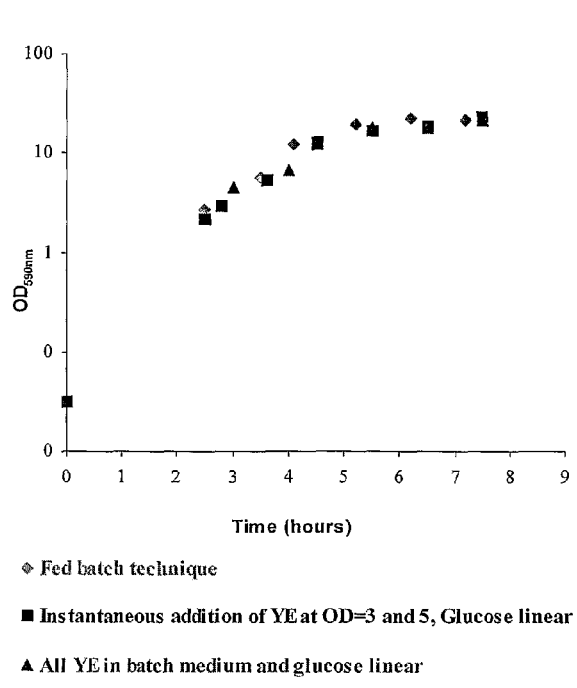
◆ Fed batch technique
■ Instantaneous addition of YE at OD=3 and 5, Glucose linear
▲ All YE in batch medium and glucose linear
(A) M781 growth curve
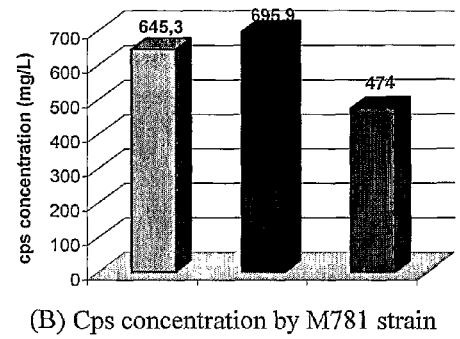
(B) Cps concentration by M781 strain
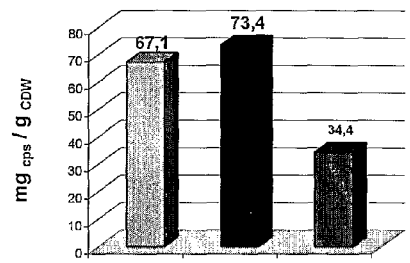
(C) Cps production by gram CDW for M781 strain

| mg/L | 550 |
|---|---|
| $mg_{cps}/g_{cdw}$ | 57,8 |

Cps production by CJB111 and
Cps production by gram CDW for CJB111 strain

FIGURE 14
DOT study:
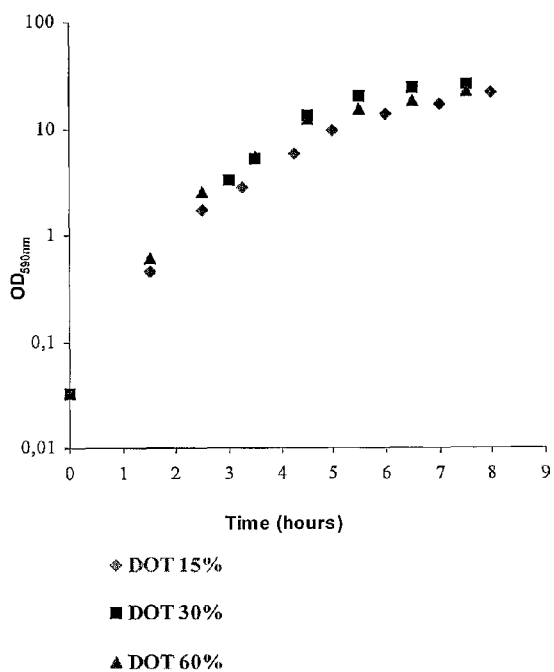
(A) H36b growth curve
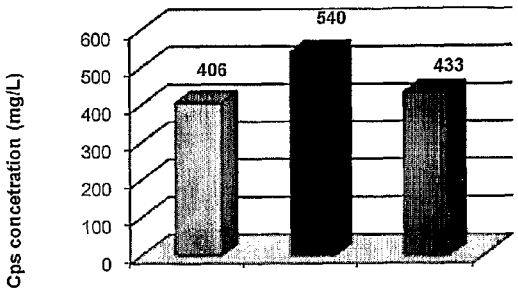
(B) Cps concentration by H36b strain
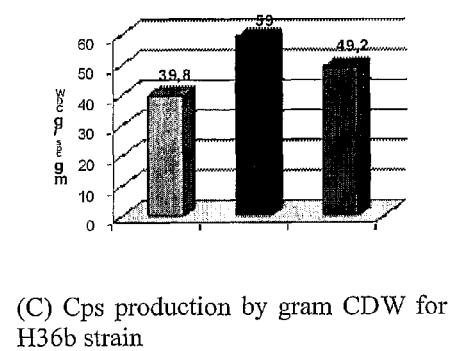
(C) Cps production by gram CDW for H36b strain
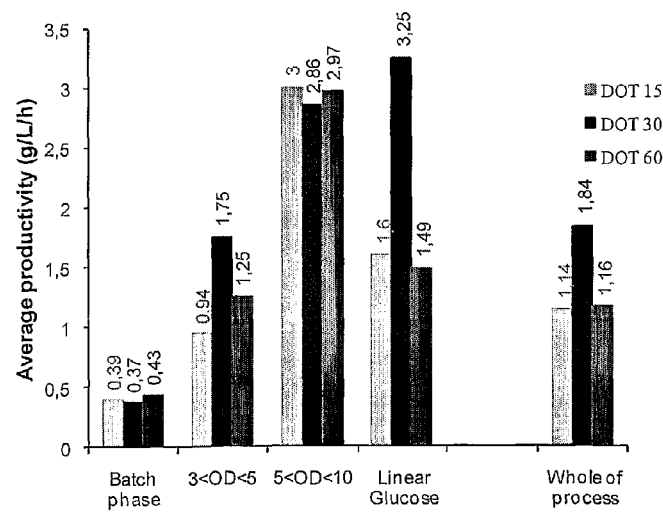
(D) Average productivity of H36b strain

FIGURE 15
Temperature study:
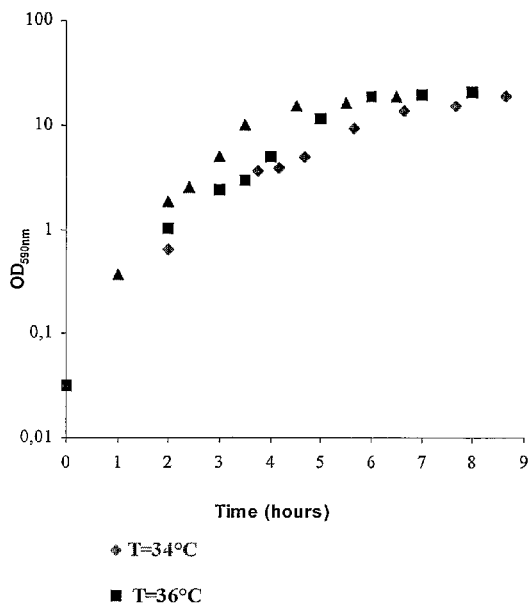
(A) H36b growth curve
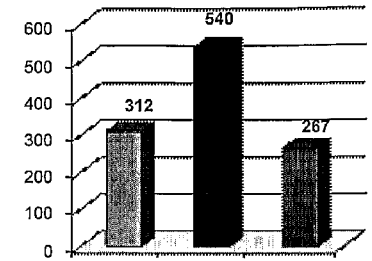
(B) Cps concentration by H36b strain
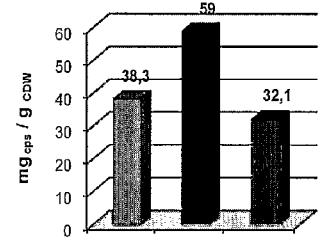
(C) Cps production by gram CDW for H36b strain
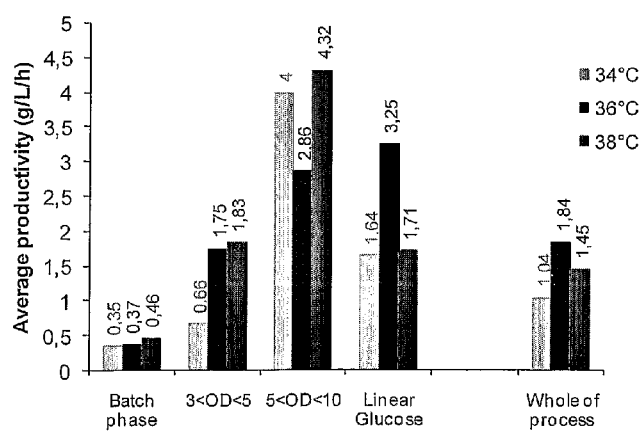
(D) Average productivity of H36b strain

FIGURE 16
pH study:
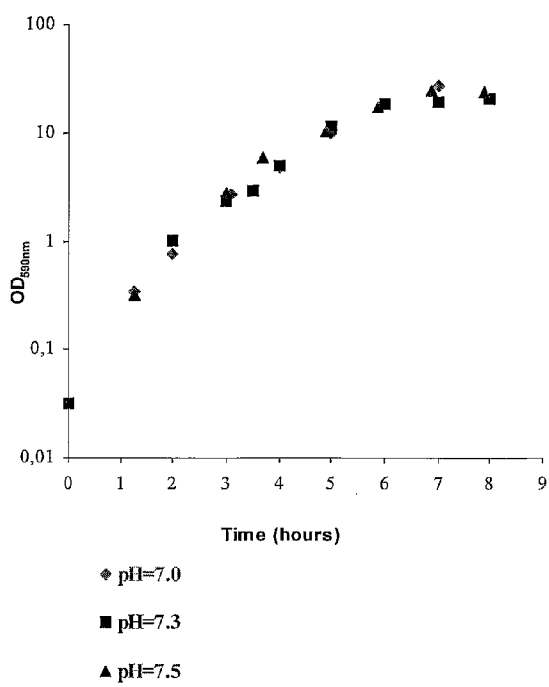
(A) H36b growth curve
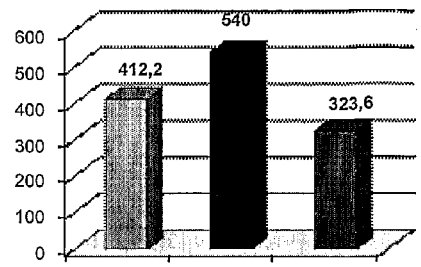
(B) Cps concentration by H36b strain
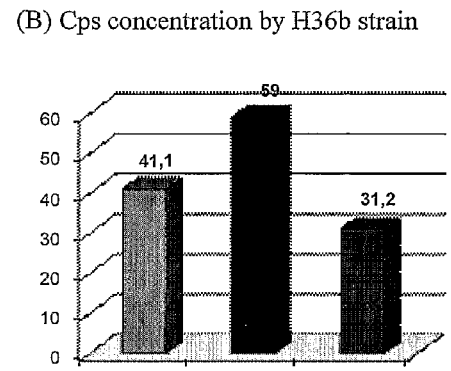
(C) Cps production by gram CDW for H36b strain
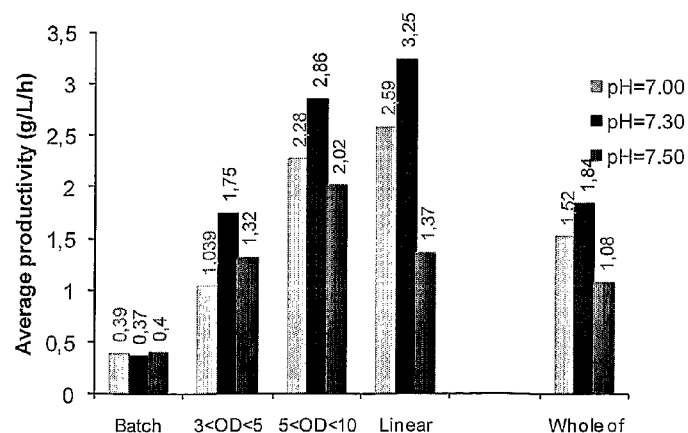
(D) Average productivity of H36b strain FIGURE 17
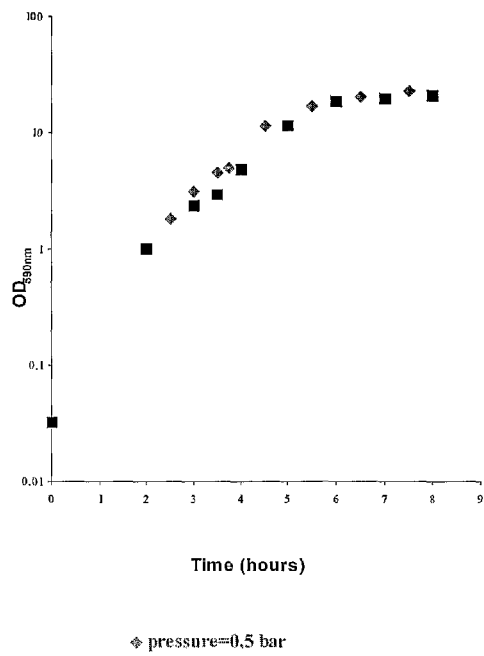
(A) H36b growth curve
◆ pressure=0,5 bar
■ pressure=0,2 bar
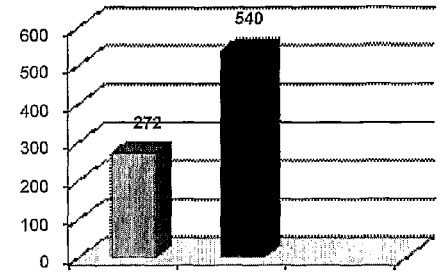
(B) Cps concentration by H36b strain
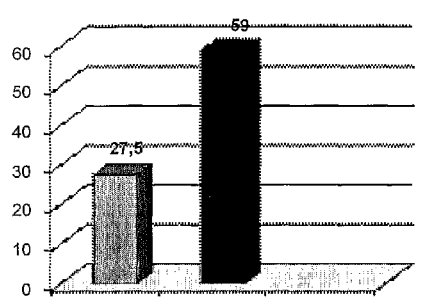
(C) Cps production by gram CDW for H36b strain
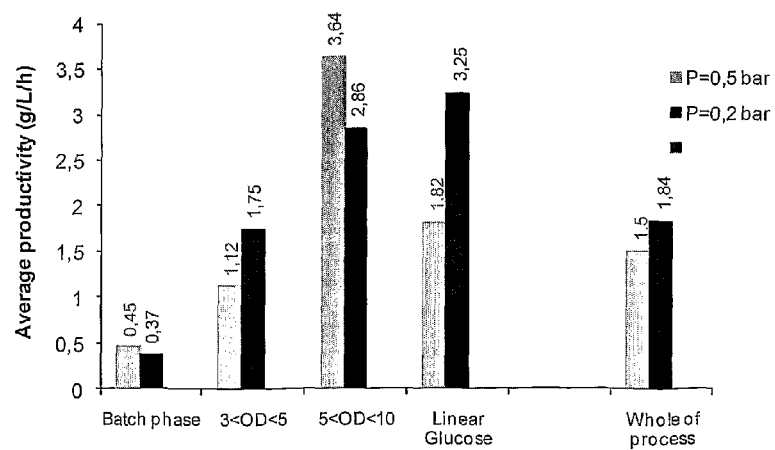
(D) Average productivity of H36b strain

FIGURE 18
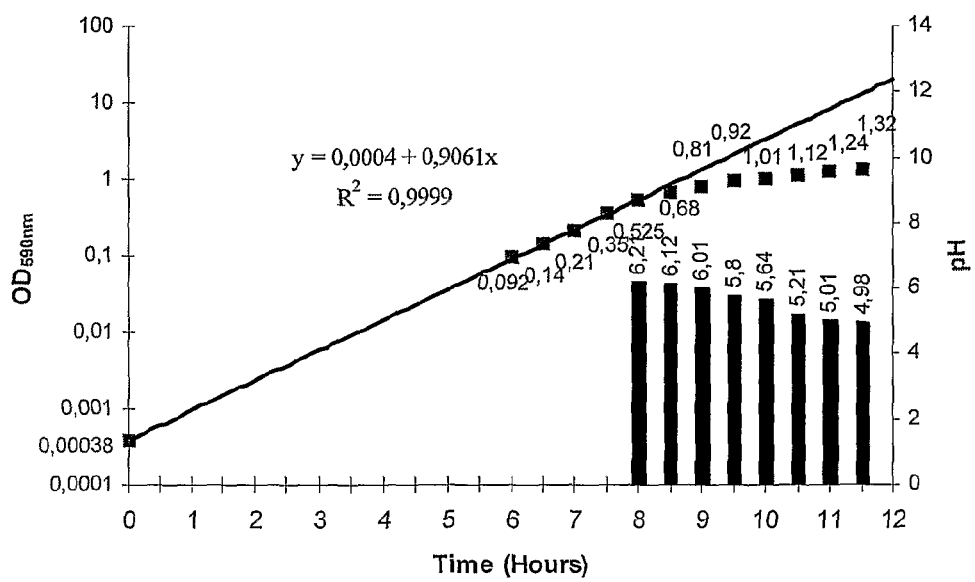
(A) M781Growth curve (0.1mL of w.s.) in a 500mL Erlenmeyer flasks containing 100mL of CDM
(µ was calculated with OD values in a range 0.1-0.7)
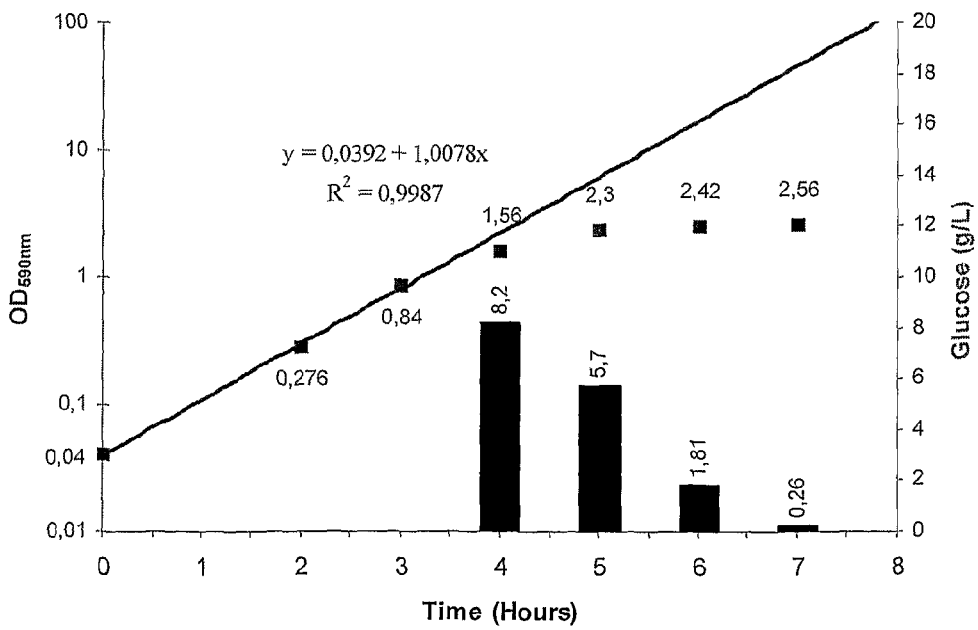
(B) M781Growth curve in a 2 liters fermentor
(µ was calculated with OD values in a range 0.1-1)

Growth curve and glucose consumption of M781strain

Effect of omission of alanine, aspartic acid, glutamine and proline on growth of strain M781 of GBS in a CDM $OD_{590nm}$ profiles of the first pre test runs fermentations OD 590nm profiles of the second pre test runs fermentations OD 590nm profiles of the test runs fermentations

FERMENTATION PROCESSES FOR CULTIVATING STREPTOCOCCI AND PURIFICATION PROCESSES FOR OBTAINING CPS THEREFROM

This application claims the benefit of U.S. Provisional Application Ser. No. 61/008,941, filed on 20 Dec. 2007; and UK Application No. 0818453.3, filed on 8 Oct. 2008, both of which are incorporated by reference herein in their entirety.

FIELD OF THE INVENTION

This invention is in the field of bacterial cultures, and preferably relates to the optimization of culture conditions and novel purification methods to improve the production of bacterial capsular polysaccharides.

BACKGROUND OF THE INVENTION

Capsular polysaccharides (cps) are important immunogens found on the surface of bacteria involved in various bacterial diseases. This feature has led to them being an important component in the design of vaccines. They have proved useful in eliciting immune responses especially when linked to carrier proteins (Ref. 1).

Typically, capsular polysaccharides are produced using batch culture in complex medium (Group B *Streptococcus*, *Staphylococcus aureus*, *Streptococcus pneumoniae* and *Haemophilus influenzae*), fed batch culture (*H. influenzae*) or continuous culture (Group B *Streptococcus* and *Lactobacillus rhamnosus*) (Refs. 2-7). Most studies used batch culture systems in which the growth rate, nutrient levels and metabolic concentrations change during incubation. In such systems, alteration of one factor results in changes in other factors associated with growth that can affect yields unpredictably. Continuous cultures allow the researcher to separate and define parameters that are interdependent during batch culture growth, such as growth rate, nutrient and product concentrations and cell density. During continuous culture, fresh medium is added to a culture at a fixed rate and cells and medium are removed at a rate that maintains a constant culture volume. Continuous culture was preferred for capsular polysaccharide production when it proved to be dependent on conditions (Ref. 8).

For Group B *Streptococcus* (GBS, *S. agalactiae*), cell growth rate was reported to be the principal factor regulating capsular polysaccharide production. Furthermore, the production of type III capsular polysaccharide was shown to occur independently of the growth-limiting nutrient. Higher specific yields (up to about 90 mg/$g_{CDW}$) were obtained when cells were held at a fast (0.8, 1.4 or 1.6 h) mass doubling time ($t_d$) rather than at a slow time ($t_d$=2.6 or 11 h) (Refs. 8-10). However, continuous culture is prone to strain stability problems and contamination, and is somewhat expensive due to the continuous feed of medium and nutrients. Therefore, there is a need to find alternatives to continuous culture for the high yield production of capsular polysaccharides in order to overcome the problems with continuous culture that are cited above.

One approach to overcome the drawbacks of continuous culture is exemplified in WO 2007/052168. A complex fed batch fermentation process has been developed to maintain a nutritional environment and a growth rate favorable to cps production. This process combines the advantages of batch and continuous techniques, producing high cell densities due to extension of the exponential growth phase and to conditions that control substrate addition during fermentation. However, the complex fed batch technique uses software with a complex algorithm to manage the fermentation. Furthermore, a robust and cost-effective production process in compliance with Good Manufacturing Practices is necessary to generate material to support clinical trials. Therefore, there is an urgent need to simplify the fed batch fermentation process for large-scale production.

In addition to a need for simplified fermentation protocols, there is a need for simplified purification protocols that can be used in the large-scale production of capsular polysaccharides post-fermentation. The approach exemplified in WO 2007/052168 is based on the method disclosed in WO 2006/082527, which includes extraction, alcoholic precipitation, diafiltration, cationic detergent treatment, and re-solubilization. This procedure is highly efficient and typically yields a preparation of capsular polysaccharide that is approximately 80% pure. However, the step of cationic detergent treatment results in precipitation of the capsular polysaccharide. The subsequent separation of the precipitate from the supernatant (e.g. by centrifugation) and re-solubilization is laborious and may result in loss of capsular polysaccharide, thereby reducing yield. The efficiency of the cationic detergent treatment may also be dependent on the initial purity of the capsular polysaccharide. The lower the initial purity of the capsular polysaccharide, the less efficient the cationic detergent treatment may be, further limiting yield. Therefore, there is a need for a simplified purification procedure that will produce higher levels of purity with fewer complicated and/or expensive purification steps. There is also a need for a purification procedure that provides a good yield of capsular polysaccharide whatever the initial purity of the polysaccharide.

SUMMARY OF THE DISCLOSED EMBODIMENTS

The inventors have met the need for simplified fermentation protocols by providing methods for producing capsular polysaccharides (cps) from *Streptococcus* on a manufacturing scale. In certain embodiments, the algorithm for pH balancing during linear addition of a carbon source had been eliminated, and in other embodiments, unnecessary components of the media have been omitted. The preferred species of *Streptococcus* is *Streptococcus agalactiae*, also referred to as Lancefield's Group B *Streptococcus* or GBS, in particular, strains 090, H36b, CBJ111, or M781.

One aspect provides an inoculum of a strain of *Streptococcus* that expresses cps. In one embodiment, the optical density (OD) of the inoculum is preferably between 0.6-1.8, which is the mid-exponential phase of the inoculum. Although the reported OD values are measured at 590 nm, OD can be converted based on the absorbance wavelength of a given experiment.

Another aspect provides a method for cultivating the *Streptococcus* strain by fermentation. In one embodiment, the pH of the cultivating medium during the cultivating is between 6.0-7.5, preferably about 7.3. In another embodiment, the temperature of the cultivating medium during the cultivating is between 34-38° C., preferably about 36° C.

Another aspect provides a method for cultivating the *Streptococcus* strain, wherein the cultivating comprises two instantaneous additions of yeast extract, followed by a linear addition of a carbon source. The preferred carbon source for the linear addition is glucose. Each addition is initiated at a designated OD level, which has been selected to achieve a higher volumetric production of cps by regulating the bacteria growth rate and to adapt the micro-organism to produce a maximum serotype specific cps.

In one embodiment, the first instantaneous addition of yeast extract is initiated at an OD level between 2.8-3.2, preferably about 3.0. In another embodiment, the second instantaneous addition of yeast extract is initiated at an OD level between 4.3-4.7, preferably about 4.5. In another embodiment, the linear addition of the carbon source is initiated at an OD level between 9.8-10.0, preferably about 10.

Overall, the linear addition of a carbon source without an algorithm is an improvement over the previous complex fed batch fermentation process that used an algorithm to control the cultivating by monitoring a pH of the cultivating medium.

Another aspect provides a cultivating medium that includes a defined medium or a complex medium. The defined medium comprises a phosphate source, a mineral source, a carbon source, a vitamin source, and an amino acid source to grow *Streptococcus*. The vitamin source consists of six or fewer vitamins selected from the following list of seven vitamins: biotin, niacinamide, calcium pantothenate, riboflavin, thiamine hydrochloride, pyridoxine hydrochloride and folic acid, wherein two of the vitamins have to be calcium pantothenate and niacinamide.

The complex medium comprises a complex extract (preferably yeast extract), a phosphate source, a carbon source, a vitamin source, and optionally an amino acid source to grow *Streptococcus*. The vitamin source consists of four or fewer vitamins selected from the following list of five vitamins: biotin, niacinamide, riboflavin, thiamine hydrochloride and pyridoxine hydrochloride, wherein one of the vitamins has to be biotin (i.e., four of the five are included in the medium while the fifth is not added other that as a natural component of the complex extract). In preferred embodiment, the vitamin source has three or fewer, two or fewer, or biotin only.

The invention further provides a composition including a cultivating medium that is a defined medium, which is comprised of a phosphate source, a mineral source, a carbon source, a vitamin source, and an amino acid source to grow *Streptococcus*. Once again, the preferred strain of *Streptococcus* is *Streptococcus agalactiae*, in particular, strain 090, H36b, CBJ111, or M781. In one embodiment, the phosphate source consists of $K_2HPO_4$, $KH_2PO_4$, $Na_2HPO_4.H_2O$, $NaH_2PO_4.H_2O$, or $NaCl$. In one embodiment, the preferred carbon source is glucose.

In another embodiment, the vitamin source consists of six or fewer vitamins selected from the following list of seven vitamins: biotin, niacinamide, calcium pantothenate, riboflavin, thiamine hydrochloride, pyridoxine hydrochloride and folic acid, wherein two of the vitamins have to be calcium pantothenate and niacinamide.

In another embodiment, the vitamin source consists of five or fewer from the following list of seven vitamins: biotin, niacinamide, calcium pantothenate, riboflavin, thiamine hydrochloride, pyridoxine hydrochloride, and folic acid, wherein two have to be calcium pantothenate and niacinamide.

In another embodiment, the vitamin source consists of four or fewer from the following list of seven vitamins: biotin, niacinamide, calcium pantothenate, riboflavin, thiamine hydrochloride, pyridoxine hydrochloride, and folic acid, wherein two have to be calcium pantothenate and niacinamide.

In another embodiment, the vitamin source consists of three or fewer from the following list of seven vitamins: biotin, niacinamide, calcium pantothenate, riboflavin, thiamine hydrochloride, pyridoxine hydrochloride, and folic acid, wherein two have to be calcium pantothenate and niacinamide.

In another embodiment, the vitamin source consists of calcium pantothenate and niacinamide.

In another embodiment, the amino acid source consists of nineteen or fewer from the following list of nineteen amino acids: alanine, arginine, glutamine, glycine, histidine, isoleucine, leucine, lysine, methionine, phenylalanine, proline, serine, threonine, tryptophan, valine, aspartic acid, cysteine hydrochloride, glutamic acid, and tyrosine, wherein fifteen have to be arginine, glycine, histidine, isoleucine, leucine, lysine, methionine, phenylalanine, serine, threonine, tryptophan, valine, cysteine hydrochloride, glutamic acid, and tyrosine.

In another embodiment, the amino acid source consists of eighteen or fewer from the following list of nineteen amino acids: alanine, arginine, glutamine, glycine, histidine, isoleucine, leucine, lysine, methionine, phenylalanine, proline, serine, threonine, tryptophan, valine, aspartic acid, cysteine hydrochloride, glutamic acid, and tyrosine, wherein fifteen have to be arginine, glycine, histidine, isoleucine, leucine, lysine, methionine, phenylalanine, serine, threonine, tryptophan, valine, cysteine hydrochloride, glutamic acid, and tyrosine.

In another embodiment, the amino acid source consists of seventeen or fewer from the following list of nineteen amino acids: alanine, arginine, glutamine, glycine, histidine, isoleucine, leucine, lysine, methionine, phenylalanine, proline, serine, threonine, tryptophan, valine, aspartic acid, cysteine hydrochloride, glutamic acid, and tyrosine, wherein fifteen have to be arginine, glycine, histidine, isoleucine, leucine, lysine, methionine, phenylalanine, serine, threonine, tryptophan, valine, cysteine hydrochloride, glutamic acid, and tyrosine.

In another embodiment, the amino acid source consists of sixteen or fewer from the following list of nineteen amino acids: alanine, arginine, glutamine, glycine, histidine, isoleucine, leucine, lysine, methionine, phenylalanine, proline, serine, threonine, tryptophan, valine, aspartic acid, cysteine hydrochloride, glutamic acid, and tyrosine, wherein fifteen have to be arginine, glycine, histidine, isoleucine, leucine, lysine, methionine, phenylalanine, serine, threonine, tryptophan, valine, cysteine hydrochloride, glutamic acid, and tyrosine.

In another embodiment, the amino acid source consists of arginine, glycine, histidine, isoleucine, leucine, lysine, methionine, phenylalanine, serine, threonine, tryptophan, valine, cysteine hydrochloride, glutamic acid, and tyrosine.

Another aspect provides a composition including a cultivating medium that is a complex medium, which is comprised of a complex extract (preferably a yeast extract), a phosphate source, a carbon source, a vitamin source, and optionally an amino acid source to grow *Streptococcus*. Once again, the preferred strain of *Streptococcus* is *Streptococcus agalactiae*, in particular, strain 090, H36b, CBJ111, or M781.

In one embodiment, the vitamin source consists of four or fewer vitamins selected from the following list of five vitamins: biotin, niacinamide, riboflavin, thiamine hydrochloride and pyridoxine hydrochloride, wherein one of the vitamins has to be biotin.

In another embodiment, the vitamin source consists of three or fewer vitamins selected from the following list of five vitamins: biotin, niacinamide, riboflavin, thiamine hydrochloride and pyridoxine hydrochloride, wherein one of the vitamins has to be biotin.

In another embodiment, the vitamin source consists of two or fewer vitamins selected from the following list of five vitamins: biotin, niacinamide, riboflavin, thiamine hydrochloride and pyridoxine hydrochloride, wherein one of the vitamins has to be biotin.

In another embodiment, the vitamin source is biotin.

The foregoing aspects and embodiments are not intended to be exclusive of one another and may be combined with each other and any other aspects or embodiments disclose in this specification except to the extend mutually exclusive.

The invention further provides a method for purifying a capsular polysaccharide, typically from *Streptococcus agalactiae*, comprising a step of filtration using an adherent filter. The adherent filter is one that binds contaminants that may be present in the capsular polysaccharide, e.g. proteins and/or nucleic acids, while allowing the capsular polysaccharide to pass through the filter. The inventors have found that adherent filters can be used to purify capsular polysaccharides instead of the cationic detergent treatment described in WO 2007/052168 and WO 2006/082527. The use of an adherent filter removes the need to apply a cationic detergent, which means that there is no precipitation of the capsular polysaccharide at this stage of the method. This in turn removes the need to separate the precipitate from the supernatant, simplifying the method and preventing any loss of the capsular polysaccharide that may occur during this separation. The use of an adherent filter can therefore improve the yield of the purification method. The efficiency of the adherent filter is also less dependent on the initial purity of the capsular polysaccharide.

The skilled person is capable of identifying suitable adherent filters for use in this method. Typically, the main contaminant in the capsular polysaccharide is protein, and the adherent filter is therefore a protein adherent filter. The inventors have found that carbon filters are particularly suitable. They typically comprise activated carbon (e.g. as a granular carbon bed or as a pressed or extruded carbon block), which acts as the filter for purification of the sample.

The skilled person is capable of identifying suitable carbon filters. Typically, a carbon filter for use in the present invention contains activated carbon immobilized in a matrix. The matrix may be any porous filter medium permeable for the sample. The matrix may comprise a support material and/or a binder material. The support material may be a synthetic polymer or a polymer of natural origin. Suitable synthetic polymers may include polystyrene, polyacrylamide and polymethyl methacrylate, while polymers of natural origin may include cellulose, polysaccharide and dextran, agarose. Typically, the polymer support material is in the form of a fibre network to provide mechanical rigidity. The binder material may be a resin. The matrix may have the form of a membrane sheet. Typically, the activated carbon immobilized in the matrix may be in the form of a cartridge. A cartridge is a self-contained entity containing powdered activated carbon immobilized in the matrix and prepared in the form of a membrane sheet. The membrane sheet may be captured in a plastic permeable support to form a disc. Alternatively, the membrane sheet may be spirally wound. To increase filter surface area, several discs may be stacked upon each other. In particular, the discs stacked upon each other have a central core pipe for collecting and removing the carbon-treated sample from the filter. The configuration of stacked discs may be lenticular. The activated carbon in the carbon filter may be derived from different raw materials, e.g. peat, lignite, wood or coconut shell. Any process known in the art, such as steam or chemical treatment, may be used to activate carbon. In the present invention, activated carbon immobilized in a matrix may be placed in a housing to form an independent filter unit. Each filter unit has its own in-let and out-let for the sample to be purified. Examples of filter units that are usable in the present invention are the carbon cartridges from Cuno Inc. (Meriden, USA) or Pall Corporation (East Hill, USA).

In particular, the inventors have found that CUNO Zetacarbon™ filters are suitable for use in the invention. These carbon filters comprise a cellulose matrix into which activated carbon powder is entrapped and resin-bonded in place.

The starting material for the method of this aspect of the invention may be one of the starting materials described in the section entitled "Starting material" below. The method may additionally comprise one or more of the steps described in the sections entitled "Alcoholic precipitation and cation exchange", "Diafiltration", "Re—N-acetylation", "Further diafiltration", "Conjugate preparation" and/or "Other steps" below. A typical sequence of steps would therefore be i) a step or steps described in the section entitled "Alcoholic precipitation and cation exchange"; ii) a step or steps described in the section "Diafiltration"; iii) a step of filtration using an adherent filter, as described above; iv) a step or steps described in the section entitled "Re—N-acetylation"; and v) a step or steps described in the section entitled "Further diafiltration". This process may then be followed by a step or steps described in the section entitled "Conjugate preparation". Finally, this process may be followed by a step or steps described in the section entitled "Other steps".

The method may additionally comprise one or more of the steps described in the sections entitled "Cationic detergent treatment" and "Re-solubilization" below, although typically these steps are omitted because cationic detergent treatment to precipitate the capsular polysaccharide and subsequent re-solubilization of the polysaccharide is generally not required when filtration is carried out using an adherent filter in the method of the invention. Accordingly, the invention specifically envisages a method for purifying a capsular polysaccharide, typically from *Streptococcus agalactiae*, comprising a step of filtration using an adherent filter, wherein the method does not include a step of cationic detergent treatment to precipitate the capsular polysaccharide followed by a step of re-solubilization of the capsular polysaccharide.

The invention further provides methods for purifying capsular polysaccharides (cps) from *Streptococcus* also on a manufacturing scale. The preferred species of *Streptococcus* is *Streptococcus agalactiae*, also referred to as Lancefield's Group B *Streptococcus* or GBS, in particular, strains 090, H36b, CBJ111, or M781.

In a preferred embodiment the method for production of a purified capsular polysaccharide includes one or more of the following steps: (a) providing a crude isolate containing a capsular polysaccharide; (b) removing an alcohol precipitate formed by contacting the crude isolate with an alcohol solution; (c) filtering to remove smaller molecular weight compounds while retaining the capsular polysaccharide; and (d) removing protein contaminants with a protein adherent filter to produce the purified capsular polysaccharide. In a preferred embodiment, the method includes all of the foregoing steps. In a more preferred embodiment, the method omits detergent precipitation.

In certain embodiments, one or more additional steps may be performed including (e) re-N-acetylating the purified capsular polysaccharide, (f) precipitating the purified capsular polysaccharide; and/or (g) formulating a vaccine with the capsular polysaccharide as a component.

In certain embodiments the alcohol solution added to a concentration sufficient to precipitate nucleic acid contaminants but not the capsular polysaccharide. In preferred embodiments, the alcohol is ethanol preferably added to a concentration of between about 10% and about 50% ethanol, more preferably to a concentration of between about 30% ethanol. The alcohol solution may optionally include a cation, preferably a metal cation, more preferably a divalent cation, most preferably calcium.

In certain embodiments, the protein adherent filter is an activated carbon filter.

BRIEF DESCRIPTION THE FIGURES

FIG. 3A shows the molecular structure of serotype specific cps of GBS from Type Ia and Type Ib.

FIG. 3B shows the molecular structure of serotype specific cps of GBS from Type III and Type V.

FIGS. 5A-D shows the growth curve and pH of medium for the (A) 090 strain, (B) H36b strain, (C) M781 strain, and (D) CJB111. The specific growth rate was calculated using OD values in a range of 0.1-2.4.

Figure 6:
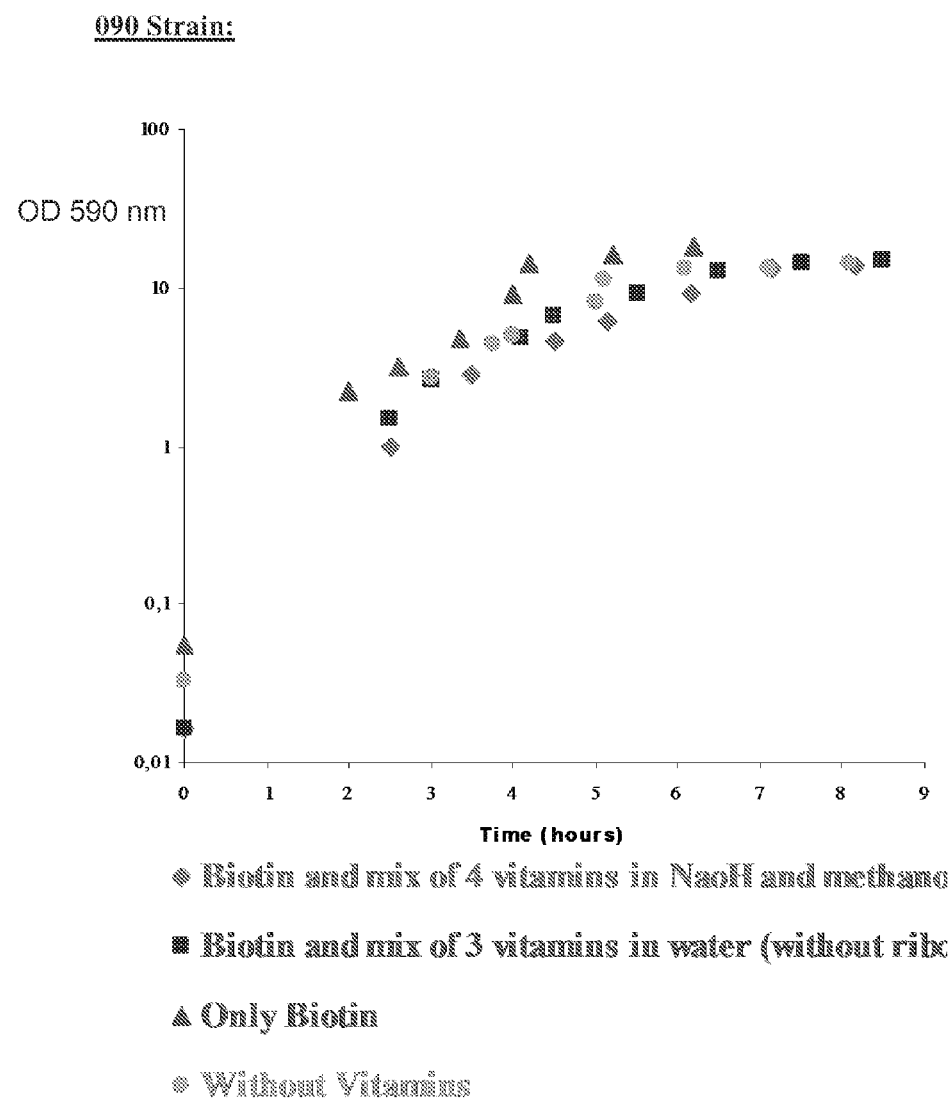

FIG. 6 shows (A) the growth curve for the 090 strain, (B) the cps concentration by the 090 strain, and (C) the cps production by gram cell dry weight, wherein the growth rate was determined for biotin and four vitamins in sodium hydroxide and methanol; biotin and three vitamins in water without riboflavin; only biotin; and without vitamins.

FIG. 7 shows (A) the growth curve for the H36b strain, (B) the cps concentration by the H36b strain, and (C) the cps production by gram cell dry weight, wherein the growth rate was determined for biotin and four vitamins in sodium hydroxide and methanol; biotin and three vitamins in water without riboflavin; and only biotin.

FIG. 8 shows (A) the growth curve for the M781 strain, (B) the cps concentration by the M781 strain, and (C) the cps production by gram cell dry weight, wherein the growth rate was determined for biotin and four vitamins in sodium hydroxide and methanol; biotin and three vitamins in water without riboflavin; and only biotin.

Figure 9:
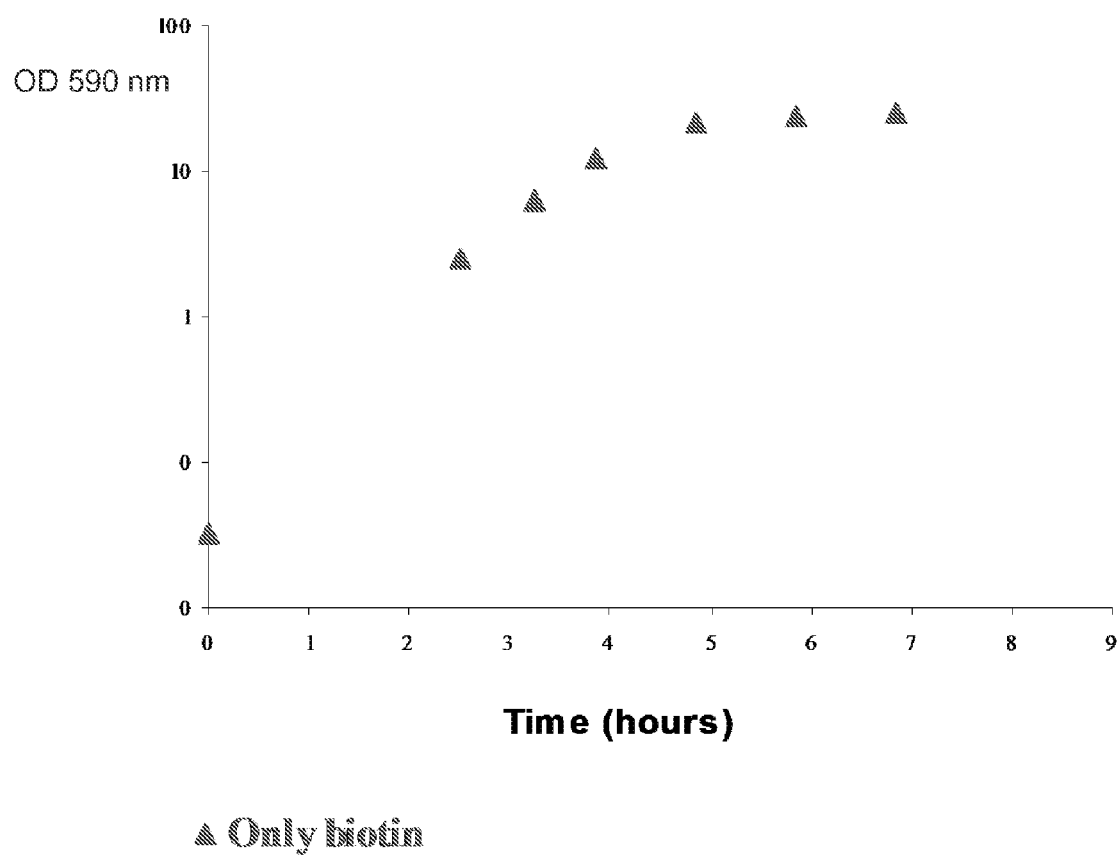

FIG. 9 shows the growth curve for the CJB111 strain, the cps concentration by the CJB111 strain, and the cps production by gram cell dry weight, wherein the growth rate was determined for biotin alone.

FIG. 10 shows (A) the growth curve for the 090 strain, (B) the cps concentration by the 090 strain, and (C) the cps production by gram cell dry weight, wherein the growth rate was determined for the feed batch technique; the instantaneous addition of yeast extract when the OD level is at 3 and at 5, followed by a linear addition of glucose; and the addition of the entire yeast extract in batch medium, followed by a linear addition of glucose.

FIG. 11 shows (A) the growth curve for the H36b strain, (B) the cps concentration by the H36b strain, and (C) the cps production by gram cell dry weight, wherein the growth rate was determined for the feed batch technique; the instantaneous addition of yeast extract when the OD level is at 3 and at 5, followed by a linear addition of glucose; and the addition of the entire yeast extract in batch medium, followed by a linear addition of glucose.

FIG. 12 shows (A) the growth curve for the M781 strain, (B) the cps concentration by the M781 strain, and (C) the cps production by gram cell dry weight, wherein the growth rate was determined for the feed batch technique; the instantaneous addition of yeast extract when the OD level is at 3 and at 5, followed by a linear addition of glucose; and the addition of the entire yeast extract in batch medium followed by a linear addition of glucose.

Figure 13:
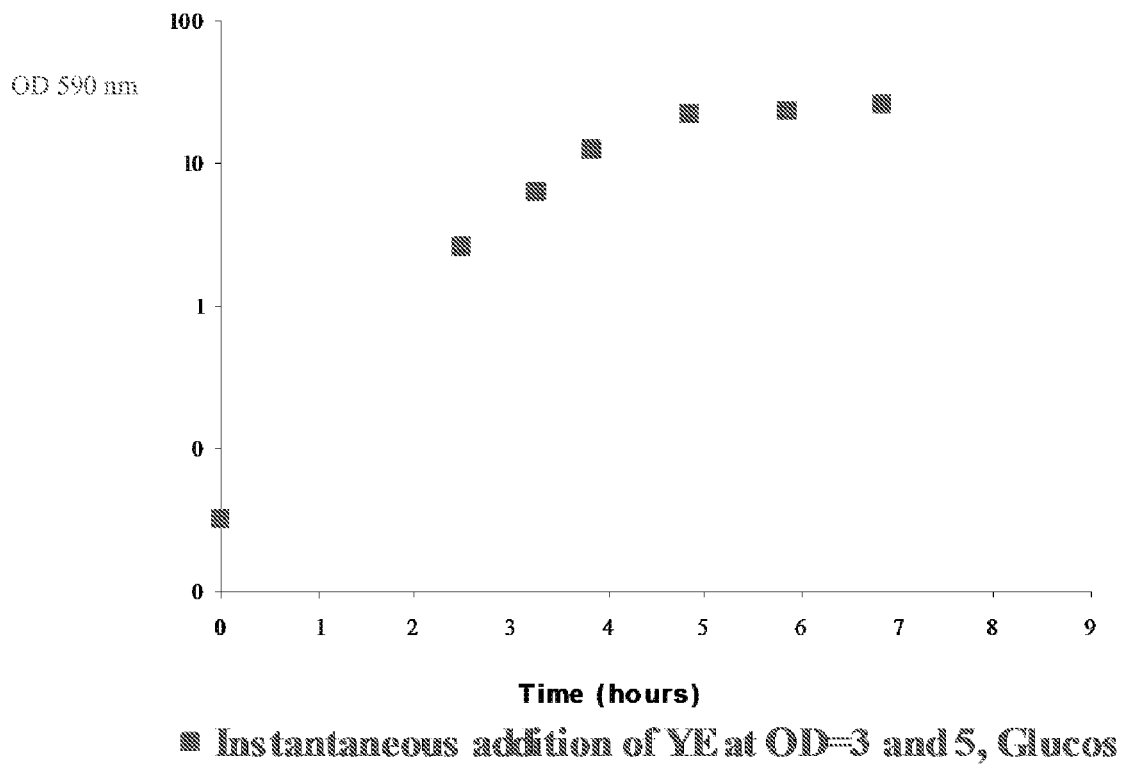

FIG. 13 shows the growth curve for the CJB111 strain, the cps concentration by the CJB111 strain, and the cps production by gram cell dry weight, wherein the growth rate was determined for the instantaneous addition of yeast extract when the OD level is at 3 and at 5, followed by a linear addition of glucose.

FIG. 14 provides the results of a DOT study, which shows (A) the growth curve for the H36b strain at 15%, 30%, and 60%, (B) the cps concentration by H36b strain, (C) the cps production by gram cell dry weight, and (D) the average productivity of the H36b strain.

FIG. 15 provides the results of a temperature study, which shows (A) the growth curve for the H36b strain at 34° C., 36° C., and 38° C., (B) the cps concentration by H36b strain, (C) the cps production by gram CELL DRY WEIGHT, and (D) the average productivity of the H36b strain.

FIG. 16 provides the results of a pH study, which shows (A) the growth curve for the H36b strain at 7.0, 7.3, and 7.5, (B) the cps concentration by H36b strain, (C) the cps production by gram cell dry weight, and (D) the average productivity of the H36b strain.

FIG. 17 provides the results of a pressure study, which shows (A) the growth curve for the H36b strain at 0.2 and 0.5 bar, (B) the cps concentration by H36b strain, (C) the cps production by gram cell dry weight, and (D) the average productivity of the H36b strain.

FIG. 18 shows the growth curve for M781 strain in (A) 500 mL Erlenmeyer flasks containing 100 mL of chemically defined medium (0.1 mL of w.s.), and (B) 2 L fermentor. The specific growth rate was calculated using OD values in a range of 0.1-0.7.

Figure 19:
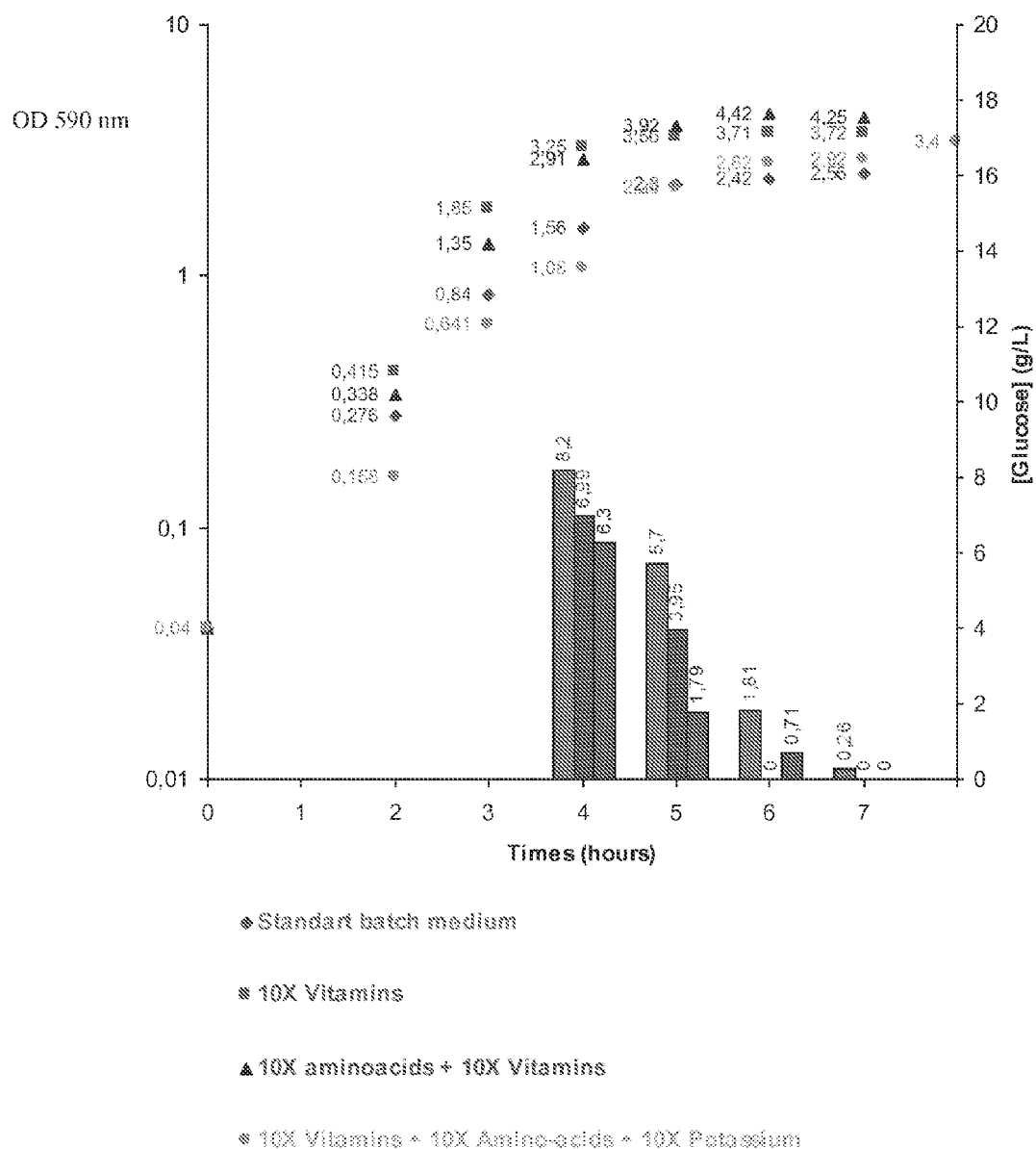

FIG. 19 shows the growth curve for the M781 strain as a plot graph, and glucose consumption as a bar graph for the standard batch medium; 10 times the quantity of vitamins; 10 times the quantity of amino acids and vitamins; and 10 times the quantity of vitamins, amino acids and potassium.

Figure 20:
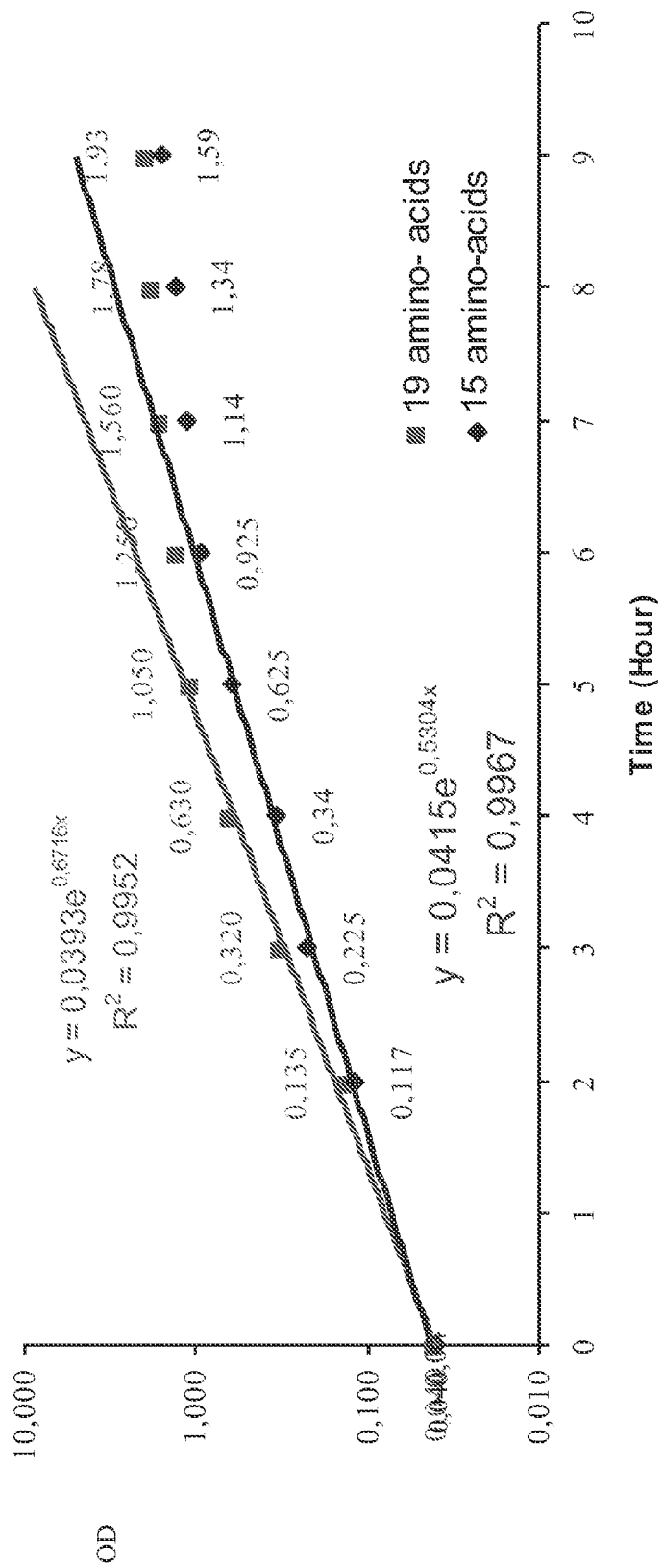

FIG. 20 shows the effect of the omission of alanine, aspartic acid, glutamine and proline on the growth of strain M781 of GBS in a defined medium.

Figure 21:
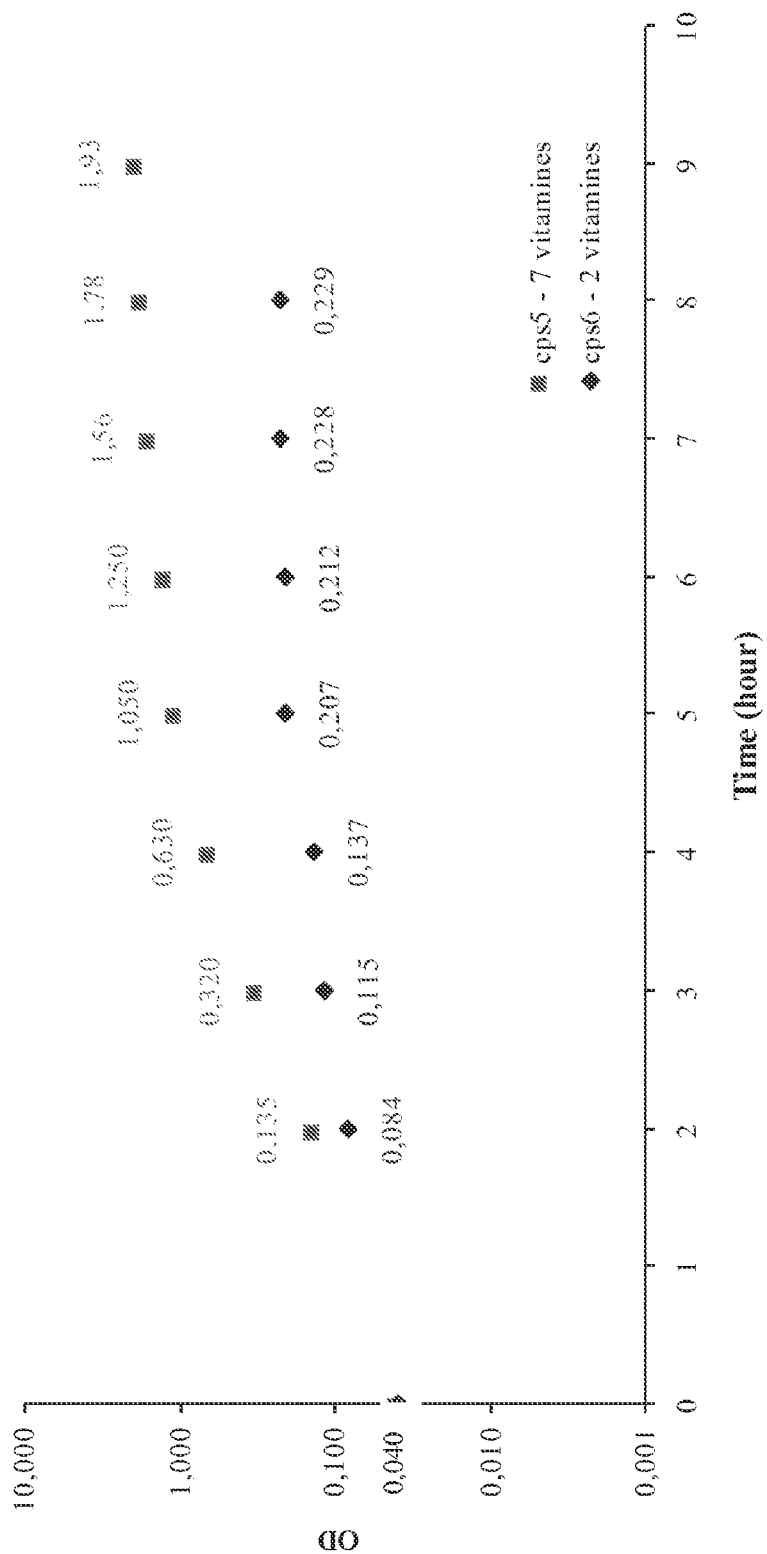

FIG. 21 shows the effect of omission of biotin, folic acid, pyridoxine, riboflavin and thiamine on the growth of strain M781 of GBS in a defined medium.

Figure 22:
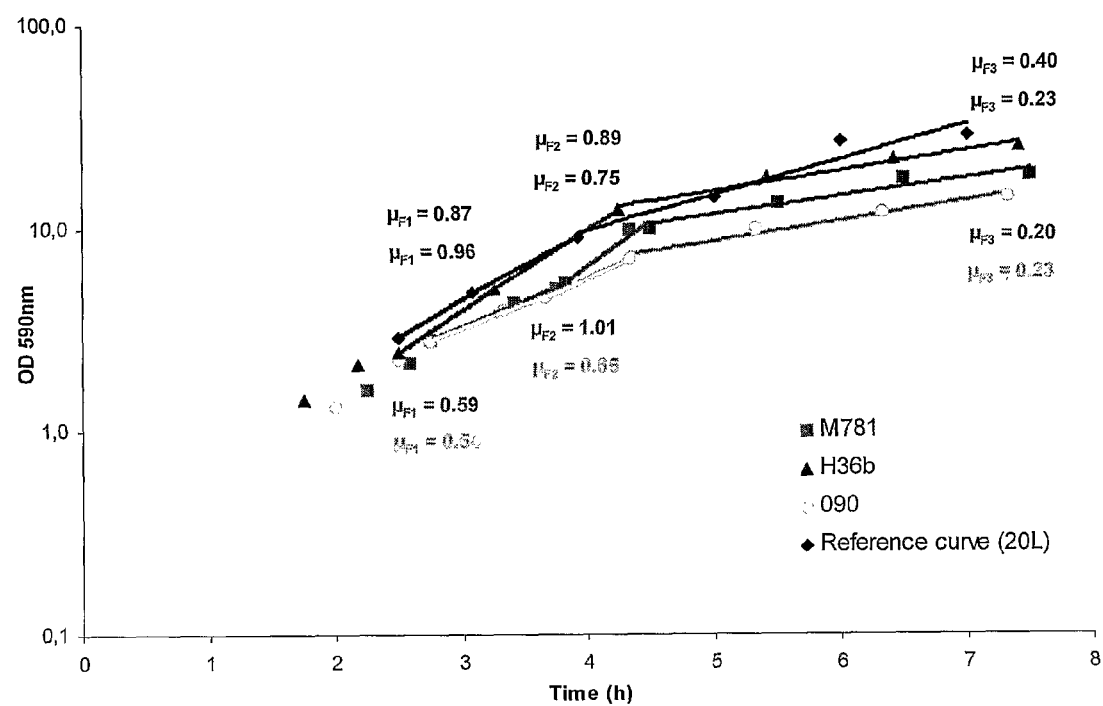

FIG. 22 shows the $OD_{590\ nm}$ profile of the first pre-test fermentation runs of the 3 strains, M781, H36b and 090, at a laboratory-scale.

Figure 23:
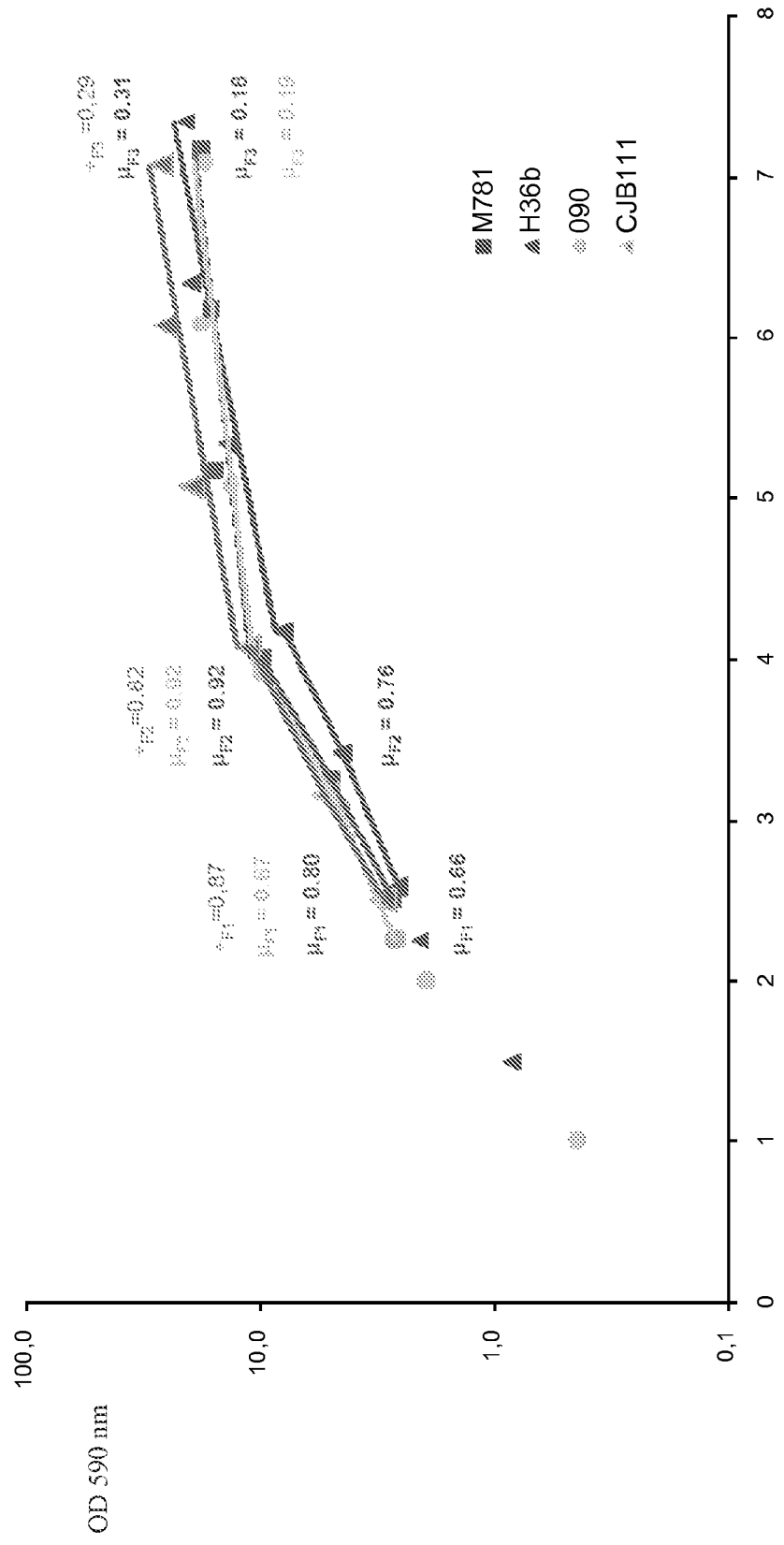

FIG. 23 shows the $OD_{590\ nm}$ profile of the second pre-test fermentation runs of the 4 strains, M781, H36b, 090, and CJB111, using a simplified process. The first simplification removed thiamine, riboflavin, pyridoxine HCl, and niacinamide from the vitamin solution. The second simplification was the modification of the parameters of the fed phases during the fermentation.

Figure 24:
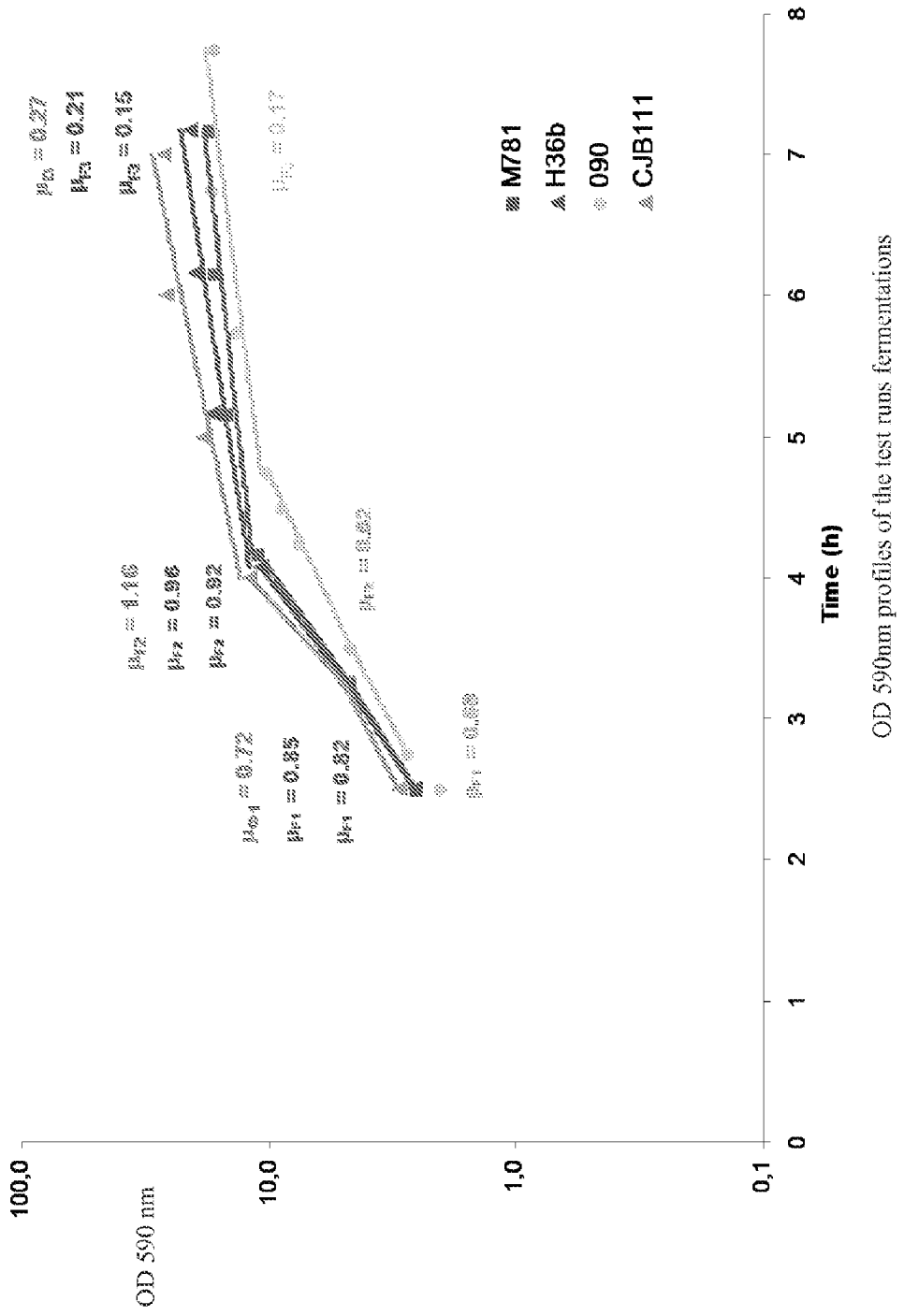

FIG. 24 shows the $OD_{590\ nm}$ profile of the test fermentation runs of the 4 strains, M781, H36b, 090, CJB111.

Figure 25:
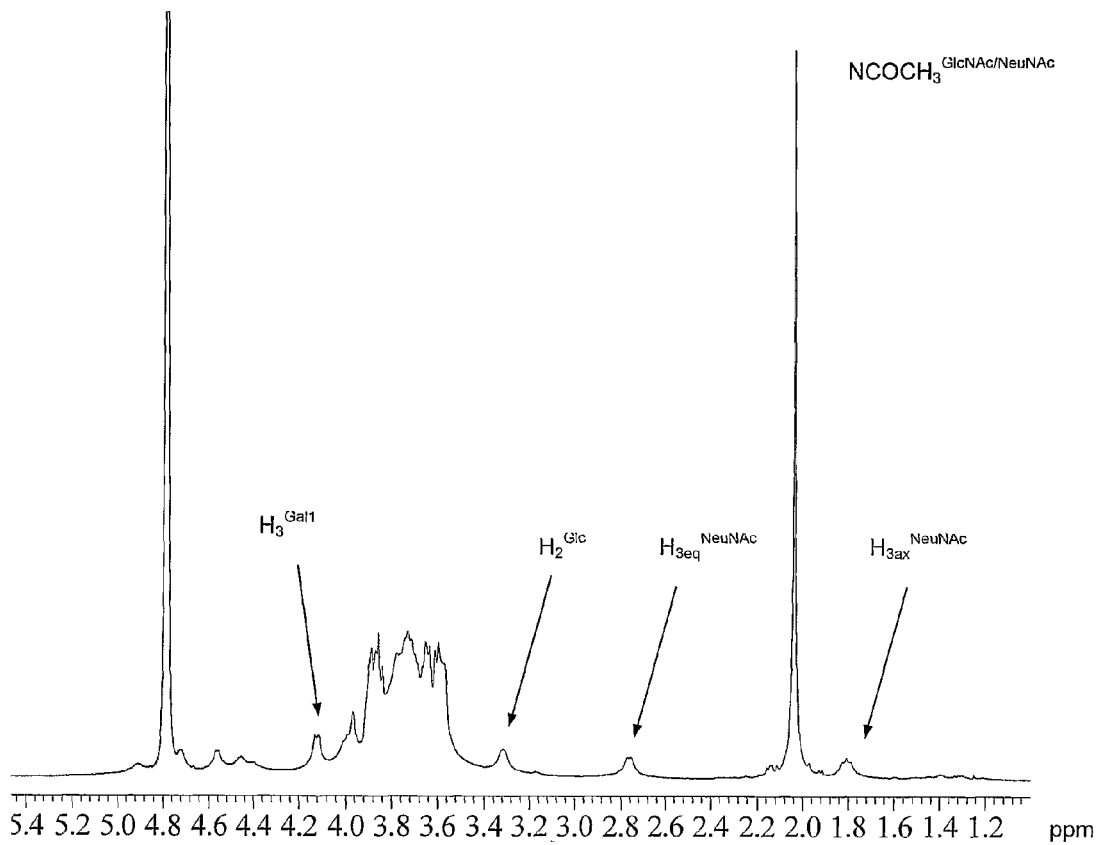

FIG. 25 shows the $^1H$ NMR spectrum of purified GBS Type Ia polysaccharide recorded at 25° C. Certain hydrogen are identified on the spectrum.

Figure 26:
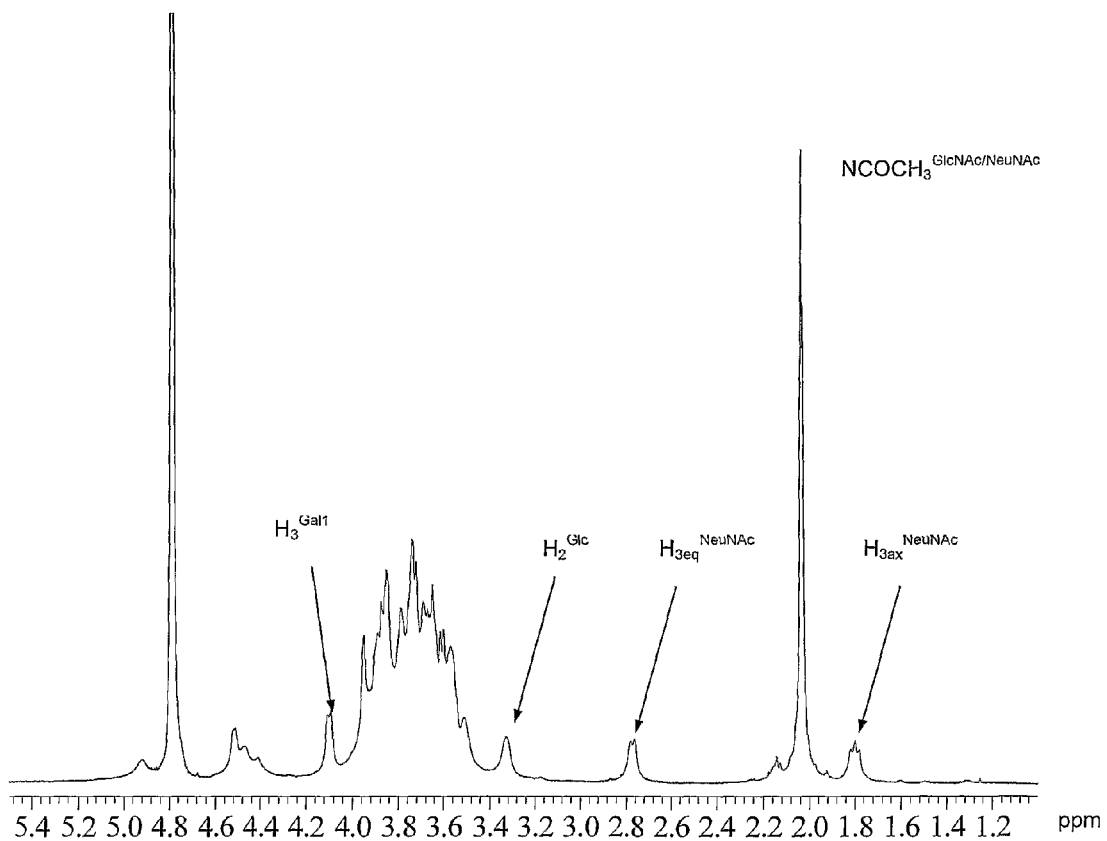

FIG. 26 shows the $^1H$ NMR spectrum of purified GBS Type Ib polysaccharide recorded at 25° C. Certain hydrogen are identified on the spectrum.

Figure 27:
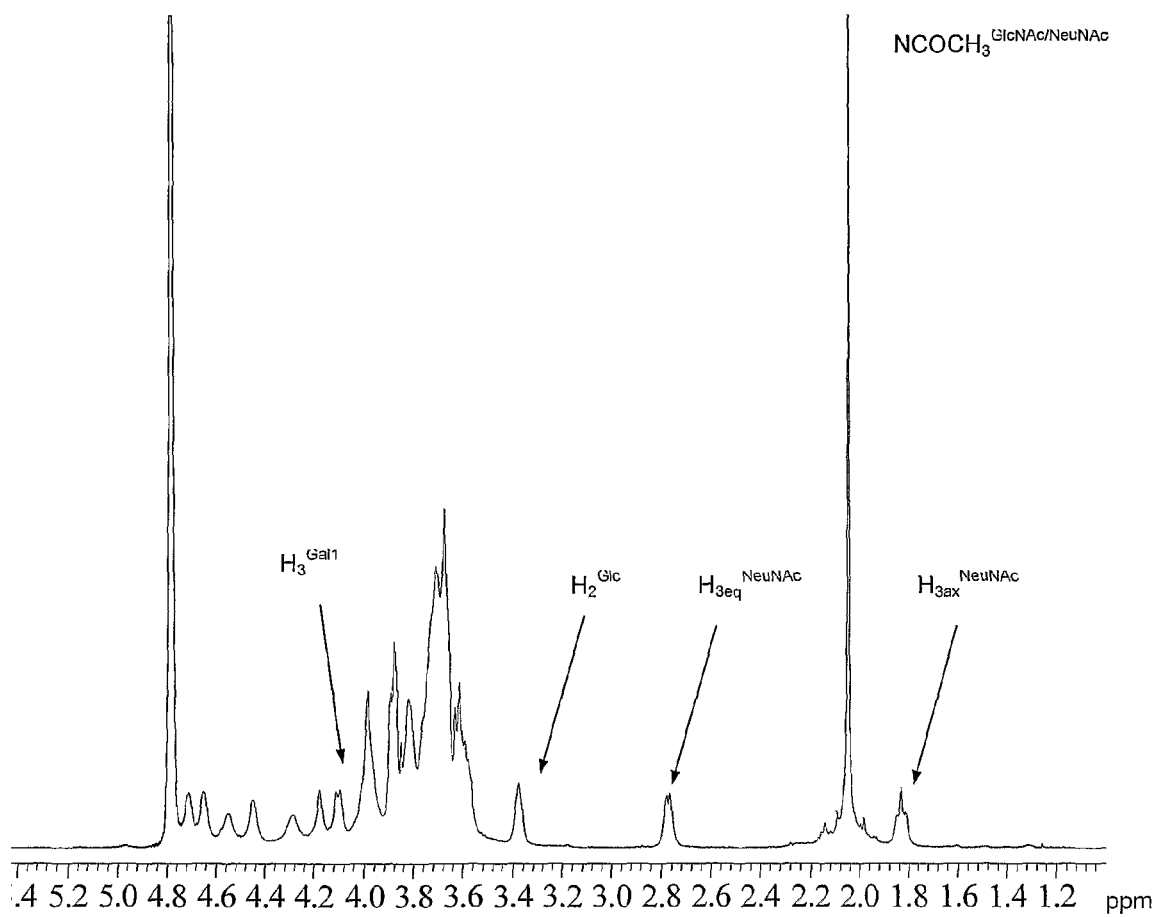

FIG. 27 shows the $^1H$ NMR spectrum of purified GBS Type III polysaccharide recorded at 25° C. Certain hydrogen are identified on the spectrum.

Figure 28:
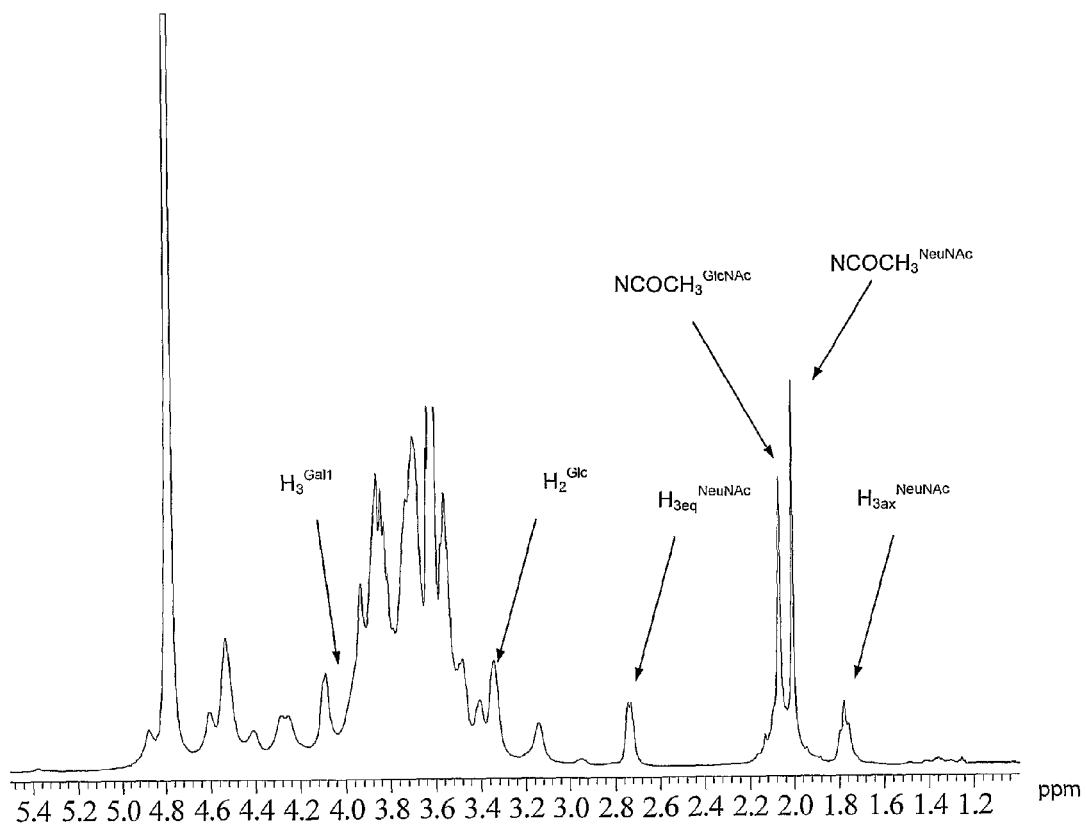

FIG. 28 shows the $^1$H NMR spectrum of purified GBS Type V polysaccharide recorded at 25° C. Certain hydrogen are identified on the spectrum.

Figure 29:
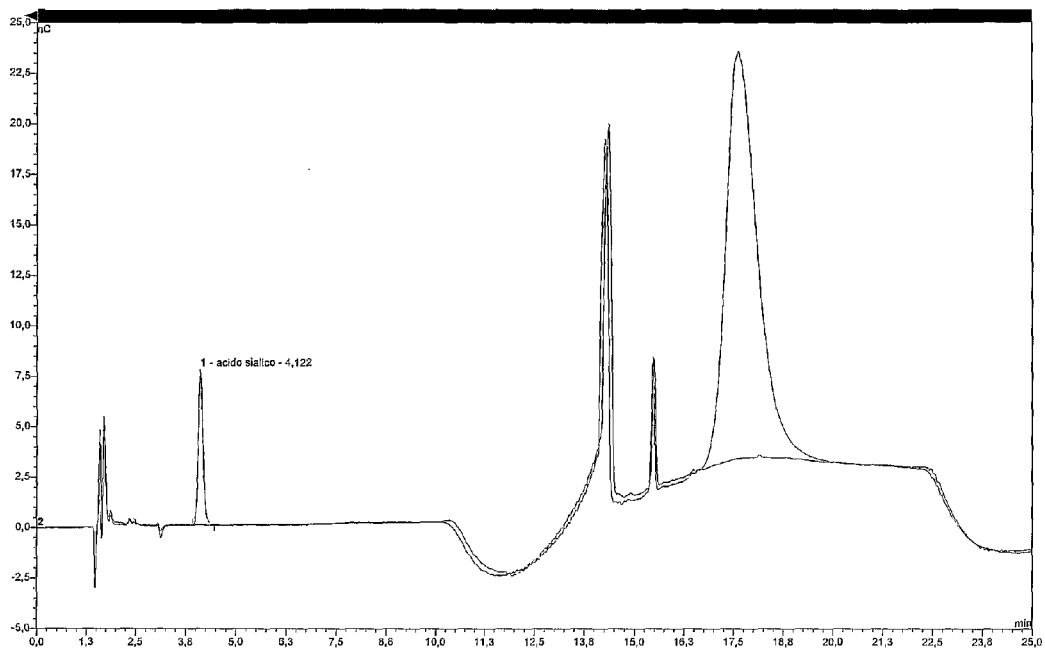

FIG. 29 shows an overlay of elution profiles of a polysaccharide sample and sialic acid standard (gray line) at 0.5 µg/ml.

Figure 30:
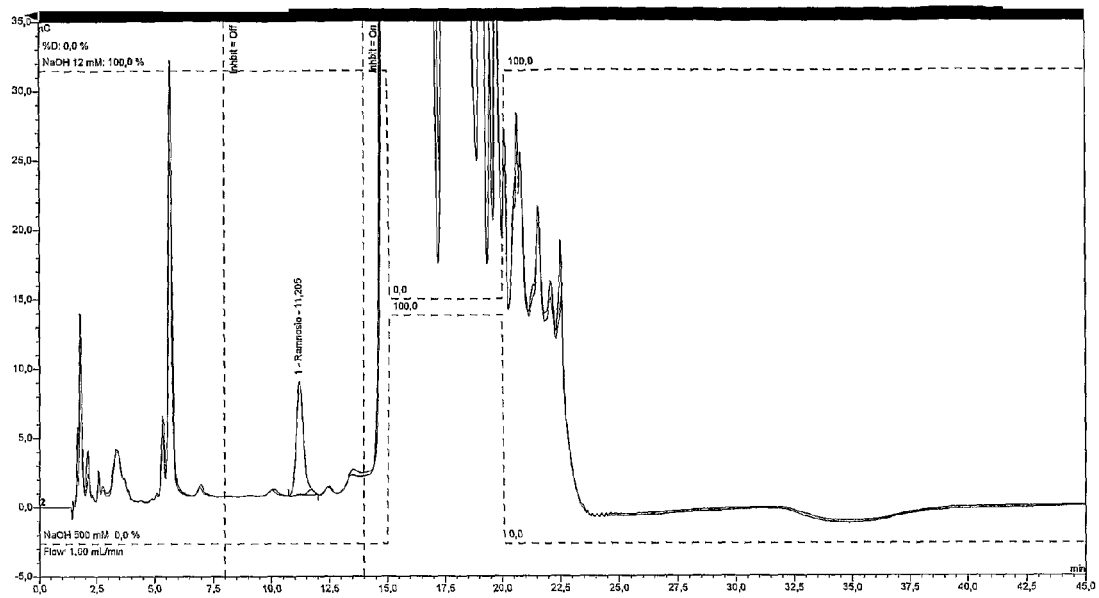

FIG. 30 shows an overlay of elution profiles of a polysaccharide sample and a polysaccharide sample with rhamnose added (gray line).

DETAILED DESCRIPTION OF PREFERRED EMBODIMENTS

The inventors have discovered that high yields of cps on a manufacturing scale can be obtained for any *Streptococcus* strain using fed batch culture, that is a culture which is initiated by the inoculation of cells into a finite volume of fresh medium and terminated by a single harvest after the cells have grown, with extra nutrients being added to the culture once the initial source of nutrients has been exhausted. Such high yields are comparable to or better than those obtained using continuous culture. Furthermore, the methods disclosed herein are not prone to the stability and contamination problems of continuous culture. The inventors have further developed an optimized purification protocol which significantly improves the impurities while keeping the protocol simple and inexpensive for manufacturing scale.

This disclosure provides a process for culturing *Streptococcus*, wherein the *Streptococcus* is grown in fed batch culture. Certain strains of *Streptococcus* are known to be "bad producers" of cps in that they typically produce low levels of cps in a culture. Examples of such bad producers include the GBS strains DK21 and 2603. However, using the methods disclosed herein, high levels of cps can be obtained even from such strains that are known to produce lower levels of cps. Therefore the invention provides a process for increasing the cps yield from a strain of *Streptococcus* comprising culturing *Streptococcus* in fed batch culture wherein, under batch or continuous culture conditions, the strain would only produce <30 mg cps/$g_{CDW}$ or <10 mg cps/$g_{CDW}$ in the case of "bad producers."

Preferably the invention provides a method of culturing *Streptococcus* in fed batch culture, wherein a high yield of cps is produced. Preferably the yield of cps is 10 mg/$g_{CPW}$ or more in the case of bad producers (preferably 15, 20, 25, or 30 or more) and 30 mg/$g_{CPW}$ or more in the case of other strains (preferably 40, 50, 60, 70, 80, 90, 100, 110, 120, 130, 140, 150, 160, 170, 180, 190, 200 or more). Preferably the yield of cps from the culture medium is 10 mg/L or more (e.g., 20, 30, 40, 50, 60, 70, 80, 90, 100, 120, 140, 160, 180, 200, 220, 240, 260, 280, 300 or more). More preferably, the yield of cps from the culture medium is 50 mg/L or more (e.g., 150, 200, 250, 300, 350, 400, 450, 500, 550, 600, 650 or more). Thus, this invention allows the production of cps at a far higher yield per unit volume compared with continuous culture. In some cases, the yield per unit volume may be at least twice the quantity produced using continuous culture, more preferably two and one half times or three times the quantity produced using continuous culture.

This invention also provides a method for cultivating the *Streptococcus* strain by fermentation, comprising two instantaneous additions of yeast extract, followed by a linear addition of a carbon source, preferably without use of an algorithm to monitor pH. The preferred carbon source for the linear addition is glucose. Each addition is initiated at a designated OD level, which is selected to achieve a higher volumetric production of cps by regulating the bacteria growth rate and to adapt the micro-organism to produce a maximum serotype specific cps.

In one embodiment, the first instantaneous addition of yeast extract is initiated at an OD level between 2.8-3.2, preferably about 3.0. In another embodiment, the second instantaneous addition of yeast extract is initiated at an OD level between 4.3-4.7, preferably about 4.5. In another embodiment, the linear addition of the carbon source is initiated at an OD level between 9.8-10.0, preferably about 10.

Overall, the linear addition of a carbon source is an improvement over the previous complex fed batch fermentation process that used an algorithm to control the cultivating by monitoring a pH of the cultivating medium.

Figure 1:
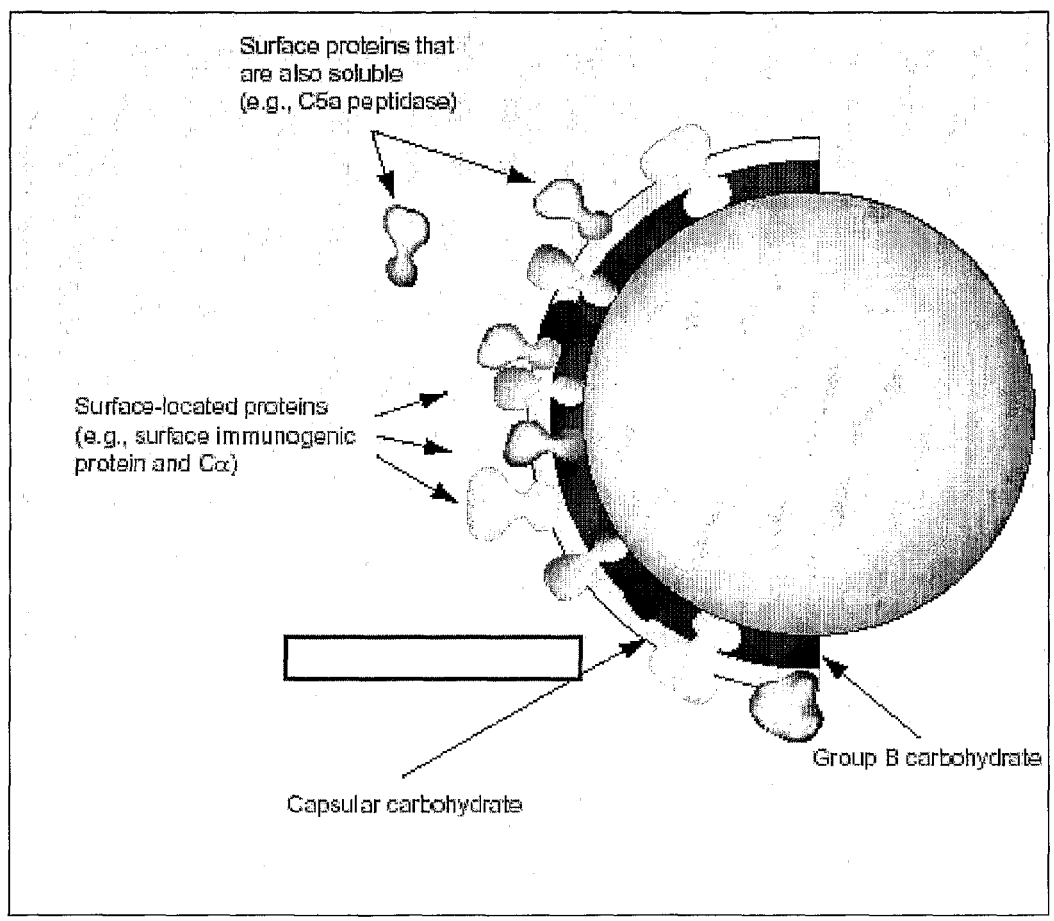
FIG. 1 shows the capsular polysaccharides that are potential GBS vaccine targets.
Figure 2:
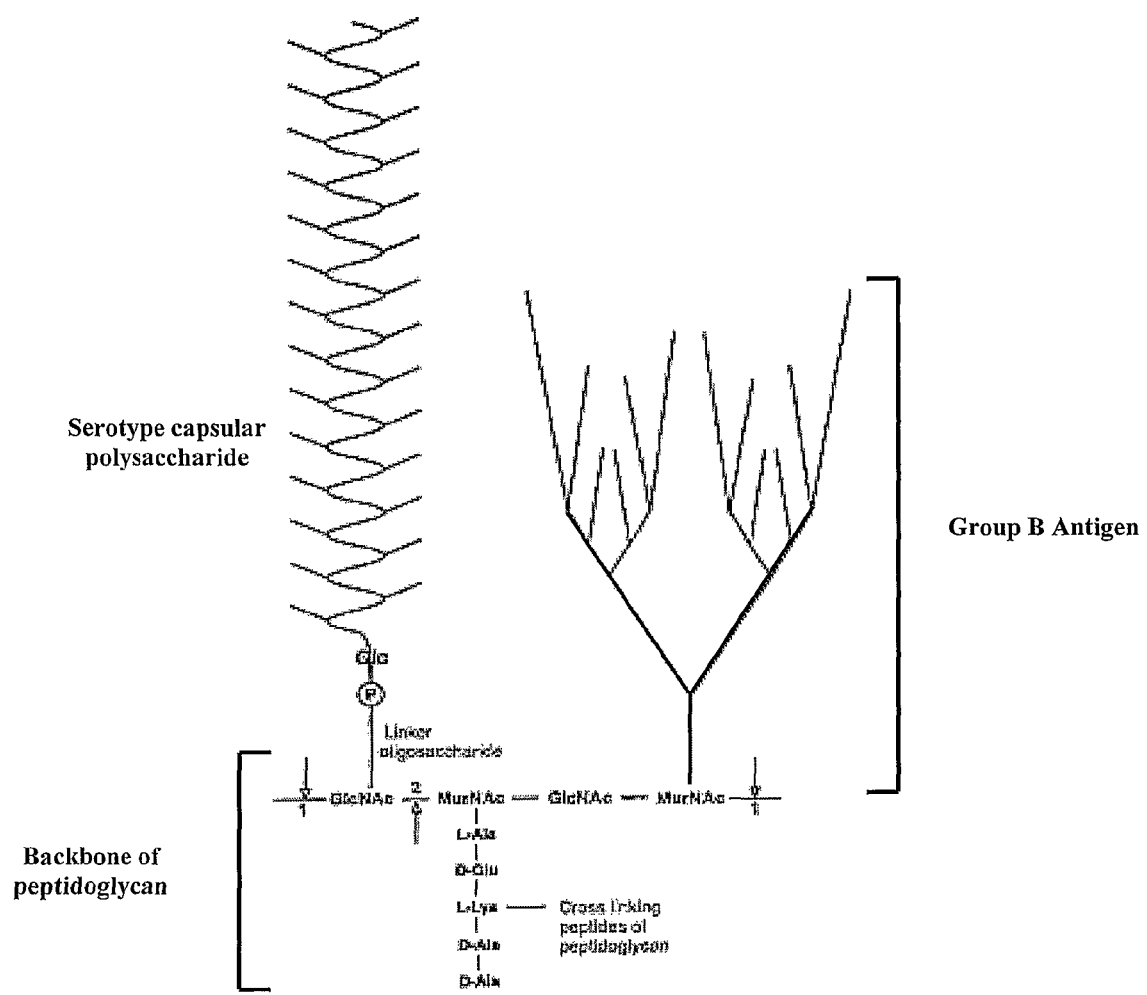
FIG. 2 is the schematic representation of a proposed model for the linkage of capsular polysaccharides (cps) and Group B carbohydrate of GBS.

Following the cultivating, the bacteria may undergo further processing steps in order to purify the cps and to conjugate it to a carrier protein. The invention therefore may further comprise steps of purifying cps from the bacteria, and conjugating the capsular saccharide to a carrier protein, to give a protein-saccharide conjugate (see FIGS. 1-2). The purified cps may undergo further processing steps in order to prepare pharmaceutical preparations. In preferred embodiments, the purification will be carried out using the improved purification protocol disclosed herein.

*Streptococcus*

The term "*Streptococcus*" refers to bacteria that may be selected from *S. agalactiae* (GBS), *S. pyogenes* (GAS), *S. pneumoniae* (pneumococcus) and *S. mutans*. The *streptococcus* may alternatively be *S. thermophilus* or *S. lactic*. Preferably the *Streptococcus* is GBS. If the *Streptococcus* used is GBS, then preferably the serotype selected is 1a, 1b, 3, 4 or 5. Preferably the strains of GBS used are 090 (1a), 7357 (1b), H36b (1b), DK21 (2), M781 (3), 2603 (5), or CJB111 (5). See FIGS. 3A-B. If the *Streptococcus* used is *S. pneumoniae*, then preferably the serotypes selected are one or more, or all of 4, 6B, 9V, 14, 18C, 19F, and 23F. Serotype 1 may also preferably be selected. Preferably the serotypes selected are one or more, or all of 1, 3, 4, 5, 6B, 7F, 9V, 14, 18C, 19F, and 23F.

Moreover, the culture produced using the method of the invention may be homogeneous (i.e. consists of a single species or strain of *Streptococcus*), or may be heterogeneous (i.e. comprises two or more species or strains of *Streptococcus*). Preferably the culture is homogeneous.

The *Streptococcus* used may be a wild type strain or may be genetically modified. For instance, it may be modified to produce non-natural capsular polysaccharides or heterologous polysaccharides or to increase yield.

Production Process Overview

The production of GBS can be divided into four parts: (1) the production by fermentation of each of the cps and their primary recovery; (2) the purification of the microfiltration permeate; (3) the formulation of the dried purified cps; and (4) the characterization of the glycoconjugate biomolecules.

Figure 4:
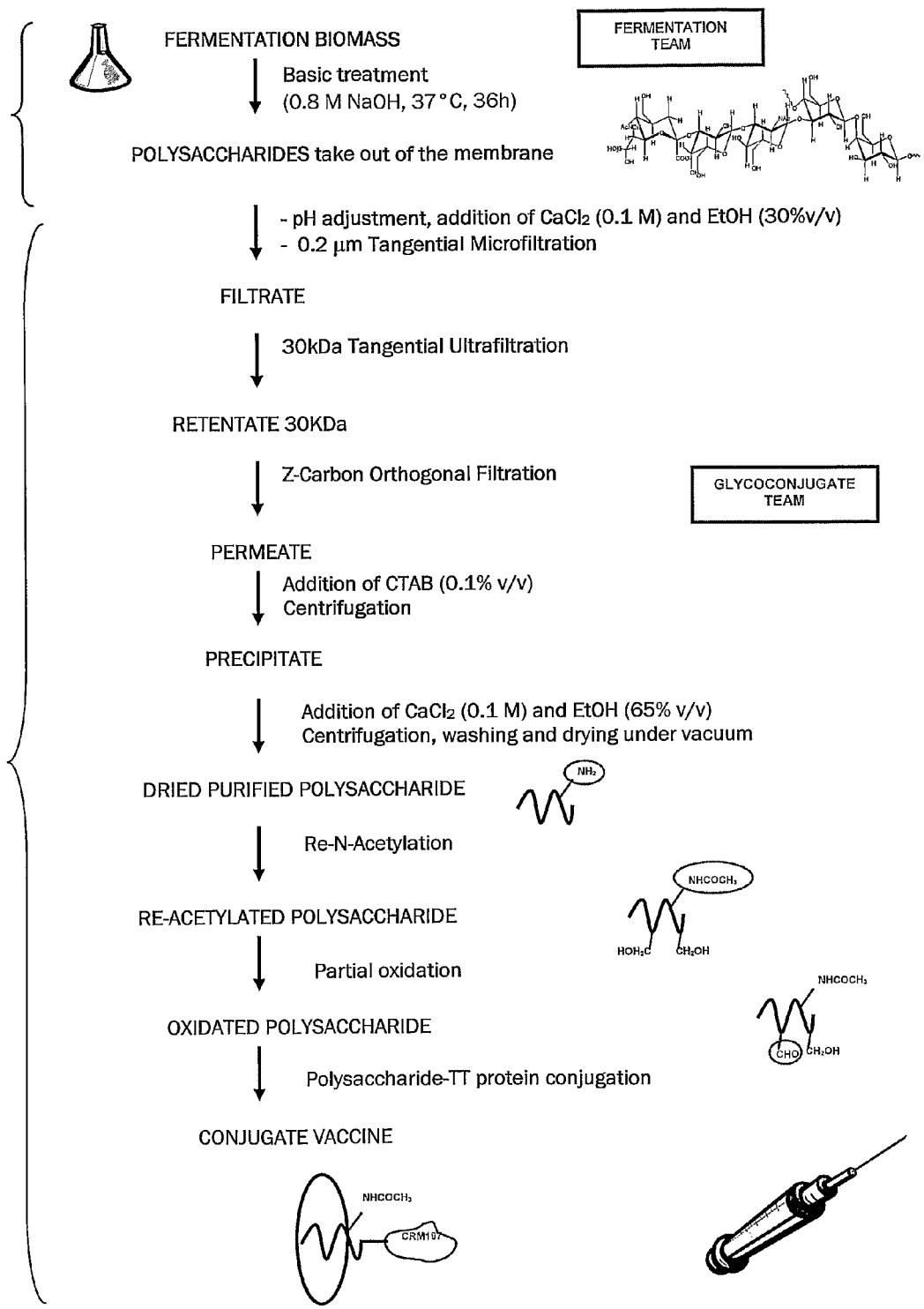
FIG. 4 shows the production process of glycoconjugate vaccine against GBS.
Figure 5A:
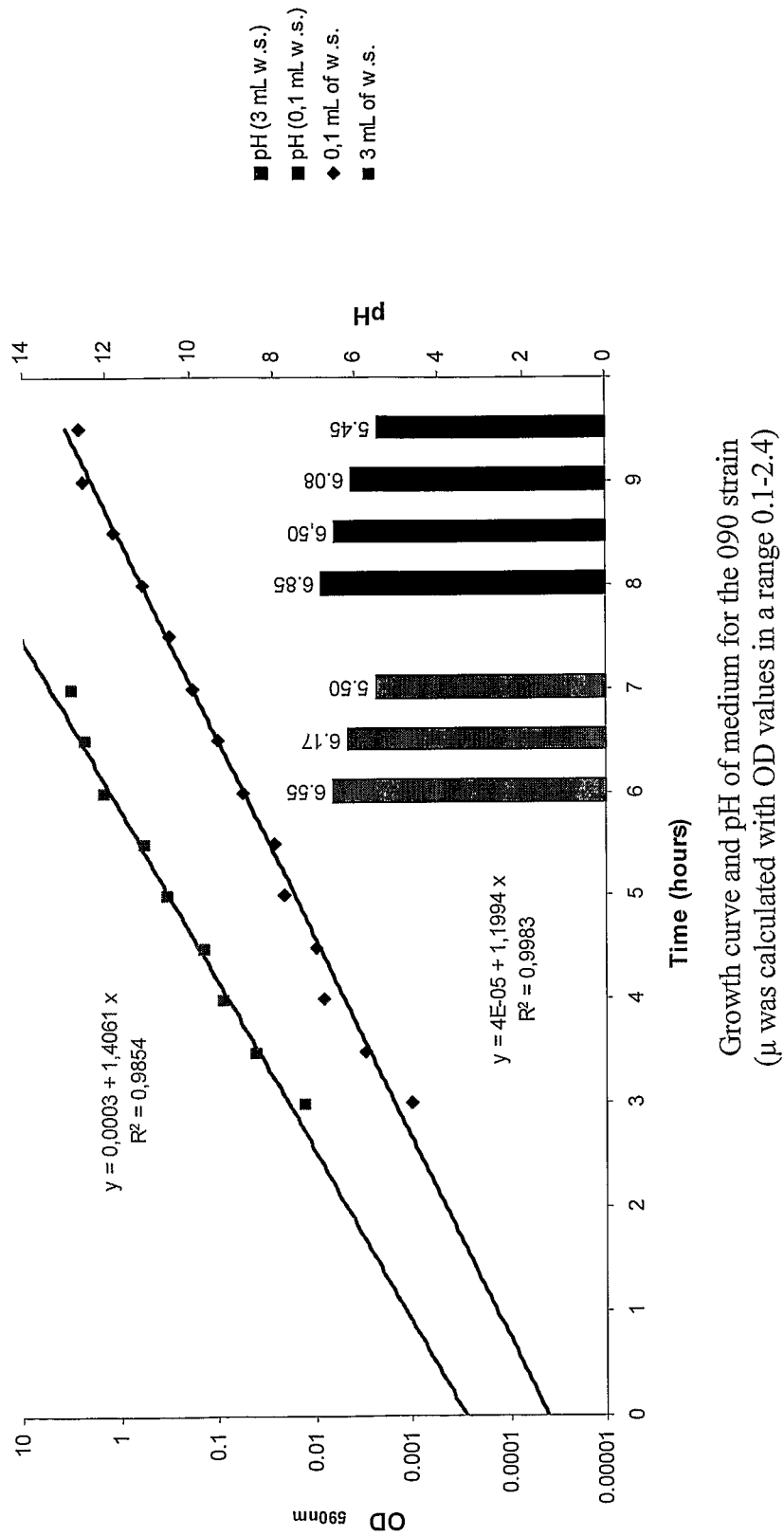
Figure 5B:
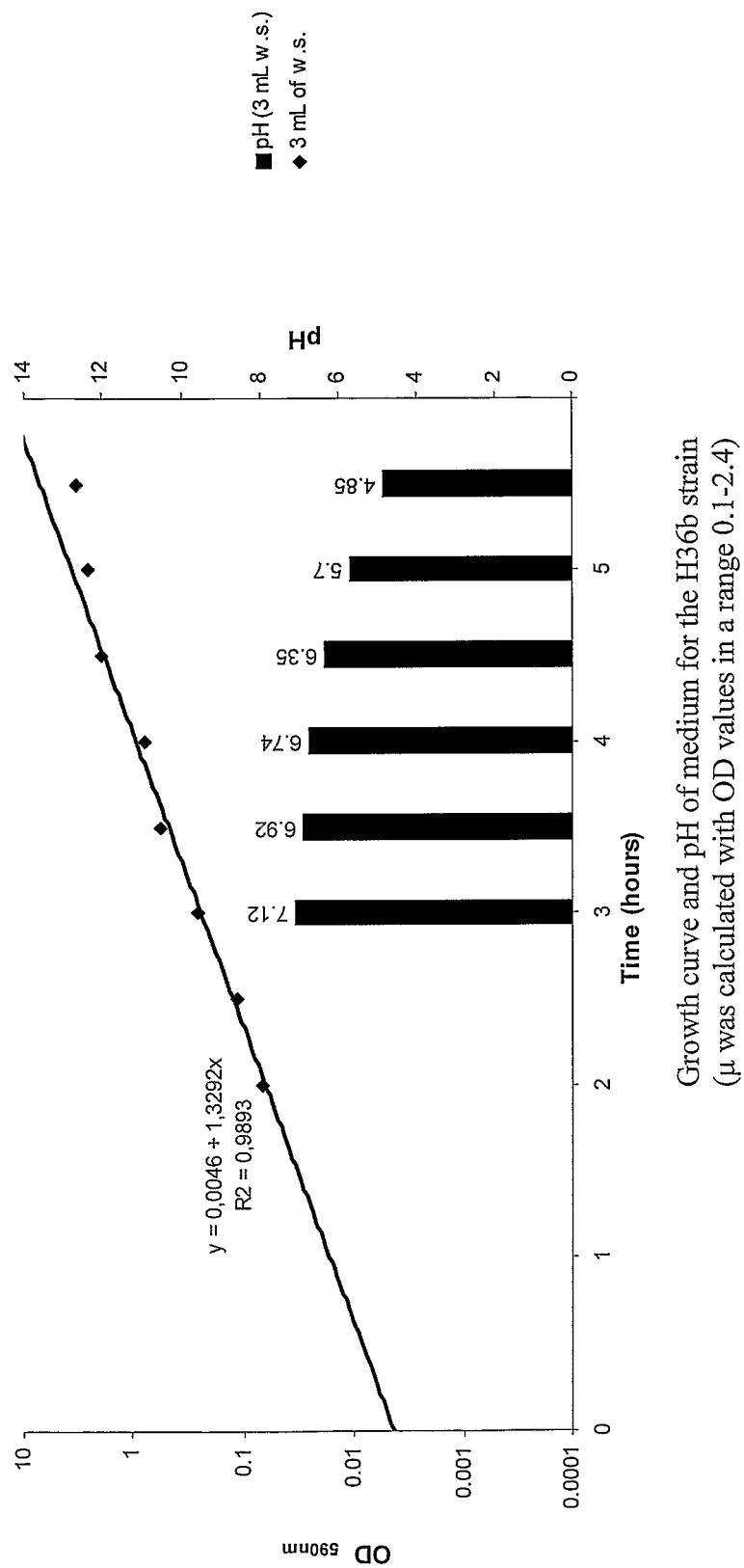
Figure 5C:
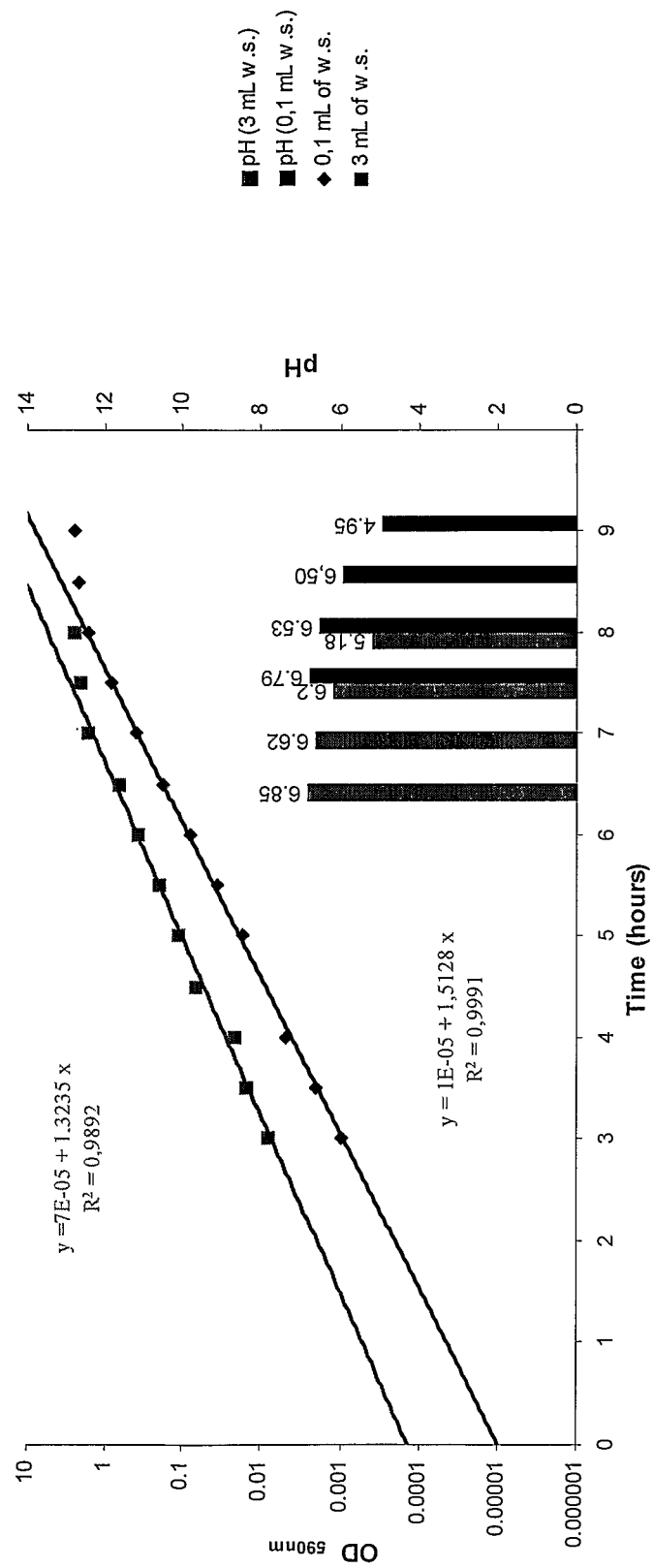
Figure 5D:
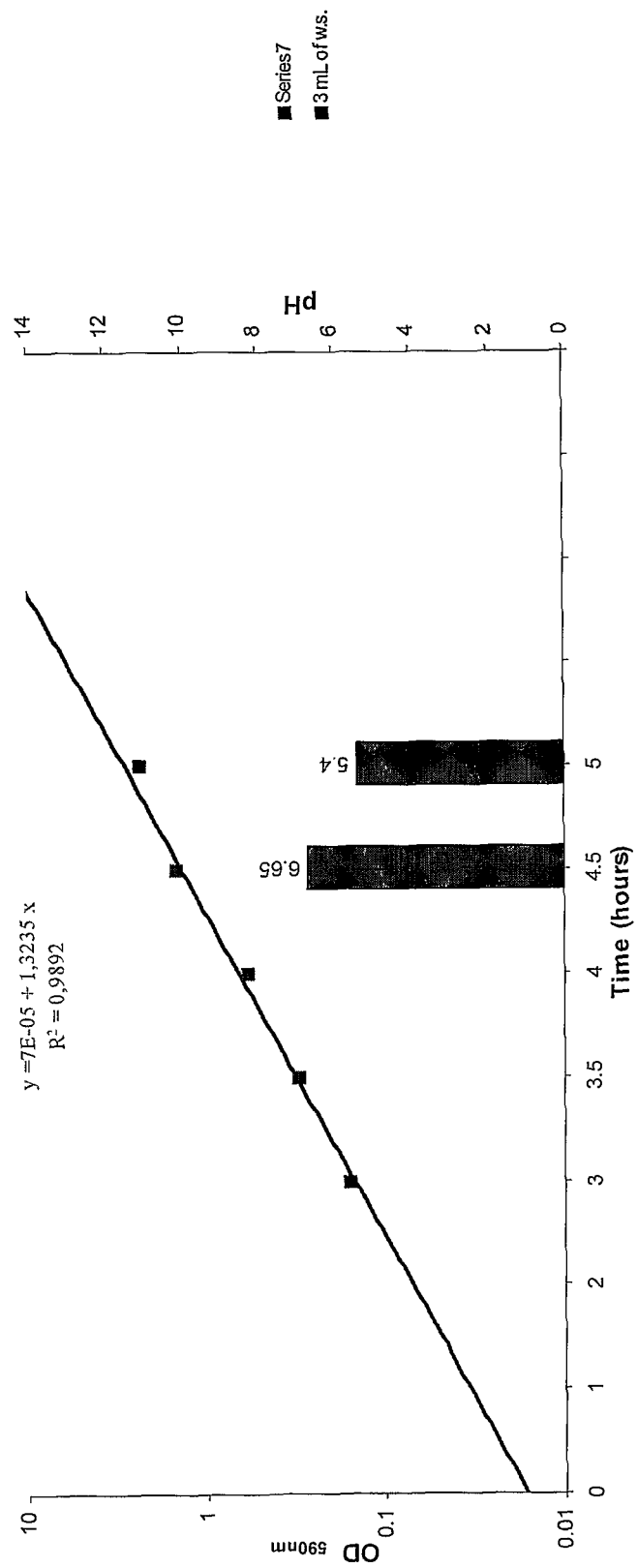

The first step may be optimized in a pilot-scale fermentation hall, and consists of the production of biomass by fermentation, the continuous flow centrifugation of the biomass, the collection of the pellet (or cellular paste), the inactivation of the microorganism and the release of the cps, and finally the microfiltration of the cellular paste with the collected permeate. The fermentation consists of (1) inoculum preparation, (2) the fermentation, the centrifugation of the biomass, the chemical treatments of the pellet and the microfiltration of the pellet as presented in FIG. 4.

The invention provides a method for producing cps on a manufacturing scale, which includes a method for providing an inoculum of a strain of *Streptococcus* expressing the cps, and a method for cultivating the strain by fermentation. The cultivating consists of monitoring the optical density (OD) of the cultivating medium such that when the OD reaches designated addition levels which prompts the two instantaneous additions of yeast extract, followed by a linear addition of a carbon source to a cultivating medium as opposed to an algorithm to control the cultivating by monitoring a pH of the cultivating medium.

Culture of the Inoculum

The culture of the inoculum may be performed in shake flasks sterilized using an autoclave at 121° C. The inoculum contains complex medium (consisting of yeast extract, $Na_2HPO_4.2H_2O$, $NaH_2PO_4.H_2O$, and monohydrated glucose with a neutral pH approximately 7.3), a solution of vitamins (consisting of thiamine, riboflavin, pyridoxine HCl, and niacinamide, diluted in NaOH), and a biotin solution. In preferred embodiments, the solution of vitamins is omitted and only the biotin solution is used as a vitamin supplement.

In a preferred embodiment, each flask is inoculated with 2.75±0.25 mL of working seeds. The culture is maintained at approximately 35° C. with agitation at approximately 200 rpm in the incubator for approximately 4 hours. After this time, the biomass concentration was evaluated by measuring the OD at 590 nm and performing a Gram stain. If the value of $OD_{590\ nm}$ is between approximately 0.6-1.8, and if the Gram stain produces only Gram positive cocci, the contents of the flasks are pooled into a heat-sterilized bottle connected to the incubation line of the fermentor.

During the inoculum preparation, the preferred conditions are as follows: the initial pH of the medium is 7.3±0.1, the volume of working seed is 2.5-3.0 ml/flask, the temperature of incubation is 35±1° C., and the agitation speed is 200±10 rpm. At the end of the culture in the flasks, the preferred final $OD_{590\ nm}$ is between 0.6-1.8, and the preferred Gram stain produces only Gram positive cocci. In the pooled bottle, the preferred purity of the culture is such that there is no contaminant. Finally, the preferred time of incubation is between 3-5 hours.

Fed Batch Fermentation Process

The invention provides an improved method of culturing the *Streptococcus* using a fed batch process on a manufacturing scale (see FIGS. 6-18). Fed batch culture may be either fixed volume fed batch or variable volume fed batch. In fixed volume fed batch culture, the limiting substrate is fed without diluting the culture (e.g., using a concentrated liquid or gas or by using dialysis). In variable volume fed batch culture, the volume changes over fermentation time due to the substrate feed.

During the fermentation process in the 300 L fermentor, the preferred conditions are as follows: the temperature of the culture is set at 36±1° C., the overpressure inside the fermentor is set at approximately 0.2 bar, the pH is set at 7.3±0.1 and adjusted using 4M NaOH, the initial stir is set at 50 rpm, the initial airflow is set at 20 L/min, the level of foam in the fermentor is visually monitored and adjusted using antifoam PPG 2500 if necessary, the dissolved oxygen tension (DOT) is set at 30% and regulated in cascade by stirring (between 50-350 rpm), the air airflow (between 20-100 L/min, and the oxygen flow (between 0-100 L/min).

This invention provides two instantaneous additions of yeast extract at specified OD levels, followed by a linear addition of a carbon source to the cultivating medium. Samples are taken during the batch phase of the fermentation, two hours after inoculation, and the $OD_{590\ nm}$ is measured. Samples are taken every 15 minutes until the $OD_{590\ nm}$ reaches 3 at which point the first instantaneous batch addition is initiated using a 150 g/L yeast extract solution. Approximately 45 minutes after the first addition, the $OD_{590\ nm}$ is measured again. Samples are taken every 15 minutes until the $OD_{590\ nm}$ reaches 5, at which point a second instantaneous batch addition is initiated using a 150 g/L yeast extract solution. When the $OD_{590\ nm}$ reaches 10-12, a linear addition is initiated. During this linear addition, a sample is taken every hour to measure the $OD_{590\ nm}$. The linear addition lasts approximately 3 hours at which time the automatic controls of the parameters are stopped. The stir is regulated at 100 rpm and the temperature at 30° C.

Growth Medium

Any type of liquid growth medium may be used which is suitable for maintaining growth of *Streptococcus* species. Preferred media include complex media such as Columbia broth, LB, Todd-Hewitt, OC medium, blood broth or brain-heart infusion; semi-defined media such as MCDM; chemically defined media for *Streptococcus* such as M1, MC, FMC (Ref. 11), or C-48 (Ref. 12); and media composed for growth of eukaryotic cell lines containing necessary auxotrophic components such as RPMI, spent medium, McCoy's and Eagle's. A typical growth medium contains yeast extract, as well as other factors essential for growth including lipids (long chain fatty acids such as linoleic or oleic acid), steroids (such as cholesterol), purines and pyrimidines, minerals, vitamins and growth factors, amino acids (L- and/or D-form) and/or chemical elements or inorganic ions (such as Fe, K, Mg, Mn, Ca, Co, Cu, P and/or Zn). By increasing the concentration of the medium, higher ODs may be achieved, resulting in a higher volumetric production of cps. Accordingly, the complex medium preferably comprises yeast extract, a phosphate source, a carbon source, a vitamin source, and optionally an amino acid source to grow *Streptococcus*, wherein the vitamin source consists of biotin, and optionally one or more vitamins chosen from niacinamide, riboflavin, thiamine hydrochloride and pyridoxine hydrochloride.

The chemically defined medium preferably comprises a phosphate source, a mineral source, a carbon source, a vitamin source, and an amino acid source to grow *Streptococcus*, wherein the vitamin source consists of calcium pantothenate, niacinamide, and one or more vitamins chosen from biotin, riboflavin, thiamine hydrochloride, pyridoxine hydrochloride and folic acid.

The growth medium may additionally comprise one or more of an antibiotic and an antifoam agent. Typical antibiotics include kanamycin, ampicillin and tetracycline. The antibiotics may be used to exert a selection pressure to select for particular bacteria which contain an antibiotic resistance gene and/or to select for Gram positive bacteria (e.g., Streptococci). This can therefore be used to maintain selection pressure for the bacteria expressing the desired cps. For example, the antibiotic aztrianam is effective against Gram negative, but not Gram positive bacteria. Antifoaming agents are known in the art and may include mineral oil, medical oil, highly formulated polysiloxane glycol copolymers, silicone compounds and emulsions, oxalkylated compounds, mineral oil/synthetic blends, glycol/ester blends, etc.

The culture may also include the addition of various other factors that enhance growth, such as, lipids (such as long chain fatty acids such as linoleic or oleic acid), steroids (such as cholesterol), purines and pyrimidines, vitamins and growth factors, amino acids (L- and/or D-form) and/or chemical elements or inorganic ions (such as Fe, K, Mg, Mn, Ca, Co, Cu, P and/or Zn).

If the growth medium contains additives obtained from animals, such as bovine serum albumin, these should be obtained from sources free of transmissible spongiform encephalopathies to avoid contamination of the medium and eventually the cps.

Carbon Source

The type of carbon source used is not essential. Preferably a primary carbon source is selected from the group consisting of glucose, fructose, lactose, sucrose, maltodextrins, starch, inulin, glycerol, vegetable oils such as soybean oil, hydrocarbons, alcohols such as methanol and ethanol, organic acids such as acetate. More preferably the carbon source is selected from glucose, glycerol, lactose, fructose, sucrose and soybean oil. The term "glucose" includes glucose syrups, i.e. glucose compositions comprising glucose oligomers. The carbon source may be added to the culture as a solid or liquid. Preferably the carbon source is controlled to avoid osmotic stress on the cells which can result in overfeeding. This is usually achieved by not adding the entire carbon source required for the duration of the fermentation to the initial batch culture. The carbon source is also controlled to avoid depletion which can result in growth limitation and pigment production (Ref. 13).

Nitrogen Source

The type of nitrogen source used is not essential. Preferably, the nitrogen source is selected from urea, ammonium hydroxide, ammonium salts (such as ammonium sulphate, ammonium phosphate, ammonium chloride and ammonium nitrate), other nitrates, amino acids such as glutamate and lysine, yeast extract, yeast autolysates, yeast nitrogen base, protein hydrolysates (including, but not limited to peptones, casein hydrolysates such as tryptone and casamino acids), soybean meal, Hy-Soy, tryptic soy broth, cotton seed meal, malt extract, corn steep liquor and molasses. More preferably, a nitrogen source is selected from ammonium hydroxide, ammonium sulphate, ammonium chloride and ammonium phosphate. Most preferably, the nitrogen source is ammonium hydroxide. The use of ammonium hydroxide as a nitrogen source has the advantage that ammonium hydroxide additionally can function as a pH-controlling agent.

If ammonium sulphate and/or ammonium phosphate are used as a nitrogen source, at least a portion of the sulfur and/or phosphorus requirement of the microorganism may be met.

Phosphorus Source

As noted above, phosphorus may be added to the growth medium. The phosphorus may be in the form of a salt, in particular it may be added as a phosphate (such as ammonium phosphate as noted above) or polyphosphate. If a polyphosphate is used, it may be in the form of a phosphate glass, such as sodium polyphosphate (Ref. 14). Such phosphate glasses are useful as their solubility properties are such that concentrated nutrient media can be prepared with no resulting precipitation upon mixing.

Other Variables

The temperature of the culture is kept between 30-45° C. (e.g., at 31, 32, 33, 34, 35, 36, 37, 38, 39, 40, 41, 42, 43, 44° C.). Preferably the temperature is about 36° C. Thus, it may be necessary to heat or cool the vessel containing the culture to ensure a constant culture temperature is maintained. The temperature may be used to control the doubling time ($t_d$), thus for a given culture process, the temperature may be different at different phases (i.e. the batch phase, fed batch phase and carbon feed phase).

The oxygen feed of the culture may be controlled. Oxygen may be supplied as air, enriched oxygen, pure oxygen or any combination thereof. Methods of monitoring oxygen concentration are known in the art. Oxygen may be delivered at a certain feed rate or may be delivered on demand by measuring the dissolved oxygen content of the culture and feeding accordingly with the intention of maintaining a constant dissolved oxygen content.

The rate of agitation or aeration may also be controlled. This ensures that nutrients and oxygen are transferred around the bioreactor in which the culture is contained. The relative velocity between the nutrient solution and the individual cell should be around 0.5 m/sec (e.g., 0.1, 0.2, 0.3, 0.4, 0.5, 0.6, 0.7, 0.8, 0.9 or 1.0 s).

As noted above, the pH of the culture may be controlled by the addition of acid or alkali. As pH will typically drop during culture, preferably alkali is added. Examples of suitable alkalis include NaOH and $NH_4OH$.

All of these variables may be controlled by the computer, computer-aided device or control algorithm as mentioned above. The alteration of these variables may be used to control the doubling time of the culture.

Polysaccharide Preparation

Methods for preparing capsular saccharides from bacteria are well known in the art, e.g., see references 15, 16, 17, etc. For GBS, the following methods may be used (see also Ref. 18). In particular, the methods of the invention for purifying a capsular polysaccharide may be used. As discussed above, these methods of the invention may include one or more of the following steps.

Starting Material

Generally, a small amount of capsular polysaccharide is released into the culture medium during bacterial growth, and so the starting material may thus be the supernatant from a centrifuged bacterial culture. More typically, however, the starting material will be prepared by treating the capsulated bacteria themselves (or material containing the bacterial peptidoglycan), such that the capsular saccharide is released. Cps can be released from bacteria by various methods, including chemical, physical or enzymatic treatment. Thus, an aqueous preparation of polysaccharide can be treated prior to the initial protein/nucleic acid precipitation reaction.

A typical chemical treatment is base extraction (Ref. 19) (e.g., using sodium hydroxide), which can cleave the phosphodiester linkage between the capsular saccharide and the peptidoglycan backbone. As base treatment de-N-acetylates the capsular saccharide, however, later re-N-acetylation may be necessary.

A typical enzymatic treatment involves the use of both mutanolysin and β-N-acetylglucosaminidase (Ref. 20). These act on the bacterial peptidoglycan to release the capsular saccharide for use with the invention, but also lead to release of the group-specific carbohydrate antigen. An alternative enzymatic treatment involves treatment with a type II phosphodiesterase (PDE2). PDE2 enzymes can cleave the same phosphates as sodium hydroxide (see above) and can release the capsular saccharide without cleaving the group-specific carbohydrate antigen and without de-N-acetylating the capsular saccharide, thereby simplifying downstream steps. PDE2 enzymes are therefore a preferred option for preparing capsular saccharides.

A preferred starting material for the process of the invention is de-N-acetylated capsular polysaccharide, which can be obtained by base extraction as described in U.S. Pat. No. 6,248,570 (Ref. 19). Another preferred starting material is the product of PDE2 treatment of *Streptococcus*. Such materials can be subjected to concentration (e.g., ultrafiltration) prior to precipitation as mentioned below.

The starting material may be subjected to alcoholic precipitation of contaminating proteins and/or nucleic acids, as described below.

Alcoholic Precipitation and Cation Exchange

The *Streptococcus* capsular saccharide obtained after culture will generally be impure and will be contaminated with bacterial nucleic acids and proteins. These contaminants can be removed by sequential overnight treatments with RNAse, DNAse and protease. However, as a preferred alternative, rather than remove these contaminants enzymatically, alcoholic precipitation can be used. If necessary (e.g., after base extraction), materials will usually be neutralized prior to the precipitation.

The alcohol used to precipitate contaminating nucleic acids and/or proteins is preferably a lower alcohol, such as methanol, ethanol, propan-1-ol, propan-2-ol, butan-1-ol, butan-2-ol, 2-methyl-propan-1-ol, 2-methyl-propan-2-ol, diols, etc. The selection of an appropriate alcohol can be tested empirically, without undue burden, but alcohols such as ethanol and isopropanol (propan-2-ol) are preferred, rather than alcohols such as phenol.

The alcohol is preferably added to the polysaccharide suspension to give a final alcohol concentration of between 10% and 50% (e.g., around 30%). The most useful concentrations are those which achieve adequate precipitation of contaminants without also precipitating the polysaccharide. The optimum final alcohol concentration may depend on the bacterial serotype from which the polysaccharide is obtained, and can be determined by routine experiments without undue burden. Precipitation of polysaccharides as ethanol concentrations >50% has been observed.

The alcohol may be added in pure form or may be added in a form diluted with a miscible solvent (e.g., water). Preferred solvent mixtures are ethanol:water mixtures, with a preferred ratio of between around 70:30 and around 95:5 (e.g., 75:25, 80:20, 85:15, 90:10).

The saccharide may also be treated with an aqueous metal cation. Monovalent and divalent metal cations are preferred, and divalent cations are particularly preferred, such as Mg, Mn, Ca, etc., as they are more efficient at complex formation. Calcium ions are particularly useful, and so the alcohol mixture preferably includes soluble calcium ion. These may be added to a saccharide/alcohol mixture in the form of calcium salts, either added as a solid or in an aqueous form. The calcium ions are preferably provided by the use of calcium chloride.

The calcium ions are preferably present at a final concentration of between 10 and 500 mM (e.g., about 0.1 M). The optimum final Ca concentration may depend on the *Streptococcus* strain and serotype from which the polysaccharide is obtained, and can be determined by routine experiments without undue burden.

After alcoholic precipitation of contaminating proteins and/or nucleic acids, the capsular polysaccharide is left in solution. The precipitated material can be separated from the polysaccharide by any suitable means, such as by centrifugation. The supernatant can be subjected to microfiltration, and in particular to dead-end filtration (perpendicular filtration) in order to remove particles that may clog filters in later steps (e.g., precipitated particles with a diameter greater than 0.22 μm). As an alternative to dead-end filtration, tangential microfiltration can be used. For example, tangential microfiltration using a 0.2 μm cellulose membrane may be used. The step of tangential microfiltration is typically followed by filtration using a 0.45/0.2 μm filter.

Diafiltration

A step of diafiltration may be used. For example, if the method includes the alcoholic precipitation and cation exchange described above, then this step may be carried out after the precipitation of proteins and/or nucleic acids. Similarly, if the method includes the step of cationic detergent treatment described below, then this diafiltration step may be carried out before the detergent-mediated precipitation. In the methods of the invention that include filtration using an adherent filter, e.g. filtration with a protein adherent filter, this diafiltration step may be carried out before that filtration. Typically, a step of diafiltration is used after the precipitation of proteins and/or nucleic acids, and before the detergent-mediated precipitation or filtration using an adherent filter, e.g. a protein adherent filter.

The diafiltration step is particularly advantageous if base extraction or phosphodiesterase was used for release of the capsular saccharide, as the group specific saccharide will also have been hydrolyzed, to give fragments much smaller than the intact capsular saccharide. These small fragments can be removed by the diafiltration step.

Tangential flow diafiltration is typical. The filtration membrane should thus be one that allows passage of hydrolysis products of the group-specific antigen while retaining the capsular polysaccharide. A cut-off in the range 10 kDa-30 kDa is typical. Smaller cut-off sizes can be used, as the hydrolysis fragments of the group-specific antigen are generally around 1 kDa (5-mer, 8-mer and 11-mer saccharides), but the higher cut-off advantageously allows removal of other contaminants without leading to loss of the capsular saccharide.

At least 5 cycles of tangential flow diafiltration are usually performed, e.g., 6, 7, 8, 9, 10, 11 or more. Typically, 2 cycles of tangential flow diafiltration are performed. Between the first and second cycles, the retentate of the first diafiltration cycle may be treated with an acetic acid/sodium acetate solution. The resultant suspension may be filtered to remove precipitate, e.g. using a 0.45 μm filter. The suspension may also, or in addition, be filtered using a 0.2 μm filter.

The diafiltration may be followed by further filtration using a 0.45/0.2 μm filter.

Cationic Detergent Treatment

Many techniques for precipitating soluble polysaccharides are known in the art. The saccharide may optionally be precipitated using one or more cationic detergents, though preferred embodiments of the purification will exclude detergent precipitation. Treating a mixture of the capsular saccharide and group-specific saccharide with a cationic detergent leads to preferential precipitation of the capsular saccharide, thereby advantageously and conveniently minimizing contamination by the group-specific saccharide.

Particularly preferred detergents for use in the process of the invention are tetrabutylammonia and cetyltrimethylammonia salts (e.g., the bromide salts). Cetyltrimethylammonia bromide (CTAB) is particularly preferred (Ref. 21). CTAB is also known as hexadecyltrimethylammonia bromide, cetrimonium bromide, Cetavlon and Centimide. Other detergents include hexadimethrine bromide and myristyltrimethylammonia salts.

The detergent-mediated precipitation step is preferably selective for the capsular polysaccharide.

Advantageously, the optional detergent precipitation may use a detergent such as CTAB that interacts with sialic acid residues in the saccharide, e.g., via carboxyl groups in the sialic acid. The detergent will thus preferentially precipitate the sialic acid-containing capsular saccharides, and particularly longer saccharides within a mixed population, thus minimizing contamination by saccharides whose antigenically-important sialic acids may have been damaged in earlier treatment steps.

Re-Solubilization

When an optional detergent precipitation step is used, the polysaccharide (typically in the form of a complex with the cationic detergent) can be re-solubilized, either in aqueous medium or in alcoholic medium. For aqueous re-solubilization, the CTA⁻ cation in the precipitate will generally be replaced by a metal cation; for alcoholic re-solubilization, the CTA⁻ cation will generally be retained. The choice of aqueous or alcoholic re-solubilization may depend on the GBS serotype from which the polysaccharide is obtained, and on any contaminants still present at this stage. For example, pigments are sometimes present in the precipitated pellet, and these can effectively be removed by alcoholic re-solubilization followed by carbon filtration.

A typical aqueous medium for re-solubilization will include a metal cation. Monovalent and divalent metal cations are preferred, and divalent cations are particularly preferred, such as Mn, Ca, etc. Calcium ions are particularly useful, and so re-solubilization preferably uses Ca, provided by the use of calcium chloride. A Ca concentration of between 10 and 500 mM (e.g., about 0.1M) is preferred. The optimum final Ca concentration may depend on the *Streptococcus* serotype from which the polysaccharide is obtained, and can be determined by routine experiments without undue burden.

A typical alcoholic medium for re-solubilization is based on ethanol. The same alcohols used for precipitation of nucleic acids and/or proteins can be used, but the concentration required for precipitation of the capsular saccharide will generally be higher, e.g., the alcohol is preferably added to give a final alcohol concentration of between 70% and 95% (e.g., around 70%, 75%, 80%, 85%, 90% or 95%). The optimum final alcohol concentration may depend on the *Streptococcus* serotype from which the polysaccharide is obtained. To achieve the high alcohol concentrations then it is preferred to add alcohol with a low water content, e.g., 96% ethanol.

Re-solubilization will typically occur at room temperature. Acidic conditions are preferably avoided, and re-solubilization will typically take place at about pH 7.

The re-solubilized material is highly purified relative to the pre-precipitation suspension.

One preferred method for preparing the saccharides involves polysaccharide precipitation followed by solubilization of the precipitated polysaccharide using a lower alcohol as described above. After re-solubilization, the polysaccharide may be further treated to remove contaminants.

This is particularly important in situations where even minor contamination is not acceptable (e.g., for human vaccine production). This will typically involve one or more steps of filtration, e.g., depth filtration, filtration through activated carbon may be used, size filtration and/or ultrafiltration. Once filtered to remove contaminants, the polysaccharide may be precipitated for further treatment and/or processing. This can be conveniently achieved by exchanging cations (e.g., by the addition of calcium or sodium salts).

Filtration with an Adherent Filter

In preferred embodiments, the purification of the capsular polysaccharides will further include a step whereby protein and/or DNA contaminants are removed by filtration with a filter, e.g. a protein adherent filter, to which protein and/or DNA adheres, but to which the capsular polysaccharide does not adhere or only weakly adheres. A preferred example of such filter is a carbon filter. Suitable adherent filters are described above.

The filtration using an adherent filter may be followed by further filtration using a 0.45/0.2 μm filter.

Re—N-acetylation

A step of re-N-acetylation may be carried out, for example after a step of filtration using an adherent filter or, if present, further filtration step. Re—N-acetylation may be advantageous if sialic acid residues in the GBS capsular saccharides have been de-N-acetylated, for example during the base treatment described above. Controlled re-N-acetylation can conveniently be performed using a reagent such as acetic anhydride $(CH_3CO)_2O$, e.g. in 5% ammonium bicarbonate [Wessels et al. (1989) *Infect Immun* 57:1089-94].

Further Diafiltration

A further step of diafiltration may be carried out, for example after re-N-acetylation. The diafiltration may be carried out as described above in the section entitled "Diafiltration".

The diafiltration may be followed by further filtration using a 0.45/0.2 μm filter.

Final Material

The polysaccharide is preferably finally prepared as a dried powder, ready for conjugation.

Conjugate Preparation

After culture of bacteria and preparation of capsular polysaccharides, the saccharide are conjugated to carrier protein(s). In general, covalent conjugation of saccharides to carriers enhances the immunogenicity of saccharides as it converts them from T-independent antigens to T-dependent antigens, thus allowing priming for immunological memory. Conjugation is particularly useful for pediatric vaccines (e.g., ref. 22) and is a well known technique (e.g., reviewed in refs. 23 to 31)

Preferred carrier proteins are bacterial toxins or toxoids, such as diphtheria toxoid or tetanus toxoid. The CRM1 97 mutant of diphtheria toxin (Refs 32-34) is a particularly preferred carrier for, as is a diphtheria toxoid. Other suitable carrier proteins include the N meningitidis outer membrane protein (Ref. 35), synthetic peptides (Refs. 36,37), heat shock proteins (Refs. 38,39), pertussis proteins (Refs. 40,41), cytokines (Ref. 42), lymphokines (Ref. 42), hormones (Ref. 42), growth factors (Ref. 42), artificial proteins comprising multiple human CD4 T cell epitopes from various pathogen-derived antigens (Ref. 43) such as N19 (Ref. 44), protein D from *H. influenzae* (Ref 45,46), pneumococcal surface protein PspA (Ref. 47), pneumolysin (Ref 48), iron-uptake proteins (Ref. 49), toxin A or B from *C. difficile* (Ref 50), a GBS protein (see below) (Ref 51), etc. Attachment to the carrier is preferably via a —NH2 group, e.g., in the side chain of a lysine residue in a carrier protein, or of an arginine residue. Where a saccharide has a free aldehyde group then this can react with an amine in the carrier to form a conjugate by reductive amination. Such a conjugate may be created using reductive amination involving an oxidized galactose in the saccharide (from which an aldehyde is formed) and an amine in the carrier or in the linker. Attachment may also be via a —SH group, e.g., in the side chain of a cysteine residue.

It is possible to use more than one carrier protein, e.g., to reduce the risk of carrier suppression. Thus different carrier proteins can be used for different *Streptococcus* strains or serotypes, e.g., GBS serotype Ia saccharides might be conjugated to CRM197 while serotype 1b saccharides might be conjugated to tetanus toxoid. It is also possible to use more than one carrier protein for a particular saccharide antigen, e.g., serotype III saccharides might be in two groups, with some conjugated to CRM197 and others conjugated to tetanus toxoid. In general, however, it is preferred to use the same carrier protein for all saccharides.

A single carrier protein might carry more than one saccharide antigen (Refs. 52, 53). For example, a single carrier protein might have conjugated to it saccharides from serotypes Ia and Ib. To achieve this goal, different saccharides can be mixed prior to the conjugation reaction. In general, however, it is preferred to have separate conjugates for each serogroup, with the different saccharides being mixed after conjugation The separate conjugates may be based on the same carrier.

Conjugates with a saccharide:protein ratio (w/w) of between excess protein (e.g., 1:5) and excess saccharide (e.g., 5:1) are preferred. Ratios between 1:2 and 5:1 ire' preferred, as are ratios between 1:1.25 and 1:2.5. Ratios between 1:1 and 4:1 are also preferred. With longer saccharide chains, a weight excess of saccharide is typical. In general, the invention provides a conjugate, wherein the conjugate comprises a *Streptococcus*, preferably a *S. agalactiae* capsular saccharide moiety joined to a carrier, wherein the weight ratio of saccharide: carrier is at least 2:1.

Compositions may include a small amount of free carrier. When a given carrier protein is present in both free and conjugated form in a composition of the invention, the unconjugated form is preferably no more than 5% of the total amount of the carrier protein in the composition as a whole, and more preferably present at less than 2% by weight.

Any suitable conjugation reaction can be used, with any suitable linker where necessary.

The saccharide will typically be activated or functionalized prior to conjugation. Activation may involve, for example, cyanylating reagents such as CDAP (e.g., 1.-cyano-4-dimethylamino pyridinium tetrafluoroborate (Refs. 54, 55, etc.)). Other suitable techniques use carbodiimides, hydrazides, active esters, norborane, p-nitrobenzoic acid, N-hydroxysuccinimide, S—NHS, EDC, and TSTU (see also the introduction to reference 29).

Linkages via a linker group may be made using any known procedure, for example, the procedures described in references 56 and 57. One type of linkage involves reductive amination of the polysaccharide, coupling the resulting amino group with one end of an adipic acid linker group, and then coupling a protein to the other end of the adipic acid linker group (Refs. 27, 58, 59). Other linkers include B-propionamido (Ref. 60), nitrophenyl-ethylamine (Ref. 61), haloacyl halides (Ref. 62), glycosidic linkages (Ref. 63), 6-aminocaproic acid (Ref. 64), ADH (Ref. 65), C4 to C12 moieties (Ref. 66), etc. As an alternative to using a linker, direct linkage can be used. Direct linkages to the protein may comprise oxidation of the polysaccharide followed by reductive amination with the protein, as described in, for example, references 67 and 68.

A process involving the introduction of amino groups into the saccharide (e.g., by replacing terminal =O groups with —NH2) followed by derivatization with an adipic diester (e.g., adipic acid N-hydroxysuccinimido diester) and reaction with carrier protein is preferred. Another preferred reaction uses CDAP activation with a protein D carrier.

After conjugation, free and conjugated saccharides can be separated. There are many suitable methods, including hydrophobic chromatography, tangential ultrafiltration, diafiltration, etc. (see also refs. 69 & 70, etc.).

Where the composition of the invention includes a depolymerized oligosaccharide, it is preferred that depolymerization precedes conjugation, e.g., is before activation of the saccharide.

In one preferred conjugation method, a saccharide is reacted with adipic acid dihydrazide. For serogroup A, carbodiimide may also be added at this stage. After a reaction period, sodium cyanoborohydride is added. Derivatized saccharide can then be prepared, e.g., by ultrafiltration.

The derivatized saccharide is then mixed with carrier protein (e.g., with a diphtheria toxoid), and carbodiimide is added. After a reaction period, the conjugate can be recovered.

Other Steps

As well as including the steps described above, methods of the invention may include further steps. For example, the methods may include a step of depolymerization of the capsular saccharides, after they are prepared from the bacteria but before conjugation. Depolymerization reduces the chain length of the saccharides and may not be good for GBS. For *Streptococcus*, especially GBS, longer saccharides tend to be more immunogenic than shorter ones (Ref. 71).

After conjugation, the level of unconjugated carrier protein may be measured. One way of making this measurement involves capillary electrophoresis (Ref. 72) (e.g., in free solution), or micellar electrokinetic chromatography (Ref. 73).

After conjugation, the level of unconjugated saccharide may be measured. One way of making this measurement involves HPAEC-PAD (Ref. 69).

After conjugation, a step of separating conjugated saccharide from unconjugated saccharide may be used. One way of separating these saccharides is to use a method that selectively precipitates one component. Selective precipitation of conjugated saccharide is preferred, to leave unconjugated saccharide in solution, e.g., by a deoxycholate treatment (Ref. 69).

After conjugation, a step of measuring the molecular size and/or molar mass of a conjugate may be carried out. In particular, distributions may be measured. One way of making these measurements involves size exclusion chromatography with detection by multiangle light scattering photometry and differential refractometry (SEC-MALS/RI) (Ref. 74).

Conjugate Combinations

Individual conjugates can be prepared as described above, for any Pneumococcus serogroup.

Preferably conjugates are prepared for one or more of serogroups 1, 3, 4, 5, 6B, 7F, 9V, 14, 18C, 19F, and 23F. The individual conjugates can then be mixed, in order to provide a polyvalent mixture.

It is also possible to mix a selected number of conjugates to provide a bivalent, trivalent, tetravalent, 5-valent, 6-valent, 7-valent or 11-valent mixture (e.g., to mix 1+3+4+5+6B+7F+9V+14+1 8C+19F+23F, 4+6B+9V+14+ 18C+19F+23F or 1+4+6B+9V+14+1 8C+19F+23F, etc.).

For GBS, conjugates are preferably prepared from one or more of serogroups Ia, Ib or III.

Conjugates may be mixed by adding them individually to a buffered solution. A preferred solution is phosphate buffered physiological saline (final concentration 10 mM sodium phosphate). A preferred concentration of each conjugate (measured as saccharide) in the final mixture is between 1 and 20 µg/ml e.g., between 5 and 15 µg/ml, such as around 8 µg/ml. An optional aluminum salt adjuvant may be added at this stage (e.g., to give a final $Al^{3+}$ concentration of between 0.4 and 0.5 mg/ml).

After mixing, the mixed conjugates can be sterile filtered.

Pharmaceutical Compositions

Conjugates prepared by methods of the invention can be combined with pharmaceutically acceptable carriers. Such carriers include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in reference 75.

Compositions may include an antimicrobial, particularly if packaged in a multiple dose format.

Compositions may comprise detergent, e.g., a Tween (polysorbate), such as TWEEN 80™. Detergents are generally present at low levels, (e.g., >0.01%).

Compositions may include sodium salts (e.g., sodium chloride) to give tonicity. A concentration of 10±2 mg/ml NaCl is typical.

Compositions will generally include a buffer. A phosphate buffer is typical.

Compositions may comprise a sugar alcohol (e.g., mannitol) or a disaccharide (e.g., sucrose or trehalose) e.g., at around 15-30 mg/ml (e.g., 25 mg/ml), particularly if they are to be lyophilized or if they include material which has been reconstituted from lyophilized material. The pH of a composition for lyophilization may be adjusted to around 6.1 prior to lyophilization.

Conjugates may be administered in conjunction with other immunoregulatory agents. In particular, compositions will usually include a vaccine adjuvant. Adjuvants which may be used in compositions of the invention include, but are not limited to:

A. Mineral-Containing Compositions

Mineral containing compositions suitable for use as adjuvants in the invention include mineral salts, such as aluminum salts and calcium salts (or mixtures thereof). The invention includes mineral salts such as hydroxides (e.g., oxyhydroxides), phosphates (e.g., hydroxyphosphates, orthophosphates), sulphates, etc. (Ref. e.g., see chapters 8 & 9 of ref. 76), or mixtures of different mineral compounds, with the compounds taking any suitable form (e.g., gel, crystalline, amorphous, etc.), and with adsorption being preferred. The mineral containing compositions may also be formulated as a particle of metal salt (Ref. 77).

Aluminum phosphates are particularly preferred, particularly in compositions which include a *H. influenzae* saccharide antigen, and a typical adjuvant is amorphous aluminum hydroxyphosphate with $PO_4/Al$ molar ratio between 0.84 and 0.92, included at 0.6 mg $Al^{+3}$/ml.

Adsorption with a low dose of aluminum phosphate may be used e.g., between 50 and 100 μg $Al^{3+}$ per conjugate per dose. Where there is more than one conjugate in a composition, not all conjugates need to be adsorbed.

Calcium salts include calcium phosphate (e.g. the "CAP" particles disclosed in ref. 258. Aluminum salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt [77]. Aluminum salt adjuvants are described in more detail below.

The adjuvants known as aluminum hydroxide and aluminum phosphate may be used. These names are conventional, but are used for convenience only, as neither is a precise description of the actual chemical compound which is present (e.g. see chapter 9 of reference 76). The invention can use any of the "hydroxide" or "phosphate" adjuvants that are in general use as adjuvants.

The adjuvants known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide $Al(OH)_3$, by infrared (IR) spectroscopy, in particular by the presence of an adsorption band at 1070 $cm^{-1}$ and a strong shoulder at 3090-3100 $cm^{-1}$ [chapter 9 of ref. 76]. The degree of crystallinity of an aluminium hydroxide adjuvant is reflected by the width of the diffraction band at half height (WHH), with poorly crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg $Al^{+++}$ at pH 7.4 have been reported for aluminium hydroxide adjuvants.

The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Hydroxyphosphates generally have a $PO_4/Al$ molar ratio between 0.3 and 1.2. Hydroxyphosphates can be distinguished from strict $AlPO_4$ by the presence of hydroxyl groups. For example, an IR spectrum band at 3164 $cm^{-1}$ (e.g. when heated to 200° C.) indicates the presence of structural hydroxyls [ch. 9 of ref. 76].

The $PO_4/Al^{3+}$ molar ratio of an aluminium phosphate adjuvant will generally be between 0.3 and 1.2, preferably between 0.8 and 1.2, and more preferably 0.95+0.1. The aluminium phosphate will generally be amorphous, particularly for hydroxyphosphate salts. A typical adjuvant is amorphous aluminium hydroxyphosphate with $PO_4/Al$ molar ratio between 0.84 and 0.92, included at 0.6 mg $Al^{3+}$/ml. The aluminium phosphate will generally be particulate (e.g. plate like morphology as seen in transmission electron micrographs). Typical diameters of the particles are in the range 0.5-20μm (e.g. about 5-10 μm) after any antigen adsorption. Adsorptive capacities of between 0.7-1.5 mg protein per mg $Al^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

Suspensions of aluminium salts used to prepare compositions of the invention may contain a buffer (e.g. a phosphate or a histidine or a Tris buffer), but this is not always necessary. The suspensions are preferably sterile and pyrogen free. A suspension may include free aqueous phosphate ions e.g. present at a concentration between 1.0 and 20 mM, preferably between 5 and 15 mM, and more preferably about 10 mM. The suspensions may also comprise sodium chloride.

The invention can use a mixture of both an aluminium hydroxide and an aluminium phosphate, as in DARONRIX™. In this case there may be more aluminium phosphate than hydroxide e.g. a weight ratio of at least 2:1 e.g. >5:1, >6:1, >7:1, >8:1, >9:1, etc.

The concentration of Al$^{+++}$ in a composition for administration to a patient is preferably less than 10 mg/ml e.g. <5 mg/ml, <4 mg/ml, <3 mg/ml, <2 mg/ml, <1 mg/ml, etc. A preferred range is between 0.3 and 1 mg/ml. A maximum of 0.85 mg/dose is preferred.

B. Oil Emulsions

Oil emulsion compositions suitable for use as adjuvants in the invention include squalene-water emulsions, such as MF59 (Ref. Chapter 10 of ref. 76; see also ref. 78) (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

The oil droplets in the emulsion are generally less than 5 μm in diameter, and may even have a sub-micron diameter, with these small sizes being achieved with a microfluidiser to provide stable emulsions. Droplets with a size less than 220 nm are preferred as they can be subjected to filter sterilization.

C. Saponin formulations (Ref: chapter 22 of ref 76)

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as STIMULON™.

Saponin compositions have been purified using HPLC and RP-HIPLC. Specific purified fractions using these techniques have been identified, including QS7, QS17, QS1 8, QS21, QH-A, QH-B and QH-C. Preferably, the saponin is QS21. A method of production of QS21 is disclosed in ref. 79. Saponin formulations may also comprise a sterol, such as cholesterol (Ref. 80).

Combinations of saponins and cholesterols can be used to form unique particles called immunostimulating complexes (ISCOMs) (Ref. chapter 23 of ref. 76). ISCOMs typically also include a phospholipid such as phosphatidylethanolamine or phosphatidyiclioline. Any known saponin can be used in ISCOMs. Preferably, the ISCOM includes one or more of QuilA, QHA & QHC. ISCOMs are further described in refs. 80-82. Optionally, the ISCOMS may be devoid of additional detergent (Ref. 83).

A review of the development of saponin based adjuvants can be found in refs. 84 & 85.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 86-91. Virosomes are discussed further in, for example, ref. 92.

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 93. Such "small particles" of 3dMPL are small enough to be sterile filtered through a 0.22 μm membrane (Ref. 93). Other non-toxic LPS derivatives include monophosphoryl lipid A mimics, such as aminoalkyl glucosaminide phosphate derivatives e.g., RC-529 (Ref. 94,95).

Lipid A derivatives include derivatives of lipid A from *Escherichia coli* such as OM-174. OM-174 is described for example in refs. 96 & 97.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 98, 99 and 100 disclose possible analog substitutions, e.g., replacement of guanosine with 2'-deoxy-7-deazaguanosine. The adjuvant effect of CpG oligonucleotides is further discussed in refs. 101-106.

The CpG sequence may be directed to TLR9, such as the motif GTCGTT or TTCGTT (Ref. 107). The CpG sequence may be specific for inducing a Th1 immune response, such as a CpG-A ODN, or it may be more specific for inducing a B cell response, such a CpG-B ODN. CpG-A and CpG-B ODNs are discussed in refs. 108-110. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers." See, for example, refs. 107 & 111-113.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 114 and as parenteral adjuvants in ref. 115. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 116-123. Numerical reference for amino acid substitutions is preferably based on the alignments of the A and B subunits of ADP-ribosylating toxins set forth in ref. 124, specifically incorporated herein by reference in its entirety.

F. Human Immunomodulators

Human immunomodulators suitable for use as adjuvants in the invention include cytokines, such as interleukins (e.g., IL-1, IL-2, 11-4, IL-5, IL-6, IL-7, IL-12 (Ref. 125), etc.) (Ref. 126), interferons (e.g., interferon-γ), macrophage colony stimulating factor, and tumor necrosis factor. A preferred immunomodulator is IL-12.

G. Bioadhesives and Mucoadhesives

Bioadhesives and mucoadhesives may also be used as adjuvants in the invention. Suitable bioadhesives include esterified hyaluronic acid microspheres (Ref. 127) or mucoadhesive such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention (Ref. 128).

H. Microparticles

Microparticles may also be used as adjuvants in the invention. Microparticles (i.e., a particle of ~100 nm to ~150 μm in diameter, more preferably ~200 nm to ~33 μm in diameter, and most preferably ~500 nm to ..10 μm in diameter) formed from materials that are biodegradable and non-toxic (e.g., a poly(α-hydroxy acid), a polyhydroxybutyric acid, a polyorthoester, a polyarthydride, a polycaprolactone, etc.), with poly(lactide-co-glycolide) are preferred, optionally treated to have a negatively charged surface (e.g., with SDS) or a positively-charged surface (e.g., with a cationic detergent, such as CTAB).

I. Liposomes (Chapters 13 & 14 of ref 76)

Examples of liposome formulations suitable for use as adjuvants are described in refs. 129-131.

J. Polyoxyethylene Ether and Polyoxyethylene Ester Formulations

Adjuvants suitable for use in the invention include polyoxyethylene ethers and polyoxyethylene esters (Ref. 132). Such formulations further include polyoxyethylene sorbitan ester surfactants in combination with an octoxynol (Ref. 133) as well as polyoxyethylene alkyl ethers or ester surfactants in combination with at least one additional non-ionic surfactant such as an octoxynol (Ref. 134). Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 135 and 136.

L. Muramyl peptides

Examples of muramyl peptides suitable for use as adjuvants in the invention include N-acetylmuramy-L-threonyl-D-isoglutamine (thr-MDP), N-acetylmuramyl-L-alanyl-D-isoglutamine (nor-MDP), and N-acetylmuramyl-L-alanyl-D-isoglutamyl-L-alanine-2-(1'-2'-dipalmitoyl-sn-glycero-3 hydroxyphosphoryloxy)-ethylamine MTP-PE).

M. Imidazoqutholone Compounds.

Examples of imidazoquinolone compounds suitable for use adjuvants in the invention include IMIQUAMOD™ and its homologues (e.g., RESIQUIMOD 3M™), described further in refs. 137 and 138.

The invention may also comprise combinations of aspects of one or more of the adjuvants identified above. For example, the following adjuvant compositions may be used in the invention: (1) a saponin and an oil-in-water emulsion (Ref. 139); (2) a saponin (e.g., QS21)+a non-toxic LPS derivative (e.g., 3dMPL) (Ref. 140); (3) a saponin (e.g., QS21)+a non-toxic LPS derivative (e.g., 3dMPL)+a cholesterol; (4) a saponin (e.g., QS2I)+3dMPL+IL-12 (optionally +a sterol) (Ref. 141); (5) combinations of 3dMPL with, for example, QS21 and/or oil-in-water emulsions (Ref. 142); (6) SAF, containing 10% squalane, 0.4% TWEEN 80™, 5% pluronic-block polymer L121, and thr-MDP either microfluidized into a submicron emulsion or vortexed to generate a larger particle size emulsion. (7) RIBI™ adjuvant system (RAS), (Ribi Immunochem) containing 2% squalene, 0.2 TWEEN 80™, and one more bacterial cell wall components from the group consisting of monophosphorylipid A (MPL), trehalose dimycolate (TDM), and cell wall skeleton (CWS); preferably MPL+CWS (DETOX™); and (8) one or more mineral salts (such as an aluminum salt)+a non-toxic derivative of LPS (such as 3dMPL).

Other substances that act as immunostimulating agents are disclosed in chapter 7 of ref. 76.

The use of an aluminum hydroxide and/or aluminum phosphate adjuvant is particularly preferred, and antigens are generally adsorbed to these salts. Calcium phosphate is another preferred adjuvant.

The composition may be sterile and/or pyrogen-free. Compositions may be isotonic with respect to humans.

Compositions may be presented in vials, or they may be presented in ready-filled syringes. The syringes may be supplied with or without needles. A syringe will include a single dose of the composition, whereas a vial may include a single dose or multiple doses. Injectable compositions will usually be liquid solutions or suspensions. Alternatively, they may be presented in solid form (e.g., freeze-dried) for solution or suspension in liquid vehicles prior to injection.

Compositions may be packaged in unit dose form or in multiple dose form. For multiple dose forms, vials are preferred to pre-filled syringes. Effective dosage volumes can be routinely established, but a typical human dose of the composition for injection has a volume of 0.5 ml.

Where a composition is to be prepared extemporaneously prior to use (e.g., where a component is presented in lyophilized form) and is presented as a kit, the kit may comprise two vials, or it may comprise one ready-filled syringe and one vial, with the contents of the syringe being used to reactivate the contents of the vial prior to injection.

Immunogenic compositions used as vaccines comprise an immunologically effective amount of antigen(s), as well as any other components, as needed. By immunologically effective amount, it is meant that the administration of that amount to an individual, either in a single dose or as part of a series, is effective for treatment or prevention. This amount varies depending upon the health and physical condition of the individual to be treated, age, the taxonomic group of individual to be treated (e.g., non-human primate, primate, etc.), the capacity of the individuals immune system to synthesize antibodies, the degree of protection desired, the formulation of the vaccine, the treating doctor's assessment of the medical situation, and other relevant factors. It is expected that the amount will fall in a relatively broad range that can be determined through routine trials, and a typical quantity of each streptococcal conjugate in between 1 μg and 20 μg per conjugate (measured as saccharide).

Thus the invention provides a method for preparing a pharmaceutical composition, comprising the steps of: (a) preparing a conjugate as described above; (b) mixing the conjugate with one or more pharmaceutically acceptable carriers.

The invention further provides a method for preparing a pharmaceutical product, comprising the steps of: (a) preparing a conjugate as described above; (b) mixing the conjugate with one or more pharmaceutically acceptable carriers; and (c) packaging the conjugate/carrier mixture into a container, such as a vial or a syringe, to give a pharmaceutical product. Insertion into a syringe may be performed in a factory or in a surgery.

The invention also provides a method for preparing a pharmaceutical composition from a saccharide-protein conjugate, comprising the step of admixing the conjugate with a pharmaceutically acceptable carrier, wherein the conjugate has been prepared by a process conjugation method as described above. The conjugation method and the admixing step can be performed at very different times by different people in different places (e.g., in different countries).

The invention also provides a method for packaging a saccharide-protein conjugate into a pharmaceutical product, wherein the conjugate has been prepared by a process conjugation method as described above. The conjugation method and the packaging step can be performed at very different times by different people in different places (e.g., in different countries).

Pharmaceutical Uses

The invention also provides a method of treating a patient, comprising administering the composition to the patient. The patient may either be at risk from the disease themselves or may be a pregnant woman (maternal immunization). The patient is preferably a human. The human can be of any age e.g., <2 years old, from 2-11 years old, from 11-55 years old, >55 years old, etc.

The invention also provides the composition for use in therapy. The invention also provides the use of the composition in the manufacture of a medicament for the treatment of disease. Preferably the disease is influenza or pneumonia.

Compositions will generally be administered directly to a patient. Direct delivery may be accomplished by parenteral injection (e.g., transcutaneously, subcutaneously, intraperitoneally, intravenously, intramuscularly, or to the interstitial space of a tissue), or by rectal, oral, vaginal, optical, transdermal, intranasal, ocular, aural, pulmonary or other mucosal administration. Intramuscular administration (e.g., to the thigh or the upper arm) is preferred. Injection may be via a needle (e.g., a hypodermic needle), but needle-free injection may alternatively be used. A typical intramuscular dose is 0.5 ml.

The invention may be used to elicit systemic and/or mucosal immunity.

Dosage treatment can be a single dose schedule or a multiple dose schedule. Multiple doses may be used in a primary immunization schedule and/or in a booster immunization schedule. A primary dose schedule may be followed by a booster dose schedule. Suitable timing between priming doses (e.g., between 4-16 weeks), and between priming and boosting, can be routinely determined.

Bacterial infections affect various areas of the body and so compositions may be prepared in various forms. For example, the compositions may be prepared as injectables, either as liquid solutions or suspensions. Solid forms suitable for solution in, or suspension in, liquid vehicles prior to injection can also be prepared (e.g., a lyophilized composition). The composition may be prepared for topical administration, e.g., as an ointment, cream or powder. The composition may be prepared for oral administration, e.g., as a tablet or capsule, or as a syrup (optionally flavored). The composition may be prepared for pulmonary administration, e.g., as an inhaler, using a fine powder or a spray. The composition may be prepared as a suppository or pessary.

The composition may be prepared for nasal, aural or ocular administration, e.g., as spray, drops, gel or powder (e.g., refs 143 & 144). Injectable compositions are preferred.

Further Antigenic Components of Compositions of the Invention

The methods of the invention may also comprise the steps of mixing a streptococcal conjugate with one or more of the following other antigens:

a saccharide antigen from *Haemophilus influenzae* B (e.g., chapter 14 of ref. 145).

a purified protein antigen from serogroup B of *Neisseria meningitidis*.

an outer membrane preparation from serogroup B of *Neisseria meningitidis*.

an antigen from hepatitis A virus, such as inactivated virus (e.g., 46, 147).

an antigen from hepatitis B virus, such as the surface and/or core, antigens (e.g., 147, 148).

a diphtheria antigen, such as a diphtheria toxoid (e.g., chapter 13 of ref. 145)

a tetanus antigen, such as a tetanus toxoid (e.g., chapter 27 of ref. 145).

an antigen from *Bordetella pertussis*, such as pertussis holotoxin (PT) and filamentous hemagglutinin (FHA) from *B. pertussis*, optionally also in combination with pertactin and/or agglutinogens 2 and 3 (e.g., refs. 149 & 150; chapter 21 of ref. 145).

polio antigen(s) (e.g., 151, 152) such as IPV (chapter 24 of ref. 145).

measles, mumps and/or rubella antigens (e.g., chapters 19, 20 & 26 of ref. 145).

influenza antigen(s) (e.g., chapter 17 of ref. 145), such as the haemagglutinin and/or neuraminidase surface proteins.

an antigen from *Moraxella catarrhalis* (e.g., 153).

a protein antigen from *Streptococcus agalactiae* (group B streptococcus) (e.g., 154, 155).

an antigen from *Streptococcus pyogenes* (group A streptococcus) (e.g., 155, 156, 157).

an antigen from *Staphylococcus aureus* (e.g., 158).

The composition may comprise one or more of these further antigens.

Toxic protein antigens may be detoxified where necessary (e.g., detoxification of pertussis toxin by chemical and/or genetic means (Ref. 150)).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Antigens in the composition will typically be present at a concentration of at least 1 g/ml each. In general, the concentration of any given antigen will be sufficient to elicit an immune response against that antigen.

As an alternative to using proteins antigens in the immunogenic compositions of the invention, nucleic acid (preferably DNA, e.g., in the form of a plasmid) encoding the antigen may be used.

Antigens are preferably adsorbed to an aluminum salt.

Preferred non-streptococcal antigens for inclusion in compositions are those which protect against *Haemophilus influenzae* type B (Hib); Typically this will be a Hib capsular saccharide antigen. Saccharide antigens from *H. influenzae* B are well known.

Advantageously, the Hib saccharide is covalently conjugated to a carrier protein, in order to enhance its immunogenicity, especially in children. The preparation of polysaccharide conjugates in general, and of the Hib capsular polysaccharide in particular, is well documented.

The invention may use any suitable Hib conjugate. Suitable carrier proteins are described above, and preferred carriers for Rib saccharides are CRM197 (HbOC), tetanus toxoid (PRP-T) and the outer membrane complex of *N. meningitidis* (PRP-OMP).

The saccharide moiety of the conjugate may be a polysaccharide (e.g., full-length polyribosylribitol phosphate (PRP)), but it is preferred to hydrolyze polysaccharides to form oligosaccharides (e.g., MW from ~1 to ~5 kDa).

A preferred conjugate comprises a Hib oligosaccharide covalently linked to CRM197 via an adipic acid linker (Ref. 159, 160). Tetanus toxoid is also a preferred carrier.

Administration of the Hib antigen preferably results in an anti-PRP antibody concentration of >0.15 µg/ml, and more preferably 1 µg/ml.

Where a composition includes a Hib saccharide antigen, it is preferred that it does not also include an aluminum hydroxide adjuvant. If the composition includes an aluminum phosphate adjuvant then the Hib antigen may be adsorbed to the adjuvant (Ref. 161) or it may be non-adsorbed (Ref. 162). Prevention of adsorption can be achieved by selecting the correct pH during antigen/adjuvant mixing, an adjuvant with an appropriate point of zero charge, and an appropriate order of mixing for the various different antigens in a composition (Ref. 163).

Compositions of the invention may comprise more than one Hib antigen. Hib antigens may be lyophilized, e.g., for reconstitution by meningococcal compositions. Thus a Hib antigen may be packaged separately from meningococcal conjugates, or may be admixed with them.

Other non-streptococcal antigens for including in compositions of the invention are those derived from a sexually transmitted disease (STD). Such antigens may provide for prophylaxis or therapy for STDs such as *Chlamydia*, genital herpes, hepatitis (such as HCV), genital warts, gonorrhoeae, syphilis and/or chancroid (Ref. 164). Antigens may be derived from one or more viral or bacterial STDs. Viral STD antigens for use in the invention may be derived from, for example, HIV, herpes simplex virus (HSV-1 and HSV-2), human papillomavirus (HPV), and/or hepatitis (HCV). Bacterial STD antigens for use in the invention may be derived from, for example, *Neisseria gonorrhoeae*, *Chlamydia trachomatis*, *Treponema pallidum*, *Haemophilus ducreyi* or *E. coli*.

The practice of the present invention will employ, unless otherwise indicated, conventional techniques of molecular biology, microbiology, recombinant DNA, and immunology, which are within the skill of the art. Such techniques are explained fully in the literature. See, e.g., *DNA Cloning*, Volumes I and II (D. N Glover ed. 1985); *Oligonucleotide Synthesis* (MT Gait ed, 1984); *Nucleic Acid Hybridization* (B. D. Hames & S T Higgins eds. 1984); *Transcription and Translation* (B. D. Hames & S T Higgins eds. 1984); *Animal Cell Culture* (R. I. Freshney ed. 1986); *Immobilized Cells and Enzymes* (IRL Press, 1986); B. Perbal, *A Practical Guide to Molecular Cloning* (1984); the Methods in Enzymology series (Academic Press, Inc.), especially volumes 154 & 155; *Gene Transfer Vectors for Mammalian Cells* (J. H. Miller and M. P. Calos eds. 1987, Cold Spring Harbor Laboratory); Mayer and Walker, eds. (1987), *Immunochemical Methods in Cell and Molecular Biology* (Academic Press, London); Scopes, (1987) *Protein Purification: Principles and Practice*, Second Edition (Springer-Verlag, N.Y.), *Handbook of Experimental Immunology*, Volumes I-IV (D. M. Weir and C. C. Blackwell eds 1986), *Remington's Pharmaceutical Sciences*, Mack Publishing Company, Easton, Pa., 19th Edition (1995); *Methods In Enzymology* (S. Colowick and N. Kaplan, eds., Academic Press, Inc.); and *Handbook of Experimental Immunology*, Vols. I-IV (D. M. Weir and C. C. Blackwell, eds., 1986, Blackwell Scientific Publications); Sambrook, et al., *Molecular Cloning: A Laboratory Manual* (2nd Edition, 1989); *Handbook of Surface and Colloidal Chemistry* (Birdi, K. S. ed., CRC Press, 1997); *Short Protocols in Molecular Biology*, 4th ed. (Ausubel et al. eds., 1999, John Wiley & Sons); *Molecular Biology Techniques: An Intensive Laboratory Course*, (Ream et al., eds., 1998, Academic Press); *PCR (Introduction to Biotechniques Series)*, 2nd ed. (Newton & Graham eds., 1997, Springer Verlag); and Peters and Dalrymple, *Fields Virology* (2d ed), Fields et al. (eds.), B. N. Raven Press, New York, N.Y.

Standard abbreviations for nucleotides and amino acids are used in this specification.

All publications, patents, and patent applications cited herein are incorporated in full by reference.

EXAMPLES

To illustrate the methods herein, *Streptococcus agalactiae* 090, H36b, M781, and CBJ111, which produce four representative serotypes (Ia, Ib, III, and V), isolated from patients with GBS disease, were studied.

Example 1-5 and 20 Liter Fermentation

A) Development of Inoculum Preparation Process

The study of the three GBS serotypes' growth was conducted in 5000 mL unbaffled shake flasks containing 1000 mL of the inoculum culture: 8 g/L dihydrate $Na_2HPO_4$ (Merck), 2 g/L monohydrate $Na_2HPO_4$ (Merck), 17 g/L autolysed yeast extract (Difco laboratories), 1 mg/L biotin (Merck) and 33 g/L monohydrate D-glucose (Merck). All compounds were dissolved in reverse osmosis water (ROW) and sterilized by filtration through a 0.22 µm pore size membrane filter (Nalgene) and then they were aseptically added to the 5000 mL Erlenmeyer flask sterilized in an autoclave at 122° C. for 30 minutes.

For each series of shake experiments, the medium (pH=7.3) was inoculated with different volumes of thawed culture (working seed were stored in 10% glycerol at −70° C.) and incubated at 35° C. with agitation at 200 rpm in a horizontal shaker cabinet (Innova 4330, eccentric 1 inch).

At various times during growth, the optical density at 590 nm was measured (Spectrophotometer novaspecII-Pharmacia Biotech) and pH-value was also monitored (pH-meter Metrohm) when the optical density values were higher or equal 0.5. The doubling time during the exponential phase was determined by regression analysis of the linear part of the growth curve. The slope of the line corresponds to the maximum specific growth rate, $\mu_{max}$, and doubling time ($t_d$) according to the formula $t_d = \ln 2/\mu$.

B) 5 and 20 Liters Fermentor Preparation

Before filling the vessel and sterilizing the culture medium, the fermentor instruments (pH electrodes and $pO_2$ meters) were calibrated using standard methods.

Since GBS is an auxotroph organism, it does not have the capacity to synthesize particular organic compounds, such as amino acids and vitamins, which are required for its growth. For this reason, a low-cost complex medium free of components from animal origin was developed, as described in WO07/052,168.

The basal medium used for polysaccharide production contained: 2 g/L dihydrate $Na_2HPO_4$ (Merck), 16.7 g/L autolysed yeast extract (Difco laboratories), 32 g/L monohydrate D-glucose (Merck), 1 mg/L biotin (Merck), 0.5 mg/L thiamine hydrochloride (BDH Laboratories), 0.5 mg/L riboflavin (Fluka), 0.5 mg/L nicotinic acid (Carlo Erba) 0.5 mg/L pyridoxine hydrochloride (Sigma) and 1 mL·L$^{-1}$ polypropylene glycol (BDH Laboratories) to prevent foam formation.

Since sterilization of an empty culture vessel was not possible, the fermentor was filled with the phosphate, yeast extract and polypropylene glycol (4.2 L for a 7 L fermentor and 16 L for a 30 L fermentor) and sterilized in situ at 121° C. for 30 minutes. Some liquid evaporated during sterilization. Since the exact loss of liquid due to evaporation was evaluated empirically with the medium height, a surplus of water was added before the sterilization (0.5 L for a 7 L fermentor and 1 L for a 30 L fermentor).

In parallel, a concentrated solution of monohydrate D-glucose (550 g/L) and vitamins (0.5 g/L for thiamine hydrochloride, nicotinic acid, pyridoxine hydrochloride, 0.05 g/L for riboflavin and 0.2 g/L for biotin) were dissolved in ROW, sterilized separately by filtration through a 0.22 µm pore size membrane filter (Nalgene) and then aseptically added to the fermentation vessel to obtain a right final concentration in fermentor (for a 7 L fermentor: 300 mL monohydrate D-glucose, 25 mL biotin, 5 mL vitamin solution (thiamine hydrochloride, nicotinic acid, pyridoxine hydrochloride) and 50 mL riboflavin; for a 30 L fermentor: 1000 mL monohydrate D-glucose, 100 mL biotin, 17 mL vitamin solution and 170 mL riboflavin).

C) Cultivation in 5 L and 20 L Fermentors

Expression of cps by GBS, as with others encapsulated bacterial pathogens, is not constitutive but instead varies during growth in vitro and in primary cultures isolated from different sites of infection (Ref. 173). Despite such observations, little is known about regulation of this surface-expressed carbohydrate antigen in GBS. Cell growth rate in continuous culture was already reported to be the principal factor regulating capsular polysaccharide production, and growth rate-dependent production of type III capsular polysaccharide occurred independently the growth limiting nutrients. In fact, the production of cps was higher when cells were held at a fast mass doubling time (1.4 h$^{-1}$) than at slow (11 h$^{-1}$) growth (Ref. 174).

Initially, all studies with GBS were performed with cells grown in batch culture, which were characterized by changing growth rate, nutrients concentration, and pH. Growth parameter shifts experienced by cells in batch culture lead to metabolic changes that affect the composition of the cell. Continuous culture allows for continuous exponential growth in an environment of stable substrate, product, and biomass concentrations and at a rate controlled by the researcher. If growth rate conditions are maintained, a steady state will be achieved. However, continuous culture should be avoided for industrial production because it is prone to strain stability problems and contamination, and is also expensive on manufacturing-scale due to the need for a continuous feed of medium and nutrients.

Cultivation at the 5 L- and 20 L-scale was carried out respectively in a Biostat CT5-2 and C20-3 reactors (B. Braun Biotech International), which had a total volume of 6.9 L and 31 L. The bioreactors were respectively equipped with 2 and 3 stirrers, each containing six paddles. In addition, ports for steam-sterilizable probes to measure the dissolved oxygen concentration (Inpro 6500 series2 oxygen sensor; Mettler Toledo), pH (model Pa/2; Mettler Toledo), temperature (pt100 electrode, M. K. Juchleim GmbH), foam (model L300/Rd.28; B. Braun Biotech International) were available. The operations were controlled and recorded with a DCU-3 digital controlled unit in combination with the MFCs/win software package (B. Braun Biotech International). Carbon oxygen and oxygen concentrations in the spent gas leaving the bioreactor were measured with 1310 fermentor monitor (Innova) and a GMUX-8 analyzer (B. Braun Biotech International).

Cultivation was done at 36° C.±1° C. with 0.2 bar of pressure and $pO_2$=30±10% saturation in the medium, which was controlled by agitation rates, between 100±10% and 700±10% rpm for a 7 L fermentor, and between 50±10% and 500±10% rpm for a 30 L fermentor, and by aeration rates of 0.1 and 1.0 v/v/m±10%. The pH of the medium was kept at 73±0.2 automatically by controlled addition of 4M hydroxide sodium. The monitoring and/or control of various parameters such as temperature, pH and agitation were performed in a PID control unit. Foam was controlled automatically with an antifoam agent emulsion (BDH Laboratories).

1000 mL of the inoculum sterile medium was inoculated with an adapted working seed volume of the strain studied and incubated for the desired time at 35° C. with shaking on a rotary shaker. When the inoculum flasks reached mid-exponential phase (OD between 0.8 and 1.2), sufficient volume of this culture was used to inoculate fresh batch medium (4.7 L or 17 L) to result in an initial OD of 0.032.

The batch phase of fermentation was allowed to proceed until the culture $OD_{590\ nm}$ reached 2.5 (±0.5). When the culture was at or near this OD value, the first exponential fed batch addition of yeast extract medium (150 g/L) was initiated and continued for 45-50 minutes to maintain a specific growth rate (ρ) of 0.138 h$^{-1}$. A second exponential fed batch addition of yeast extract media (150 g/L) to maintain a µ of 0.924 h$^{-1}$ was initiated at the end of the first part when the OD was equal to 4.5±0.5 and continued for 45-50 minutes. These addition phases reduced the bacteria's doubling time from 20-25 minutes, which is typical of the batch phase, to 45 minutes which allowed the micro-organism to adapt to the ideal conditions for polysaccharide production. Ultimately, to increase productivity, at the end of the second addition of yeast extract when the OD was at 10.0±2, the culture was continued using a pH-regulated feed of concentrated monohydrate D-glucose (550 g/L) for 3 hours, avoiding completely depletion of the substrate which would result in pigment production and a reduction of capsular polysaccharide production.

Small samples of 50 mL were withdrawn from the culture fluid at intervals during the fermentation processes and analyzed for bacterial growth, glucose consumption and polysaccharide production.

D) Harvest and Inactivation of GBS

The culture was harvested when the growth rate consistently slowed down, which occurred 3 hours after the initiation of the pH-controlled glucose phase. The culture was immediately centrifuged at 7741×g for 45 minutes at ambient temperature (Avanti™ centrifuge J-20 XPI Beckmam coulter). The supernatant was removed and conserved at −20° C. for glucose assays, and the weight of harvest was determined.

Purification of GBS polysaccharides first required the inactivation and hydrolysis of cps. 1M sodium hydroxide was added to the pellet to obtain a final concentration of 0.8M. The reaction mixture was incubated for 36 hours at 37° C. and 120 rpm before the serotype specific cps content was determined.

E) Fermentor Cleaning

After the culture was harvested, the vessel and accessories were decontaminated. First, the fermentors were filled with ROW and the pH was increased to 12 by manually addition of 4M sodium hydroxide. Sanitization was performed by heating the water to 80° C. for 30 minutes, maintaining a pressure of 0.2 bar and an agitation of 200 rpm that ensured a homogenous dispersion of heat. When the sanitization was completed, the water with sodium hydroxide was harvested, and the fermentor was washed with ROW until the pH-value was decreased to a range 5-7. Generally, three washings were necessary before reaching the desired pH. The fermentor was emptied, and the probes and accessories were removed from their ports. The septum connectors for inoculation and transfer of additive nutrients and corrective agents, and the bottles for removal and storage samples were sterilized separately in an autoclave for 30 minutes at 122° C. The fermentor was again filled with ROW, and sterilized at 121° C. for 30 minutes.

Example 2-2 Liter Fermentation

A) Strain and Cultivation Medium

*Streptococcus agalactiae* type III strain M781, originally isolated from a newborn with GBS meningitis, was provided by Carol J. Baker. Strain M781 cells were grown in a modified version of a chemically defined medium, initially developed for group A streptococci (Ref. 174). The composition of the chemically defined medium used in the batch culture study is listed in Table 1.

TABLE 1

Chemically defined medium composition batch phase

| CHEMICAL COMPOUNDS | FINAL CONCENTRATION (mg · L$^{-1}$) | PRODUCER |
|---|---|---|
| Carbon source in ROW | | |
| D-Glucose. H$_2$O | 20000 | Merck |
| Phosphate solution in ROW | | |
| K$_2$HPO$_4$ | 300 | Merck |
| KH$_2$PO$_4$ | 440 | Merck |
| Na$_2$HPO$_4$•2H$_2$O | 3150 | Merck |
| NaH$_2$PO$_4$•H$_2$O | 2050 | Merck |
| NaCl | 10 | Merck |
| Sulphate solution in ROW | | |
| (NH$_4$)$_2$SO$_4$ | 600 | Ashland |
| MgSO$_4$•7H$_2$O | 200 | Merck |
| MnSO$_4$•H$_2$O | 10 | Sigma |
| FeSO$_4$•7H$_2$O | 10 | Sigma |
| Sodium solution in ROW | | |
| Sodium citrate | 225 | Sigma |
| Sodium acetate | 6000 | Carlo Erba |
| Vitamins solution in ROW | | |
| Biotin | 0.01 | Merck |
| Nicotinamide | 2 | Carlo Erba |
| Ca Panthotenate | 0.8 | Merck |
| Riboflavin | 0.4 | Fluka |
| Thiamine hydrochloride | 0.4 | Merck |
| Pyridoxine hydrochloride | 0.8 | Sigma |
| Vitamin solution in sodium hydroxide 1 mol · L$^{-1}$ | | |
| Folic acid | 0.1 | Sigma |
| Nitrogenous bases in sodium hydroxide 1 mol · L$^{-1}$ | | |
| Adenine | 35 | Sigma |
| Guanine | 27 | Sigma |
| Uracil | 30 | Sigma |
| Amino-acids in ROW | | |
| L-Alanine | 200 | Sigma |
| L-Arginine | 200 | Sigma |
| L-Glutamine | 5 | Sigma |

TABLE 1-continued

Chemically defined medium composition batch phase

| CHEMICAL COMPOUNDS | FINAL CONCENTRATION (mg · L$^{-1}$) | PRODUCER |
|---|---|---|
| Glycine | 200 | Sigma |
| L-Histidine | 200 | Sigma |
| L-Isoleucine | 100 | Sigma |
| L-Leucine | 100 | Sigma |
| L-Lysine | 110 | Sigma |
| DL-Methionine | 100 | Sigma |
| L-Phenylalanine | 100 | Sigma |
| L-Proline | 200 | Sigma |
| DL-Serine | 100 | Sigma |
| L-Threonine | 100 | Sigma |
| L-Tryptophan | 200 | Sigma |
| L-Valine | 100 | Sigma |
| Amino-acids in sodium hydroxide 1 mol · L$^{-1}$ | | |
| L-Aspartic acid | 100 | Sigma |
| L-Cysteine hydrochloride | 200 | Sigma |
| L-Glutamic acid | 300 | Sigma |
| L-Tyrosine | 200 | Sigma |

The pH probe was calibrated by a two point calibration using two standard solutions (pH-values=7 and 4). The pO$_2$ and pH probes were mounted in the culture vessel. The fermentor (Applikon 3 L) was filled with glucose and sterilized in an autoclave at 122° C. for 30 minutes. All others compounds were sterilized separately by filtration through a 0.22 μm pore size membrane filter, and then aseptically added to the fermentation vessel. In order to avoid the precipitation of medium, concentrated solution were prepared (20× phosphate, 100× sulphate, 50× sodium, 240× nitrogenous bases, 9000× vitamins, 35× amino acids in water and 90× amino acids in sodium hydroxide) and an appropriate volume of each was added in the following order to the carbon source to produce the desired final concentration: phosphate, amino acids, vitamins, sulphate and nitrogenous bases. When all additions were performed, the pO$_2$ probe was calibrated. For the "zero" measurement, the culture vessel was sparged overnight with nitrogen. After the culture was saturated with oxygen and when the operations conditions were reached the electrode slope was calibrated to 100%.

B) Cultivation at 2 L Scale

Preliminary experiments on the expression of capsular polysaccharides by strain M781 were performed in batch culture.

For cell activation, 100 mL of the chemically defined medium (pH value=7.2, adjusted using 6M chlorhydric acid), sterilized by filtration though a 0.22 μm pore size membrane filter (Nalgene) and placed in sterile 500 mL Erlenmeyer flasks, were inoculated with 0.1 mL of thawed culture of M781 strain (working seed were stored in 10% glycerol at −70° C.). This seed culture was incubated at 35° C., with agitation at 200 rpm in a horizontal shaker cabinet (Innova 4330, eccentric 1 inch) for 9 hours. The seed culture was then inoculated into 1.8 L of the basal medium in a 2.5 L jacketed fermentor (Applikon), whereby the initial OD was 0.4.

The fermentation was controlled by a digital measurement and a control unit from Applikon Instruments (Biol controller ADI 1030, Applikon), and all data were collected by computer (BioXpert software). The temperature was automatically controlled at 36° C. by an external thermostat (Haake). Dissolved O$_2$ was measured by a sterilizable electrode (Applisens) and was maintained above 30% of air saturation by automatic adjustment of the agitation speed between 150 to 1000 rpm (Motor Controller ADI 1012) and aeration rates of 0.1 and 1.0 v/v/m (Flow console Applikon). The culture pH was maintained at 7.3 by automatic titration with 2M sodium hydroxide (pump driver Masterflex).

For the fed batch culture studies with unknown growth limiting factors, the cultivation was initiated with a batch growth phase (1.2 L), followed by a feeding phase. To develop the best fed batch strategy, three fed batch techniques were tested for each cell growth: (1) pH-stat, (2) DOT-stat, and (3) exponential. The cps concentration was monitored at regular intervals.

To control substrate feeding using the pH-stat method, the cultivating medium's pH was adjusted to 7.3 during the cultivation processes by the addition of a feed solution with a peristaltic pump (Masterflex Concode Drive). When the pH exceeded the set point of 7.3, glucose was depleted. Consequently, supplemental nutrients were automatically added to readjust the pH to the set point.

For the $pO_2$-stat strategy, the carbon source feed was added automatically whenever the $pO_2$ increased above the set point of 40% of dissolved oxygen.

For the exponential cultivation technique, the peristaltic pump was activated at the end of exponential phase to maintain a specific growth rate equal to 0.92 $h^1$ ($t_d$=45 minutes), the optimal doubling time for capsular polysaccharide production. Feeding was accomplished according to the following formula:

$$F = \frac{\mu(VX)_0 e^{\mu t f}}{S \cdot Y_{X/S_{f,const}}}$$

where F is the feeding rate, $\mu$ is the specific growth rate, $(VX)_0$ is the biomass at the start of feeding, tf is the time when feeding started, $S_{f,const}$ is the substrate concentration of feed, and $Y_{X/S}$ is the cell yield coefficient for glucose.

C) Shake Flasks Study to Identify the Growth Factors Requirements

Growth factor requirements of the organism were determined by eliminating individual nutrients from the defined medium and by determining whether the resultant medium would support growth. The study was conducted in 500 mL unbaffled shake flasks containing 100 mL of chemically defined medium (see Table 1).

The pH of the cultivating medium was adjusted to 7.2 using 6M chlorhydric acid. The cultivating medium was then sterilized by filtration though a 0.22 μm pore size membrane filter (Nalgene). For each series of shake experiments, the cultivating medium was inoculated with 0.1 mL of thawed culture of M781 strain (working seeds were stored in 10% glycerol at −70° C.), and incubated at 35° C. with agitation at 200 rpm in a horizontal shaker cabinet (Innova 4330, eccentric 1 inch). After 18 hours of cultivating, the OD at 590 nm (Spectrophotometer novaspecll-Pharmacia Biotech) and pH-value (pH-meter Metrohm) were measured.

The growth in amino acid and vitamin deficient media was compared with a control culture with all compounds present.

Example 3-Analytical Methods

A) Growth measurements

As soon as the samples were collected, the biomass content was monitored by reading the OD of the culture at a wavelength 590 nm (Novaspec II spectrophotometer—Pharmacia bioteck). Dilutions of the samples were realized in order to read a value of absorbance within the interval 0.10-0.50.

Cell concentration, defined as g/L of chemically defined medium was determined by placing an accurately measured volume of culture broth (30 mL) into a previously dried and weighed 50 mL polypropylene centrifuge tube. Cells were centrifuged at 27,217×g for 45 minutes at 4° C. in an Avanti-TM JA-20 XPI Beckman Coulter refrigerated centrifuge. The supernatant was decanted and the cell pellet was dried in an oven at 85° C. for 24 hours, and weighed. A relationship between the OD at 590 nm and $g_{CDW}$/L (cell dry weight) biomass was established. An OD of 1 at 590 nm was equivalent to 0.44 $g_{CDW}$/L biomass.

B) Gram Staining

Gram's stain differentiates between two major cell wall types. Bacterial species with walls containing small amounts of peptidoglycan and, characteristically, lipopolysaccharide, are Gram-negative, whereas bacteria with walls containing relatively large amounts of peptidoglycan and no lipopolysaccharide are Gram-positive. This method, used for both laboratory and pilot scale, provided assurance that the seed culture and fermentor culture were pure.

With respect to the staining technique, cells on a microscope slide were heat-fixed and stained with a basic dye, crystal violet, which stains all bacterial cells blue. Then, the cells were treated with an iodine-potassium iodide solution that allowed the iodine to enter the cells and form a water-insoluble complex with the crystal violet dye. The cells were treated with an alcohol solvent, in which the iodine-crystal violet complex was soluble. Following the solvent treatment, only gram-positive cells remained stained.

After the staining procedure, cells were treated with a counterstain, safranin to visualize the decolorized gram-negative cells. Counterstained gram-negative cells appeared red, while gram-positive cells remained blue. After the counterstain was rinsed off, the slide was gently warmed to remove any residual moisture. The slide was then placed on a microscope stage, where the oil-immersion lens was lowered into the immersion oil.

C) Glucose Assays

In culture supernatants, glucose consumption was determined colorimetrically by measuring the absorbance of the solution in a 1 cm light path at 340 nm (NADPH) and by comparing it to a standard curve prepared by assaying pure glucose.

D-Glucose was phosphorylated to D-Glucose-6-phosphate in the presence of the enzyme hexokinase and ATP with the simultaneous formation of ADP:

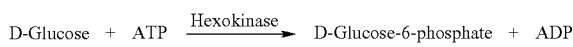

In the presence of the enzyme glucose-6-phosphate dehydrogenase, D-Glucose-6-phosphate was oxidized by NADP to D-gluconate-6-phosphate with the formation of NADPH:

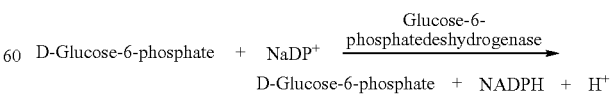

The amount of NADPH formed in this reaction was stoichiometric to the amount of D-Glucose.

The amount of D-Glucose present in the assay was between 1 μg and 50 μg. In order to get a sufficient absorbance difference, the sample solution was diluted to yield a D-Glucose concentration between 0.08 and 0.5 g/L.

The supernatant, stocked in fridge at −20° C. to stop enzymatic reaction, was serially diluted in ROW. 50 μL of diluted supernatant was incubated at ambient temperature for 15 minutes with 10 μL of a solution containing hexokinase (approximately 320 U) and glucose-6-phosphate dehydrogenase (approximately 160 U) in triethanolamine buffer with NADP, ATP and magnesium sulphate (pH=7.6).

After preparation of the sample in the disposable cuvette (1 cm light path) according the Roche procedure, the spectrophotometric measurement was performed at room temperature at 340 nm against air.

D) Determination of Capsular Polysaccharide Content

N-acetyl-D-neuraminic acid (sialic acid) is an acidic sugar frequently found as a component of eukaryotic carbohydrate structures (glycoproteins and glycolipids). In prokaryotic cells, sialic acid has also been found as a constituent cps of a few genera of pathogenic bacteria [10]. In fact, the serotype-specific cps of GBS comprises a repeating unit of the following saccharides: N-acetyl-neuramic acid or sialic acid, glucose, galactose and N-acetylglucosamine. Since sialic acid is an integral component of the polysaccharide, its quantitative determination was used to monitor serotype specific cps production following the chemical method setup by Svennerholm (Ref. 176).

Before determining the quantity of sialic acid, the cps in the inactivated sample was partially purified and concentrated. After the hydrolysis of polysaccharides in sodium hydroxide for 36 hours, 1.5 mL of the inactivated samples was centrifuged at 15600×g for 25 minutes (Centrifuge 5415R—Eppendorf) to remove the cells. The supernatant was diluted in ROW at 1:10, and then purified and concentrated using a centricon centrifugal filter (Millipore's Ultracel YM-30 regenerate cellulose). Concentration was achieved by utrafiltering the diluted sample through an anisotropic membrane according to the following procedure.

After inserting the sample reservoir into a filtrate vial, 1.5 mL of water was added twice to a sample reservoir, and spun for 20 minutes at 2519×g and 20° C. to clean the centricon system. Once the system was ready, 1.5 mL of the diluted samples were added and centrifuged at 2519×g for 30 minutes. The centrifugal force drove solvents and low molecular weight solutes through the membrane into the filtrate vial. Macromolecules such as the cps were retained above the membrane inside the sample reservoir. As the sample volume was diminished, the retained solute concentration increased. The retentate was washed three times with 0.5 mL of NaCl 0.5M to eliminate the contaminants, and was centrifuged at 2519×g at 20° C. for 20 minutes.

For recovery, 0.5 mL of 0.5 mol·L$^{-1}$ NaCl was added to the sample reservoir. The cps was transferred to the retentate vial by placing the vial over the sample reservoir, inverting the device, then centrifuging for 1 minute at 205×g. This recovery process was repeated twice to recover all the cps.

To quantify the amount of sialic acid, a colorimetric method involving resorcinol-hydrochloric acid was used. The reagent for the quantitative assay contained 0.2 g of resorcinol (Merck) in a solution containing 80 mL of 37% HCl to assure acid hydrolysis, 20 mL of water and 20 μmol of $CuSO_4 5H_2O$ (Merck).

The assay was performed as follow: 1 mL of the sample containing 5-25 μg of sialic acid was added to 2 mL of resorcinol reagent. After the addition of reagent, the solutions were mixed and heated at 100° C. for 20 minutes in a boiling water bath, during which a blue-violet color developed.

The tubes were cooled at room temperature, and the absorbance was read at 554 nm using a Novaspec 11 spectrophotometer. Disposable cuvettes with a 1 cm light path and 1 mL capacity were used. The absorbance was directly proportional to the concentration in the range 5-25 μg of sialic acid.

In order to compensate for non-specific color in biological materials, a control sample was run without resorcinol. The sample blank absorbance was subtracted from the test sample before calculating the amount of sialic acid.

In parallel, standard solutions of 0, 5, 10, 15, 20 and 25 μg N-acetylsialic acid were prepared under the same conditions. The amount of N-acetylsialic acid was calculated using the equations derived from the standard solutions of N-acetylsialic acid with the program UV LAMBDA.

Capsular polysaccharide of 090, H36b and M781 contains 31% (w/w) N-acetylsialic acid. The capsular polysaccharide of CJB111 contains 23% (w/w) N-acetylsialic acid. Thus, the cps concentration could be ascertained using this correction factor. Volumetric production of cps was expressed in units of mg/L, and specific cps production was expressed in units of mg/L·OD.

Example 4-Simplified Complex Media and Linear Additions

A) Development of Inoculum Preparation Process

In the fermentation process to produce serotype specific cps of GBS, 2000 mL shake flasks containing 500 mL of medium were used to prepare the inoculum culture. However, these flasks were not suitable for pilot and production scale. Thus, the behavior of four GBS strains (090, H36b, M781, and CJB111) was studied in new flasks to develop an inoculum preparation process suitable for pilot scale. This procedure was then used to produce pre-phase I clinical lots according to cGMP.

The first goal of this example was to find the growth parameters of these four GBS strains in 5000 mL Erlenmeyer flasks containing 1000 mL of medium, and to also study the optimal culture time required for a late-exponential growth phase with a suitable pH-value in the fermentor. The second goal was to study the volume of working seeds used to inoculate the flasks in order to modify the culture time such that it could be initiated either the evening before the fermentation day (culture time about 8 hours) or early in the morning of the fermentation day (culture time about 3 hours), as appropriate for the growth rate of the strain.

The study of the three GBS serotypes was conducted using 3 mL of the working seed to inoculate 1000 mL of fresh sterile inoculum medium. Furthermore, each experiment was performed twice to ensure reproducibility. However, since the growth curve and doubling time obtained were similar, only one result of each experiment has been presented.

For the 090 strain, the cells remained in the exponential growth phase for 6.5 hours with a doubling time of 30 minutes ($\mu_{max}$=1.41 h$^{-1}$). Therefore, 6 hours was sufficient to attain the mid-exponential growth phase using a suitable pH value of 6.8). Since this length of time was not enough to inoculate the flasks in the evening before the fermentation day, the working seed volume was reduced to 0.1 mL to increase this cultivation time. Under these conditions, the bacteria remained in exponential growth phase for 8.5 hours with a doubling time of 35 minutes ($\mu_{max}$=1.20 h$^{-1}$). Thus, the preparation of the inoculum culture for this strain required 8 hours.

For the H36b strain, only one experiment with 3 mL of the working seed was performed. The cells immediately entered exponential growth phase with a doubling time of 25 minutes ($\mu_{max}$=1.65 h$^{-1}$), and the deceleration phase was initiated after 4.5 hours. Thus, in order to obtain an OD in the range 0.8-1.2 with pH-value around 6.5 (7+0.5), the medium for this strain had to be inoculated 4 hours before fermentation.

For the M781 strain, the experiment was performed twice, first using a working seed volume of 3 mL and then using 0.1 mL. Using 3 mL of the working seed volume, 7.5 hours was necessary for the cultivation time. In order to increase the culture time by 2.5 hours to allow culturing overnight (5 doubling times), 0.1 mL of working seed volume was used. It was observed that the difference time was only 30 minutes and doubling time was reduced from 31.4 minutes ($\mu_{max}$=1.32 h$^{-1}$) to 27.5 minutes ($\mu_{max}$=1.51 h$^{-1}$). Thus, using 0.1 mL of working seed volume for this strain, the flasks had to be inoculated for 8 hours before fermentation.

For the CJB111 strain only one experiment with 3 ml of the working seed was performed. The cell immediately entered in exponential growth phase with doubling time of 21 min ($\mu_{max}$=1.98 h$^{-1}$) and the deceleration phase began after 4.5 h. Thus, in order to obtain an OD in the range of 0.8-1.2 with a pH-value around 6.5 (7.0+/−0.5), the medium had to be inoculated 4 hours before fermentation.

culture time was 7.50 hours to achieve the desired OD range of 0.8-1.2. For the CJB111 strain, the working seed volume was 3 mL and the culture time was 4 hours to achieve the desired OD.

This inoculum preparation process was used in pilot scale, and required 4 flasks containing 1000 mL of medium to achieve an initial OD of 0.032 in a 200 L fermentor.

B) Development of Fermentation Process i) Verification of the Need to Add Vitamin Solutions in the Complex Cultivating Medium Since GBS is an auxotroph organism, it does not have the capacity to synthesize particular organic compounds, such as amino acids and vitamins, which are required for its growth. For this reason, a low-cost complex medium free of components from animal origin was developed, as described in WO07/052,168. This complex cultivating medium was sterilized by heat, to which biotin and vitamin solutions of thiamine, riboflavin, nicotinic acid and pyridoxine at 0.5 g/L in 0.1M sodium hydroxide and methanol were added.

The yeast extract used for the growth of the GBS strains contained these vitamins, even if the ratio may differ significantly depending upon production process and processing of yeast autolysates (Table 2) (Ref. 177).

TABLE 2

Vitamin physiological meanings of GBS and concentrations in yeast extract

| | Physiological role | Vitamin concentration (mg/L) in the medium due to the addition of the vitamin solution | Vitamin concentration (mg/L) in the medium due to the yeast extract |
|---|---|---|---|
| Vitamin B1: Thiamine | Essential component of a thiamine pyrophosphate coenzyme involved in energy metabolism | 0.5 | 1.08 |
| Vitamin B2: Riboflavin | Role in oxido-reduction reaction | 0.5 | 4.28 |
| Vitamin B3: Nicotinic Acid | Electron carrier in dehydrogenation reaction | 0.5 | 24.5 |
| Vitamin B6: Pyridoxine | Coenzyme in transamination reactions involving α-amino acids | 0.5 | 0.83 |
| Vitamin B8: Biotin | Importance in fatty acids, amino acids and carbohydrate metabolism | 1.0 | 0.09 |

Before this new inoculum process could be transferred to pilot scale, the behavior of the four GBS strains was studied in cGMP conditions to validate the inoculum preparation process. As reported in Good Manufacturing Practices (volume 4): "Validation studies were conducted in accordance with defined procedures. When any new manufacturing formula or method of preparation was adopted, steps should be taken to demonstrate its suitability for routine processing. The defined process, using the materials and equipment specified, should be shown to yield a product consistently of the required quality." The new inoculum preparation process was repeated using the optimal working seed volume of each strain. The growth behavior was identical to the preceding study. For the 090 strain, the working seed volume was 0.1 mL, and the culture time was 8.50 hours to achieve the desired range whereby the OD is 1±0.2 and pH is 6.5±0.2. For the H36b strain, the working seed volume was 3 mL, and the culture time was 4 hours to achieve the late exponential phase. For the M781 strain, the working seed volume was 0.1 mL, and the To attain a simple cost-effective production process, the role of biotin and the four vitamin solutions added to the complex cultivating medium were assessed for their effect upon growth and cps production of the three specific strains of *Streptococcus agalactiae*.

Before developing the fermentation process to transfer of the cps process to pilot scale, the growth of the three GBS serotypes was monitored in a fermentor at laboratory scale using parameters developed in previous Examples.

In these conditions, final ODs after 3 hours of glucose feed varied from 14 for the 090 strain to 28.5 for the H36b strain, and the cps concentration for these strains was between 300 mg/L and 550 mg/L.

Since methanol had to be avoided for safety reasons and vitamins in sodium hydroxide lost their property, a ROW solution of thiamine, pyridoxine and nicotinic acid was selected. At the same time, a second modification was made to the process. Since vitamins are thermo-labile compounds, the yeast extract medium was sterilized by filtration through a 0.22 µm pore size membrane filter rather than autoclaving, and aseptically added to the phosphate medium, rather than by sterilization using an autoclave at 121° C. for 30 minutes.

A new fermentation experiment was performed for each strain taking into consideration the modifications previously described. Although the growth for the three stains was equal (H36b) or better (090 and M781) than the process established in previous Examples, the pigmentation of the culture persisted. In fact, in an article by Fraile et al., the production of an orange-yellow pigment integrated in the cell wall was a specific characteristic of human haemolytic GBS and served as the basic for use of culture media to identify GBS from clinical samples (Ref. 178). In order to eliminate this chemical contamination (color), the purification process required an additional step using a Z-carbon surface.

With respect to the cps production at the end of fermentation, the modifications increased cps concentration by about 100 mg/L for the 090 and H36b strains and 300 mg/L for the M781 strain. Furthermore, the percentage of cps by gram of cell dried weight was higher. The addition of riboflavin was not necessary for these three strains of Streptococcus agalactiae because the vitamin concentration in the yeast extract was sufficient to satisfy the nutritional needs of these strains.

In order to reduce vitamin solutions added to the medium, experiments only using biotin were performed. Although the cps concentration was slightly decreased for the H36b and M781 strains, the cps production was still an improvement over the process established in previous Examples. The addition of vitamins to the complex cultivating medium was not necessary for the growth and cps production of Streptococcus agalactiae because the vitamins in yeast extract were sufficient to satisfy the nutritional needs of the three specific strains of GBS with the exception of biotin.

Moreover, according to the purification data, the cps structure in the absence of vitamins was comparable to the structure obtained in the process established in previous Examples, the acetylation was low, and the purity of product was acceptable.

The growth of the 090 strain was also monitored upon removing biotin. In this experiment, both the OD decreased from 18 to 14 in presence of biotin and the cps concentration was reduced by more than 100 mg/L. The biotin concentration in the yeast extract was not sufficient to satisfy the growth needs of this GBS strain. In fact, according to yeast extract composition, biotin was present in lower quantities (0.25 mg/100 g) when compared to the other vitamin concentrations.

In conclusion, removal of thiamine, riboflavin, nicotinic acid and pyridoxine had little effect on the growth and cps production of GBS. For theses reasons, the four vitamins were removed from the fermentation process, so that only biotin was added to the complex cultivating medium. For CJB111, the final conditions using biotin only was used.

ii) Verification of the Necessity of Complex Fed Batch Process to Produce Serotype Specific Capsular Polysaccharides of GBS Cell growth rate was previously reported to be the principal factor regulating cps production, and the growth rate-dependant production of type III cps occurred independently of the growth-limiting compounds (Ref. 173). However, the depletion of carbon source was found to be a cause of pigment formation and reduction of capsular polysaccharide production. To maintain a nutritious environment and a growth rate favorable to cps production, a complex fed batch fermentation process was developed as described in WO07/052,168. This complex fed batch process combined both an exponential technique to reduce the bacteria' doubling time and a pH-stat technique with glucose in the last 3 hours to increase cps productivity. This process combined the advantages of batch and continuous techniques. In fact, fed batch fermentation achieves high cell densities by extending the exponential growth phase and control over substrate addition conditions during fermentation. However, the use of a complex fed batch technique requires using software that manages the fermentation through algorithm, and use of this software necessitates the validation of the algorithm to comply with GMP standards. Therefore, the fermentation process was simplified to avoid using the algorithm.

In accordance with the process established in previous Examples, the same OD values were used as triggers for initiation of each feed and the instantaneous additions. Furthermore, 150 g/L of yeast extract and 500 g/L of glucose were added to the batch, which constituted 10% of initial batch volume. The two instantaneous additions of yeast extract at OD of 3 and 4.5, respectively, constituted ⅕th and ⅘th of the total required volume. When the OD reached 10, a linear addition of concentrated glucose was initiated to replace the pH-stat phase. The velocity of this addition was calculated to add the same amount of glucose as the complex fed batch process in 3 hours.

The fermentation was performed for each strain using the new process, and the cell density and cps production were monitored. For the 090 strain, the simplified process produced the same result as the complex fed batch process. For both the 090 and H36b strains, the growth was faster than complex fed batch technique and the OD at the end of the process increased from 24 to 32. The cps concentration and the cps quantity by gram of cell dried weight increased by approximately 300 mg/L and 5 $mg_{cps}/g_{CDW}$, respectively. For the M781 strain, the same growth and cps production was observed. Thus, the fermentation process could be simplified using the linear addition of glucose without pH monitoring. For CJB111, the only the final process sith the simplified linear addition without pH monitoring was performed to verify the efficacy of the protocol.

This process using two instantaneous additions of yeast extract and a linear addition of glucose was the preferred pilot-scale method. The new process did not require the use of an algorithm or the addition of vitamin solutions to the cultivating medium. The complex cultivating medium, which was comprised of yeast extract, phosphate, glucose and biotin, was a low-cost robust process that led to reproducible growth behavior and cps production.

C) Pre-Validation of Fermentation Process

The previously developed fermentation process to produce cps of GBS was validated and optimized. The growth and cps production were monitored for the H36b strain, whereby each parameter was modified individually and compared with a control culture. The DOT study, the temperature and pH were reported.

The cultivation was performed at 36° C. with a pH of 7.3, and the dissolved oxygen in the medium was maintained at 30% during the entire process. After 3 hours of feeding glucose, the final OD was 25.3, and the average productivity was 1.84 g/L.h. The cps concentration and quantity of cps in one gram of cell dried weight were respectively 540 mg/L and 59 $mg_{cps}/g_{CDW}$.

i) Effect of the Dissolved Oxygen Level

Streptococcus agalactiae is a facultative anaerobic organism that synthesizes ATP by aerobic respiration if oxygen is present; however, it is also able to switch it to anaerobic growth.

First, the dissolved oxygen in the medium was maintained at 15%. The average productivity was reduced from 1.84 g/L.h to 1.14 g/L.h but the same OD of 23.2 at 590 nm was observed at the end of the process. The cps concentration was lower at around 406 mg/L and less cps were produced by gram of cell dry weight (39.8 $mg_{cps}/g_{CDW}$).

The same fermentation was performed maintaining the dissolved oxygen at 60%. In this case, the average productivity was 1.16 g/L.h and the final OD was 20.5. The specific productivity was decreased to 433 mg/L and the quantity of cps by gram of cell dry weight was reduced to 49 $mg_{cps}/g_{CDW}$.

In light of these observations, 30% of dissolved oxygen was selected for the pilot-scale production, using an agitation between 50-350 rpm and air flow between 20-100 L/min. Oxygen, which is expensive as a gas, was only used in the last hour of the fermentation process, thereby keeping the cost of the manufacturing process down.

ii) Effect of the Temperature

The growth and cps production were also monitored by modifying the temperature by increasing and decreasing the temperature by 2° C. with respect to the standard temperature at 36° C.

By lowering the temperature to 34° C., the doubling time was reduced and the average productivity was decreased from 1.84 g/L.h to 1.04 g/L.h. However, the cps concentration was decreased to 60% (312 mg/L), and approximately 20 $mg_{cps}/g_{CDW}$ were lost at this temperature.

When the process was repeated at 38° C., a reduction in average productivity was observed from 1.84 g/L.h to 1.45 g/L.h. Furthermore, a significant reduction of both cps concentration and the quantity of cps per gram of cell dry weight was observed at the end of the process (267 mg/L and 32.1 $mg_{cps}/g_{CDW}$, respectively).

Since modifying the temperature of the fermentation process affected the GBS doubling time and considerably reduced serotype specific cps production, 36° C. was confirmed to be optimal temperature for GBS growth and cps production.

iii) Study of the pH-Values

Experiments were also performed to optimize the pH-value, by varying the original pH at 7.3 to 7.0 and 7.5. When the pH was maintained at 7.0, the final OD was increased from 23.5 to 28.8, and the average productivity was 1.52 g/L.h. However, cps concentration was decreased from 540 mg/L to 412 mg/L.

The same fermentation process was performed with a pH of 7.5. The same growth behavior for OD, but a average productivity of 1.08 g/L.h was observed and a significant decrease of cps volumetric productivity was noted from 540 mg/L to 323 mg/L. Thus, maintaining a pH of 7.3 during the fermentation process was optimal for cell density and cps production.

iii) Study of the Pressure-Values

Experiments were also performed to optimize the pressure by comparing the fermentation process at two pressures: 0.2 to 0.5 bar. When the pressure was maintained at 0.5, the final OD was manteined 23.5, and the average productivity was 1.5 g/L.h. However, cps concentration was decreased from 540 mg/L to 272 mg/L.

After studying the effects of dissolved oxygen, temperature, pH, and pressure, conditions previously established were found to be the optimal conditions for producing both high cell density and serotype specific cps.

Example 4-Development of a Chemically Defined Medium

Since, the complex cultivating medium used in preceding Examples contained organic sources whose compositions are not completely known (e.g., yeast extract), variability in the performance of the fermentation process was observed. One approach to reduce variability while maintaining productivity is to replace the complex medium with a chemically defined medium which primarily consists of inorganic compounds. This replacement allows the fermentation process to be controlled, and also simplifies the purification of polysaccharides.

Previous studies (Ref. 179) demonstrated that *Streptococcus agalactiae* could be grown in a chemically defined medium which supported a rate and an amount of growth comparable to that obtained in the complex medium. The purpose of this investigation was first to study the growth characteristics and examine growth factors requirements of M781 strain of *Streptococcus agalactiae* representing serotype III. To increase the yield of biomass and cps production, a simple fed batch process was developed.

A) GBS Growth Study in a Chemically Defined Medium

To develop a fed batch process, typically the micro-organism must first be analyzed to ascertain the best abiotic conditions, the different growth phases, the consumed and produced components, the relationship between the biomass and product formation, the limiting substrate for growth and the relationship between the specific growth rate and the limiting substrate concentration. However, behavioral information about GBS was already known from the studies performed to develop the complex cultivating medium. The optimum conditions for pH and temperature developed in preceding Examples for GBS growth in the complex cultivating medium were extended to the chemically defined medium as set forth in Table 1 above.

i) GBS Growth Study in Erlenmeyer Flasks

Preliminary experiments on the growth by strain M781 were performed in batch culture using 500 mL Erlenmeyer flasks. The cells were maintained in exponential phase for 8 hours with a doubling time of 45 min ($\mu_{max}$=0.91 $h^{-1}$). After this first growth phase, the specific growth rate began to decrease and the cells were in deceleration phase for 2 hours. The final optical density was around 1.5 and the exponential phase was finished when optical density was around 0.7.

ii) GBS Growth Study in 2 L Fermentor

Next, GBS growth was monitored in a 2 L fermentor. Under these conditions, the pH of the cultivating medium was maintained at a constant pH of 7.3 by the automatic addition of 2M sodium hydroxide.

For cell activation, the preceding culture in the flasks was used. When inoculum flasks reached late exponential growth phase ($OD_{590\ nm}$=0.5), an adapted volume of this culture was used to inoculate 1.8 L of fresh medium, which resulted in an initial OD of 0.4. The cells immediately entered into exponential growth for 3 hours with a doubling time of 42 minutes ($\mu_{max}$=1.00 $h^{-1}$). The 2-hour deceleration phase was followed by a stationary phase whereby the OD was 2.56. The same doubling time was observed both in the flasks and in the fermentor. Although a slight improvement was noted for the final OD, the biomass production yield (0.05 g/L.h) remained low. As observed in the fermentor, the pH was constantly maintained at 7.3. Furthermore, it was observed that glucose was not the limiting source for GBS since the available glucose was 5.7 g/L when the cells entered in the beginning of the deceleration phase.

B) Identification of Limiting Compounds

Based on the composition of yeast extract medium that is approximately known, a comparison between the concentration of nutritional sources used in the complex medium process and the composition of the batch defined medium was performed to determine an approximate ratio among the different compounds required by GBS to reach a final OD around 15 and to identify the limiting compounds for growth. The process involving the complex medium contained 17 g/L of yeast extract in the batch medium and 19 g/L were added during the feed. Thus, 36 g/L were available for *Streptococcus agalactiae*.

The comparison between the composition of 36 g/L of yeast extract and initial concentration of defined medium was performed on the mineral, glucose, vitamins and amino acids contents (see Table 3). For the mineral sources, all compounds present in the current defined medium were sufficient to satisfy the GBS growth requirements, except potassium which was 6.5 times more abundant in the complex medium. For the vitamin and amino acid sources, in all cases, the concentrations observed in the process using the defined medium were lower than the concentrations in the process using the complex medium. The ratios of the vitamin or amino acid concentration present in yeast extract compared to the batch concentration in the defined medium were heterogeneous compared to nature of the molecules. However, the exact composition of the yeast extract is not well defined. Values used for the comparison are also averages and the ratio of each component may differ significantly according to the production process and processing of yeast extract.

TABLE 3

Comparison of composition complex medium and CDM process

| Chemical compounds | YEAST EXTRACT Concentration (g/100 g) | Quantity for 36 g/L of yeast extract (mg) | CDM Final concentration (mg · L$^{-1}$) | Ratio |
|---|---|---|---|---|
| Mineral contents | | | | |
| Calcium | 120 | 43.2 | — | — |
| Magnesium | 200 | 72 | 194 | 0.371 |
| Potassium | 3.3 | 1188 | 193 | 6.15 |
| Sodium | <0.5 | 440 | 2430 | 0.181 |
| Phosphorus | 1.8 | 988 | 1370 | 0.721 |
| Iron | 5 | 1800 | 2.14 | 0.841 |
| Nitrogen | — | — | 127 | — |
| Sulphate | — | — | 1508 | — |
| Vitamin contents | | | | |
| Biotin | 0.25 | 0.09 | 0.01 | 9 |
| Folic acid | 3.1 | 1.116 | 0.1 | 11.2 |
| Niacinamide | 68 | 24.5 | 2 | 12.2 |
| Ca Panthotenate | 30 | 10.8 | 0.8 | 13.5 |
| Riboflavin | 11.9 | 4.28 | 0.4 | 10.7 |
| Thiamine | 3 | 1.08 | 0.4 | 2.7 |
| Pyridoxamine | 2.3 | 0.8289 | 0.8 | 1.03 |
| VITAMINS: Average ratio yeast extract/CDM = 8.6 | | | | |
| Free amino acids contents | | | | |
| L-Alanine | 4.78 | 1721 | 200 | 8.605 |
| L-Arginine | 0.24 | 86.4 | 200 | 0.432 |
| L-Aspartic acid | 2.49 | 896 | 100 | 8.96 |
| L-Cysteine | — | — | 200 | — |
| L-Glutamic acid | 6.01 | 2160 | 200 | 10.8 |
| L-Glutamine | — | — | 50 | — |
| Glycine | 1.11 | 396 | 200 | 1.98 |
| L-Histidine | 1.80 | 648 | 200 | 3.24 |
| L-Isoleucine | 2.64 | 950 | 100 | 9.504 |
| L-Leucine | 4.34 | 1562 | 100 | 15.6 |
| L-Lysine | 3.08 | 1109 | 110 | 10.08 |
| DL-Methionine | 1.08 | 389 | 100 | 3.89 |
| L-Phenylalanine | 2.72 | 979 | 100 | 9.79 |
| L-Proline | — | — | 200 | — |
| DL-Serine | 2.35 | 846 | 100 | 8.46 |
| L-Threonine | 2.02 | 728 | 100 | 7.28 |
| L-Tryptophan | — | — | 200 | — |
| L-Tyrosine | 1.46 | 526 | 200 | 2.63 |
| L-Valine | 3.30 | 1188 | 100 | 11.88 |
| AMINO ACIDS: Average ratio yeast extract/CDM = 7.5 | | | | |

Example 5-Extension of Chemically Defined Media to Fermentation

Fed batch fermentation typically starts as a batch mode, and after a certain biomass concentration or substrate consumption, the fermentor is fed with the limiting substrate solution. As such, the nutrients medium must have a simple composition. The goal of this investigation was to develop a batch medium that identifies the limiting compounds and that does not affect the growth rate.

A) Development of Batch Medium for Fed Batch Process

In order to develop a defined fed batch medium, the limiting compounds were added one by one, and their effects on growth were evaluated.

First, the concentration of each vitamin in Table 2 was increased by a factor of 10. The vitamins were observed to be very important for the GBS growth. The cells immediately entered an exponential phase which lasted for 4 hours, reducing the doubling time from 42 minutes ($\mu_{max}$=1.00 h$^{-1}$) to 33 minutes ($\mu_{max}$=1.26 h$^{-1}$). After 3 hours, the cells had entered a deceleration phase for 2 hours before entering a stationary phase after 5 hours of culture. The final OD was 3.70, which was 50% higher than the previous trial. When vitamins were added to the batch medium, a positive effect was observed although they were not the only limiting compounds. The exponential growth phase was finished after 3 hours, but the glucose was still available at 6.3 g/L when the cells entered the deceleration phase.

The same study was performed by adding both 10× vitamins and 10× amino acids. For the fermentation involving 10× vitamins, the final OD was higher (OD$_{590\,nm}$=4.5). The exponential growth phase of the cells lasted for 4 hours. Glucose did not appear to be the limiting compounds since 4 g/L was again present when the cells entered the deceleration phase.

A study was also performed by adding 10× of potassium to the initial medium. In this case, a longer doubling time (t$_d$=49 minutes) and decreased final OD (OD$_{590\,nm}$=2.9) were observed when the cells were in the stationary growth phase. Increasing the initial potassium concentration by a factor of 10 had a negative effect on the growth. Thus, potassium needs to be added by feed or in smaller batches to avoid adding potassium to inhibitory levels.

According this study, the batch medium was composed of the same mineral contents as the initial chemically defined medium, but the concentration of vitamins and amino acids were increased by a factor of 10. Phosphate and carbon sources were added to the fed medium, but to determine the concentration of each component, a new comparison to the process using complex medium was necessary. Since 33 g/L of glucose were present in batch medium and 55 g/L were added during the linear addition, in order to add the same ratio of glucose and 10× of potassium, the fed medium was composed of: 275 g/L of glucose, 10.08 g/L of K$_2$HPO$_4$ and 14.8 g/L of KH$_2$PO$_4$. 500 mL of this solution were added to 1.2 L of the batch medium.

B) Development of Fed Batch Process

The strategy for the fed batch fermentation was to feed the growth limiting substrate at the same rate at which GBS consumed the substrate.

The nutrient feed rate influences fed batch fermentation by defining the growth rate of the microorganism and the effectiveness of the carbon cycle for product formation and minimization of by-product.

C) Growth Factors Requirements of Group B Streptococci

An organism, whether it is an autotroph or a heterotroph, may require small amounts of certain essential organic compounds for growth that the organism is unable to synthesize from the available nutrients.

Growth factors are required in small amounts by cells because they fulfill specific roles in biosynthesis. The need for a growth factor results from either a blocked or a missing metabolic pathway in the cells. They are organized in three categories: (1) purines and pyrimidines required for synthesis of nucleic acids; (2) amino acids required for the synthesis of proteins; and (3) vitamins needed as coenzymes and functional groups of certain enzymes.

The purpose of this investigation was to identify the growth factor requirements of the M781 strain of *Streptococcus agalactiae* to simplify the cultivating medium by reducing the number of compounds and to ensure a cost-efficient production process.

D) Amino Acid Requirement of the M781 Strain of *Streptococcus agalactiae*

By eliminating the amino acids one by one from the medium, L-Alanine, L-Aspartic acid, L-Glutamine and L-Proline were found to be dispensable (See FIG. 20 and Table 4). These amino acids always resulted in turbidity values of greater than 80% in the control culture. However, in the absence of any other amino acids, no growth occurred in the cultivating medium.

TABLE 4

Effect of omission of individual amino acids on growth of strain M781 of GBS in a CDM

| Amino acid | DO final | pH | Percentage of control growth | Required |
|---|---|---|---|---|
| All amino acids | 1.985 | 4.70 | | |
| L-Alanine | 1.675 | 5.23 | 85 | − |
| L-Arginine | 0.053 | 7.10 | 3 | + |
| L-Aspartic acid | 1.905 | 6.65 | 96 | − |
| L-Cystine | 0.001 | 7.25 | <1 | + |
| L-Glutamic acid | 0.162 | 6.65 | 8 | + |
| L-Glutamine | 2.085 | 4.87 | 100 | − |
| Glycine | 0.131 | 6.98 | 6 | + |
| L-Histidine | 0.052 | 7.02 | 3 | + |
| L-Isoleucine | 0.145 | 6.91 | 7 | + |
| L-Leucine | 0 | 7.22 | 0 | + |
| L-Lysine | 0.005 | 7.10 | <1 | + |
| L-Methionine | 0.045 | 7.06 | 2 | + |
| L-Phenylalanine | 0.008 | 7.20 | <1 | + |
| L-Proline | 2.015 | 4.74 | 100 | − |
| L-Serine | 0.401 | 6.44 | 20 | + |
| L-Threonine | 0 | 7.22 | 0 | + |
| L-Tryptophan | 0.133 | 6.96 | 7 | + |
| L-Tyrosine | 0 | 7.20 | 0 | + |
| L-Valine | 0 | 7.26 | 0 | + |

+: On the absence of the amino acid, M781 strain grew to 40% or less of the control
−: Growth was at least 40% of the control culture.

Satisfactory growth in the cultivating medium was obtained when 15 amino acids were present. Fermentation at a 2 L scale was performed to compare the M781 growth with only the essential amino acids. The growth was approximately the same magnitude when 19 amino acids were present. In both cases, no lag phase was observed, but a doubling time reduction from 62 minutes ($\mu_{max}$=0.672 h$^{-1}$) to 78 minutes ($\mu_{max}$=0.533 h$^{-1}$) was observed when the four amino acids were removed from the chemically defined medium.

The impact on the OD and cps production by the M781 strain when these 4 amino acids are omitted will be determined in the final process.

E) Vitamin Requirements of the M781 Strain of *Streptococcus agalactiae*

By eliminating the vitamins individually from the cultivating medium, calcium pantothenate and niacinamide were found to be indispensable (Table 5 and FIG. 21). In experiments where biotin, folic acid, pyridoxine, riboflavin and thiamine were omitted, the turbidity values were greater than 65%. When only pantothenate and niacinamide were added, the same final OD of the control was observed.

TABLE 5

Effect of omission of individual vitamins on growth of strain M781 of group B streptococci in a chemically defined medium

| Vitamins | DO final | pH | Percentage of control growth | Required |
|---|---|---|---|---|
| All vitamins present (Control culture) | 1.63 | 4.60 | — | – |
| Effect of omission of individual vitamins on growth | | | | |
| Biotin | 1.71 | 4.50 | 100 | – |
| Calcium panthotenate | 0.020 | 7.02 | <1 | + |
| Folic acid | 1.41 | 5.10 | 87 | – |
| Niacinamide | 0.22 | 6.90 | <1 | + |
| Pyridoxine | 1.55 | 4.65 | 95 | – |
| Riboflavin | 1.07 | 4.80 | 66 | – |
| Thiamine | 1.37 | 4.55 | 84 | – |
| Omission of 5 vitamins determined to not be required individually | | | | |
| Calcium panthotenate & Niacinamide | 1.58 | 4.53 | 96 | – |

+: On the absence of the amino acid, M781 strain grew to 40% or less of the control
–: Growth was greater than 40% of the control culture.

Batch fermentation based on the original cultivating medium was performed using only calcium pantothenate and niacinamide. After 8 hours of culture, the OD was 0.2. Thus, growth using only these two vitamins was not optimal. A new study was performed in 500 mL Erlenmeyer flasks by adding individually the vitamins that were not required as determined by the first shake flasks study to the medium already supplemented with calcium pantothenate and niacinamide. In this study, as observed in the study with only calcium pantothenate and niacinamide, turbidity values of each flask after 18 hours of culture was equal to the control culture.

Future experiments performed in the fermentor will enable the identification of the necessary vitamins for the growth of the M781 strain of *Streptococcus agalactiae*.

Example 6-Pilot-Scale Production

This Example confirms the teachings of the previous examples apply to the manufacturing scale production of serotype specific capsular polysaccharides of Streptococcal bacteria.

A) Culture of the Inoculum
i) Medium of Culture

The culture of the inoculum was performed in four 5 L-shake flasks sterilized by temperature (autoclave program no. 1 min./max., 40 min., 121° C., Table 6) containing 1 L of complex medium (17 g/L yeast extract Difco, 8 g/L $Na_2HPO_4.2H_2O$, 2 g/L $NaH_2PO_4.H_2O$, and 33 g/L monohydrated glucose, sterilized by 0.2 μm filtration with Nalgene filterware disposable systems, pH of 7.3±0.1 adjusted using 3M NaOH), 10 mL solution of vitamins (thiamine, riboflavin, pyridoxine HCl, and niacinamide, 0.05 g/L for each, diluted in 0.1M NaOH, sterilized by 0.2 μm filtration) and 5 mL of biotin solution (biotin 0.2 g/L, sterilized by 0.2 μm filtration) added just before inoculation.

TABLE 6

Correlation between the content of the autoclave and the specifications of sterilization

| Description of the contents of the autoclave | Number of the program | Organization (b) | Sterilization time (min) | Sterilization temperature (° C.) |
|---|---|---|---|---|
| Liquid | 7 | 2 or 4 | 30 | 121 |
| Glassworks | 4 | 1 min., 1 max. or 7 | 40 | 121 |
| Dirty | 8 | 3 | 130 | 124 |
| Air Filter (a) | 2 | NA | 40 | 121 |
| Liquid | 6 | 6 | 50 | 121 |
| Antifoam | 9 | 8 | 60 | 121 | ii) Inoculation of the Flasks and Conditions of Culture

Each flask was inoculated with 2.75±0.25 mL of working seeds extemporaneously defrosted from the −70° C. freezer. The culture was maintained at 35±1° C. with agitation 200±10 rpm in the incubator (IN-L0641) during 4±1 h. After this time, the biomass concentration was evaluated by measuring the OD at 590 nm and performing a Gram stain. If the value of $OD_{590\ nm}$ reached 1.2-0.6, and if the Gram stain conformed (only Gram positive cocci), the contents of the four flasks were pooled into a 5 L heat-sterilized (autoclave program no. 1 min./max.) bottle with connections to incubation line of the 300 L B. Braun Biotech/Chemap fermentor (ID VS-L0530).

iii) Key Variables of the Inoculum Preparation

The key variables of the inoculum preparation are described in Table 7 and Table 8.

TABLE 7

Controlled variables during the inoculum preparation

| Controlled Variables | Target Range |
|---|---|
| Initial pH of the medium | 7.3 ± 0.1 |
| Volume of working seed | 2.5-3.0 ml/flask |
| Temperature of incubation | 35 ± 1° C. |
| Agitation speed | 200 ± 10 rpm |

TABLE 8

Monitored variables during the inoculum preparation

| Monitored Variables | Target Range |
|---|---|
| Final $OD_{590\ nm}$ | 0.6-1.8 |
| GRAM | Only Gram positive cocci |
| Culture purity | No contaminant |
| Time of incubation | 3-5 hours | iv) Sterilization and Cleaning of Equipments

After use, the flasks and the 5 L bottle were heat sterilized (autoclave program no. 8, dirty cycle, see Table 6 for specifications) and cleaned.

B) Culture in the 300 L Fermentor
i) Preparation of the Medium and Equipment

The mechanical piping and gas filters of the empty 300 L fermentor were sterilized (program SEAL2 and EXFC2). The probes are then checked and calibrated. The pH probe was calibrated using two buffer solutions with values of pH 7 and 10. The correct application of the oxygen prove was verified by putting the probe in water with a gas-flow of nitrogen for the 0% point and air for the 100% point. Its calibration was performed inside the fermentor.

The basic medium (120 L, 2 g/L $Na_2HPO_4.2H_2O$, 1 mL for 120 L antifoam "PPG 2500") was formulated and sterilized in the 300 L fermentor (program FVES 2). During the sterilization, the 0% value of the oxygen prove was checked and reinitialized if necessary. After the cooling phases of the sterilization, the temperature of medium reached 36° C., and the basic medium was completed with 17 L of yeast extract 150 g/L, 9 L of glucose monohydrated 550 g/L, 2 L of a solution of vitamins (Thiamine, Riboflavin, Pyridoxine HCl, and Niacinamide, 0.05 g/L for each, diluted in 0.1M NaOH) all sterilized by 0.2 µm filtration. The 100% value of the oxygen prove was then calibrated after oxygenation of the medium. After 4 L of the inoculum were added, the final volume was 150 L at the beginning of the fermentation and the final concentration of yeast extract was 17 g/L and glucose was 33 g/L. These additions were performed on sterilizable lines with a peristaltic pump at maximal velocity (400 rpm) that corresponded to a flow of 550 mL/min.

ii) Fermentation Process and In-Process Controls

Before the inoculation, a biotin solution (1 L, 0.2 g/L biotin, sterilized by 0.2 µm filtration) was added. The 300 L fermentor was then inoculated using the 5 L bottle containing the content of the 4 flasks of inoculum.

The value of the following parameters were then checked, adjusted if necessary and automatically controlled during the process:

the temperature of the culture was controlled at 36±1° C.,
the overpressure inside the fermentor was set at 0.2 bar,
the pH was set at 7.3±0.1 and adjusted using 4M NaOH.
  There was no pH correction using an acidic solution because the pH value naturally decreased due to fermentation,
the initial stir was set at 50 rpm and the initial airflow was set at 20 L/min,
the level of foam in the fermentor was visually monitored and adjusted using antifoam PPG 2500 if necessary,
the dissolved oxygen tension (DOT) was set at 30% regulated in cascade by:
  the stir (range of values between 50 and 350 rpm)
  the airflow (range of values between 20 and 100 L/min)
  the oxygen flow (range of values between 0 and 100 L/min)

Samples were taken during the batch phase of the fermentation, two hours after inoculation, and the $OD_{590\ nm}$ was measured. Samples were taken every 15 minutes until the $OD_{590\ nm}$ reached 3. At that target OD, the first exponential fed batch addition was initiated using 3.6 L of a yeast extract solution (150 g/L), maintaining the population doubling time at 300 minutes.

Approximately 45 minutes after the first addition, the $OD_{590\ nm}$ was measured. Samples were taken every 15 minutes until the $OD_{590\ nm}$ reached 5. At that target OD, a second exponential fed batch addition was initiated using yeast extract solution (150 g/L), maintaining the doubling time at 50 minutes.

At the end of this second exponential fed batch addition, a pH-stat fed batch addition was performed. A monohydrated glucose solution (550 g/L) was added when the pH value exceeded 7.18. During this addition, a sample was taken every hour to measure the $OD_{590\ nm}$.

The fermentation finished approximately 3 hours after the last addition. The automatic controls of the parameters were then stopped. The stir was regulated at 100 rpm and the temperature at 30° C.

iii) Key Variables of the Fermentation Process

The key variables of the fermentation process are described in Table 9 and Table 10.

TABLE 9

Controlled variables during the fermentation

| Controlled Variables | Target Range |
|---|---|
| pH of the medium | 7.3 ± 0.1 |
| DOT setpoint | 30% |
| Temperature | 36 ± 1° C. |
| Overpressure | 0.2 bar |

TABLE 10

Monitored variables during the fermentation

| Monitored Variables | Target Range |
|---|---|
| Sterility check before inoculation | No contaminant |
| $OD_{590nm}$ for each sample | — |
| Culture purity at the end of the fermentation | Lack of contaminant |
| GRAM test | Only Gram positive cocci |
| Fermentation time | — | iv) Sanitization, Sterilization and Cleaning of the Equipments

Once the biomass was removed from the 300 L fermentor, the sanitization was initiated by adding 200 L of ROW into the fermentor. 3M NaOH was then added into the fermentor until the pH reached 11. The temperature was maintained at 80° C. for 30 minutes. After cooling to ambient temperature, the content of the fermentor was discarded into the waste tank located at the lower floor.

The sterilization was then performed by adding 200 L of ROW and activating the program (FVES 2) according to the Standard Operating Procedures (SOP). After the cooling phases of the sterilization, the pH and oxygen probe were removed from the fermentor and respectively stocked in a 3M KCl solution and ROW.

The fermentor was finally washed using 200 L of 1M NaOH, and stirred at 100 rpm for at least 30 minutes. This 200 L of NaOH were emptied into the killer tank after the washing and other 100 L of NaOH were placed in the fermentor via a spray ball so as to clean the upper part of the vessel. These 100 L were recirculated using a lobe pump for a minimum of 30 minutes. After this cleaning step, the fermentor was washed with ROW until the pH decreased to a range between 5 and 7.

C) Centrifugation of the Biomass i) Equipment Preparation

A tank containing physiological water (~100 L, 9 g/L NaCl, sterilized by 0.2 µm filtration) was connected to the transfer line that joined the 300 L fermentor to the Alfa-Laval centrifuge (ID CT-L0526). This water was used during the centrifugation to wash the biomass pellet. The transfer line was then heat sterilized like the separator and the collector tank of biomass. The preparation of equipments was performed before the end of the fermentation in order to begin the centrifugation as soon as possible after the end of the fermentation.

ii) Continuous Flow Centrifugation Process

The continuous flow centrifugation process was composed of the following cycle:

7 minutes of biomass centrifugation at a flow of 100 L/h, manually adjusted. The biomass was transferred from the fermentor to the separator through the transfer line by an excess pressure of 0.6 bar in the fermentor.
3 minutes of washing with physiologic water at a flow of 100 L/h, manually adjusted,
discharge of the pellet.

This cycle was usually repeated until the entire biomass was processed. The supernatant was not collected, but instead was fed to the waste tank. The pellet was collected in the tank (VS-L0536) during the process, and then transferred by an excess pressure of 0.3 bar through a silicone connection to a 100 L disposable sterile bag for chemical treatments.

iii) Key Variables of the Centrifugation

The key variables of the fermentation process are described in Table 11.

TABLE 11

Controlled variables during the centrifugation

| Controlled Variables | Target values |
| --- | --- |
| Pressure in the fermentor | 0.6 ± 0.1 bar |
| Flow | 100 L/h |
| Temperature of biomass | 30 ± 1° C. |
| Discharge time | 10 (7 + 3) min (a) |
| Temperature of the pellet | 30 ± 1° C. |
| Pressure of the supernatant | 3.0 ± 0.3 bar |

NOTE:
7 minutes of biomass centrifugation + 3 minutes of washing with physiological solution.

The monitored variables were the number of discharge, and the weight of collected biomass.

iv) Sterilization and Cleaning of the Equipments

After the centrifugation and transfer of the pellet to the disposable bag, the transfer line, the separator and the collector tank of biomass were heat sterilized and cleaned. The transfer line and separator were cleaned using 100 L of 1M NaOH at ambient temperature in the fermentor, and then transferred through the transfer line to the separator at a flow of 100 L/h. The collector tank was cleaned by circulating 20 L of 1M NaOH for 30 minutes in the tank through a spay ball so as to clean the upper part of the tank. After this cleaning step, the tank was washed with ROW until pH decreased to a range between 5 and 7.

D) Chemical Treatments of the Cellular Pellet i) Inactivation of the Cellular Pellet The chemical treatment of the cellular pellet inactivated the bacteria and enabled the release of cps from the bacteria. The treatment involved the addition of a 4M NaOH solution (through a tube with a peristaltic pump) to the pellet to obtain a theoretical concentration of 0.8M NaOH. The weight of the 4M NaOH added was obtained by dividing the biomass weight by four since 1 L weighed 1 kg. This step was performed in a 100 L disposable bag with an integrated stirrer system and disposed in the Levtech Sartorius System (ID AG-10645, thermostated balance and stirrer). The temperature was regulated to maintain the pellet at 37° C. and then stirred at 180 rpm for a specified period of time. 12 h were enough to inactivate the microorganisms. 36 h were suitable for releasing the cps from the bacterial capsule. In other experiments, 1 h was found to be enough to inactivate the microorganisms, while 24 h were suitable for releasing the cps from the bacterial capsule. Accordingly, a total time of 36 h or 24 h is suitable for this step.

ii) Key Variables of the Inactivation

The key variables of the fermentation process are described in Table 12.

TABLE 12

Controlled variables during the inactivation and release of the CPS

| Controlled Variables | Target values |
| --- | --- |
| Temperature of inactivation | 37 ± 0.1° C. |
| Agitation | 180 ± 10 rpm |
| Time | 36 ore | iii) Neutralization and Precipitation

Using silicone tubes with a peristaltic pump, a buffer solution of TRIS 1 M is added to obtain a final concentration equal to 0.1 M. The weight of TRIS to add is calculated by dividing the weight of the inactivated biomass by 9. The importance of this addition was to avoid pH variation in the pellet during the neutralization. Thus, the pH was controlled using a pH probe disposed in the disposable bag. 6M HCl was added to obtain a final pH value of 7.5-8.5.

2M $CaCl_2$ and 96% ethanol solutions were added to precipitate proteins and nucleic acids in the pellet. The final $CaCl_2$ concentration was 0.05M and ethanol was 30%. The weight of the 2M $CaCl_2$ added was obtained by dividing the weight of the neutralized biomass by 19, and the weight of ethanol 96% was obtained dividing the weight of the neutralized biomass with $CaCl_2$ by 3.1.

E) Microfiltration and Dialyze of the Treated Pellet

The biomass, chemically treated with $CaCl_2$ and 30% ethanol, underwent a microfiltration to recover the polysaccharides released in the supernatant and to eliminate the cellular residues, as well as the protein and nucleic acid precipitates.

i) Equipment Preparation

The microfiltration and dialysis were performed using a Sartorius Sartocon II plus holder with a disposable housing, and 4 Hydrosart cassettes 0.22 μm, 0.6 $m^2$ which represented a total surface area of 2.4 $m^2$. The system was tightened using a torque wrench of 90 Nm.

The cassettes were sanitized using 20 L of 1M NaOH, and sterilized by 0.2 μm filtration using a lobe pump to assure and regulate the pressure in the system. The retentate and permeate were then recirculated for 30 minutes in the following conditions:

Inlet pressure: 2.0±0.2 bar

Permeate valve closed for 5 minutes and then widely opened.

Distilled water was used to was the system until the pH reached 5-7, at which time the system was washed with 20 L of physiologic water (0.9 g/L NaCl, sterilized using a 0.2 μm filtration) to obtain a pH of 5-7 in the following conditions:

Inlet pressure: $P_{in}$=2.0±0.2 bar

Permeate pressure: $P_{perm}$=0 bar (open valve)

Retentate valve closed.

Prior to the microfiltration, the cassettes were conditioned with the dialysis buffer solution (34.77 g/L NaCl, 4.49 g/L TRIS, 10.93 g/L $CaCl_2$, pH adjusted to 7.8±0.1 using 6M HCl, WFI qsp 74.4% of final volume, 96% ethanol until final volume, sterilized by 0.2 μm filtration).

ii) Microfiltration and Dialyze

The exit tube of the disposable bag containing the treated biomass was connected to the inlet of the microfiltration housing. The retentate exit of the housing was connected to the disposable bag that contained the treated biomass to recirculate the processed biomass. The permeate exit was connected to a 200 L disposable sterile bag to collect the permeate.

The permeate valve was initially closed to let the pellet circulate in the microfiltration system. This valve was then opened, and the velocity of the lobe pump was controlled to obtain the following conditions:

Inlet pressure: $P_{in}$=2.0±0.2 bar

Permeate pressure: $P_{perm}$=0.6±0.1 bar

The biomass was concentrated 10 times, and the retentate was dialyzed against 3 volumes of buffer. To accurately determine the circulation in the microfiltration system, the weight of the retentate must not be less than 10 kg. As such, the retentate was concentrated until the biomass weighed 10±0.5 kg. The dialysis was then performed in successive steps. The weight of buffer solution used was calculated from the weight of the $CaCl_2$-ethanol mix divided by the theoretical concentration factor 10 and multiplied by the desired number of dialysis cycles.

iii) Sterilization by Filtration of the Permeate

The permeate was sterilized by filtration using a 2000 cm² Sartobran P 0.22 μm filter at the exit of the microfiltration system before collection into the 200 L disposable bag. The final product was stocked at ambient temperature before release into the purification department.

iv) Key Variables of the Microfiltration and Dialyze

The key variables of the microfiltration and dialyze are described in Table 13.

TABLE 13

Controlled variables during the microfiltration and dialyze

| Controlled Variables | Target values |
| --- | --- |
| $P_{in}$ | 2 ± 0.2° C. |
| $P_{perm}$ | 0.6 ± 0.1 bar |
| Retentate temperature | ≤20° C. |

The monitored variables are the permeate flow and the quantity of polysaccharides.

v) Equipment Cleaning

After the microfiltration, the inlet was connected to a tank containing 100 L of physiological water to wash the disposable cassettes and housing. Then, 20 L of 1M NaOH were used to sanitize the system, and the permeate and retentate were connected to the inlet for recirculation for 30 minutes while maintaining the following conditions:

Inlet pressure: $P_{in}$=2.0±0.2 bar

Permeate valve closed for 5 minutes and then widely opened.

The system and piping were then emptied, and washed with distilled water until the values of pH of the permeate and retentate ranged between 5 and 7. At that target pH, the system was disassembled.

An integrity test of the Sartobran P filter used to sterilized the permeate during the microfiltration and dialyze was performed before the release of the batch to the purification department.

F) Description of the Fermentation Profiles

The fermentation profiles of the pilot-scale experiments corresponding to the 3 GBS strains, M781 (serotype III), H36b (serotype Ib) and 090 (serotype Ia), were analyzed and compared with a control fermentation performed at laboratory-scale in a 30 L fermentor (B. Braun Biotech Biostat) using the H36b strain an identical process.

The $OD_{590\ nm}$ profiles of the 3 pilot-scale fermentations were very similar to each other, as well as to the control fermentation (see FIG. 22). The general profile of the microorganism's growth can be described in the following way: The batch phase lasted approximately 2.5 hours, and resulted in an $OD_{590\ nm}$ equal to 3. The first exponential fed addition of yeast extract solution (F1, 150 g/L) lasted approximately 45 minutes, and resulted in an $OD_{590\ nm}$ equal to 5. The second exponential fed addition of yeast extract solution (F2, 150 g/L) lasted approximately 45 minutes, and resulted in an $OD_{590\ nm}$ of approximately 10. The third pH-stat fed addition of monohydrated glucose (F3, 550 g/L) lasted approximately 3 hours.

G) Evaluation of the Growth Rates and Population Doubling Times

The growth rates (μ) and population doubling time ($t_d$) were evaluated during the 3 pre-test runs and the control fermentation. The values were reported in FIG. 22, as well as Table 14.

TABLE 14

Growth rate and population doubling time during the first series of the pre-trial runs.

| | Phase | M781 | H36b | 090 |
| --- | --- | --- | --- | --- |
| $\mu_{F1}$ (h⁻¹) | F1 | 0.59 | 0.96 | 0.54 |
| $td_{F1}$ (min) | | 71 | 43 | 88 |
| $\mu_{F2}$ (h⁻¹) | F2 | 1.01 | 0.89 | 0.65 |
| $td_{F2}$ (min) | | 41 | 47 | 64 |
| $\mu_{F3}$ (h⁻¹) | F3 | 0.20 | 0.23 | 0.23 |
| $td_{F3}$ (min) | | 203 | 182 | 182 |

The population doubling times during the first exponential fed addition of the pre-test runs, ranged between 43 and 77 minutes, which was at least as good as the reference fermentation. However, the desired population doubling time was 30 minutes. During the second exponential fed addition of the pre-test runs, the population doubling times ranged between 41 and 64 minutes, which was almost equal to the reference fermentation (55 minutes) and very near of the theoretical population doubling time (50 minutes).

H) Evaluation of the Production of Capsular Polysaccharides

The concentration of cps was evaluated at the end of fermentation using a colorimetric method based on the determination of the concentration of sialic acid compound of the cps. Based on this result, the cps quantity produced during the culture was calculated by multiplying the cps concentration by the final volume inside the fermentor (20 L for the reference fermentation, 215 L for the pilot-scale fermentor). The volumetric and specific productivity were also calculated as set out in the Fermentation Related Analytical Methods below. The values were reported in Table 15.

TABLE 15

Production and productivity of capsular polysaccharides

| | M781 | H36b | 090 |
| --- | --- | --- | --- |
| Final $OD_{590\ nm}$ | 18.15 | 25.1 | 14.0 |
| Final concentration of dried biomass (g/L) | 7.93 | 10.97 | 6.12 |
| Final concentration of cps (g/L) | 0.38 | 0.31 | 0.42 |
| Quantity of produced cps (g) | 82 | 67 | 90 |
| Ratio cps/biomass (%) | 4.8 | 2.8 | 6.8 |

I) Simplification of the Initial Process

The fermentation process was simplified in two ways to avoid potential variations in the scale-up and to decrease the risk of contamination in the fermentor.

First, the vitamin solutions containing thiamine, riboflavin, pyridoxine HCl, and niacinamide (each 0.05 g/L diluted in 0.1M NaOH and sterilized by 0.2 μm filtration) were removed from the medium of the inoculum and the fermentor. Indeed, the laboratory results had shown that the addition of these vitamins were not necessary for the growth of GBS and had a negligible impact on the cps production.

Second, the parameters of the fed phases during the fermentation were modified. The two exponential fed phases of yeast extract addition were replaced by two instantaneous additions, and the pH-stat fed phase of glucose addition was replaced by a linear addition. The first instantaneous addition (F1) comprised of adding a 3.6 L solution of yeast extract, 150 g/L using a peristaltic pump at a flow of 550 mL·min$^{-1}$ when the OD$_{590\ nm}$ was in the range between 2.5 and 3. The second instantaneous addition (F2) comprised of adding a 13.4 L solution of yeast extract, 150 g/L using a peristaltic pump at a flow of 550 mL·min$^{-1}$ when the OD$_{590\ nm}$ was in the range between 4.5 and 5. The third linear addition (F3) comprised of adding a 17 L glucose solution using a peristaltic pump at a flow of 95 mL·min$^{-1}$ when the OD$_{590\ nm}$ was in the range between 10 and 12.

J) Description of the Fermentation Profiles and Comparison with the Preceding Runs The fermentation profiles of this series of pre-test runs were analyzed and compared with the first series to ensure that the simplified process did not have any impact at the pilot-scale.

The OD$_{590\ nm}$ profiles of the 3 pilot-scale fermentations were very similar to each other, as well as to the general profile observed in the first series of pre-test runs (see FIG. 23). This similarity between the profiles highlights that the modifications of the process have no impact on the growth of the microorganisms as demonstrated at laboratory-scale.

K) Evaluation of the Growth Rates, Population Doubling Times and Production of Capsular Polysaccharides The growth rates and population doubling times of this series (Table 16) were also very similar to the first series of pre-test runs and no significant variations were observed.

TABLE 16

Growth rate and population doubling time during the second series of pre-trial runs

| | Phase | M781 | H36b | 090 |
|---|---|---|---|---|
| $\mu_{F1}$ (h$^{-1}$) | F1 | 0.80 | 0.66 | 0.67 |
| td$_{F1}$ (min) | | 52 | 63 | 63 |
| $\mu_{F2}$ (h$^{-1}$) | F2 | 0.92 | 0.76 | 0.92 |
| td$_{F2}$ (min) | | 45 | 55 | 45 |
| $\mu_{F3}$ (h$^{-1}$) | F3 | 0.18 | 0.31 | 0.19 |
| td$_{F3}$ (min) | | 232 | 133 | 219 |

The final cps concentration of these pre-test runs were in accordance with the previous pre-test runs. This suggests that there was no significant difference that resulted from the modifications at either the laboratory-scale or pilot-scale (see Table 17).

TABLE 17

Production and productivity of capsular polysaccharides

| | M781 | H36b | 090 | CJB111 |
|---|---|---|---|---|
| Final OD$_{590\ nm}$ | 18.25 | 20.7 | 17.5 | 25.5 |
| Final concentration of dried biomass (g/L) | 7.98 | 9.05 | 7.65 | 10.5 |
| Final concentration of cps (g/L) | 0.26 | 0.30 | 0.40 | 0.37 |
| Quantity of produced cps (g) | 56 | 65 | 86 | 86 |
| Ratio cps/biomass (%) | 3.2 | 3.3 | 5.2 | 3.4% |

L) Critical Steps of the Process and Definition of the Sampling Plan for the Process Verification During these two series of pilot-scale test runs, important in-process controls of the critical processing steps had been defined with their acceptance criteria and the associated sampling plan. The first in-process control was the OD$_{590\ nm}$ of the flask before inoculation that is preferably between 0.6 and 1.8 to avoid a potential lag phase at the beginning of the cultivation in fermentor as was observed at the laboratory-scale. The following in-process controls were relevant to the purity of the culture: Gram stains of the flasks medium were performed, as well as spreading on plates of the pooled bottle and the medium of the fermentor, to ensure the environment was free of contaminants. Another Gram staining and spreading on plates of the medium inside the fermentor was performed at the end of the culture to verify that there was no contamination during the process. The inactivation of the pellet was verified by spreading the pellet in 0.8 M NaOH on the plates after the 36 hours of inactivation. The other in-process controls described in Table 18 were used to calculate the cps purification yields. A profile of the parameter variations (P$_{O2}$, air flow, O$_2$ flow, stir, pH, temperature) was developed, and was a good indicator of the reproducibility of the fermentation process.

i) Description of the General Fermentation Profiles and Comparison with the Previous Runs The OD$_{590\ nm}$ profiles of this test run were very similar to each other, as well as to the general profile observed in the earlier test runs in this Example (see FIG. 24).

The growth rates and population doubling times of this series (Table 18) were comparable to the pre-test runs. More specifically, the growth rates of the addition phases of the 3 test runs were between the minimal and maximal values of the growth rates previously reported. However, the growth rates of the F3 phase during the culture of M781 and of the F2 phase during the culture of 090 were slightly below the minimum value previously reported (respectively 0.15<0.18, and 0.62<0.65) but without any incidence on the final values of OD$_{590\ nm}$ that were between the extreme values of OD$_{590\ nm}$ obtained during the earlier test runs (14 and 25.1 respectively for the first pre test run of the strain 090 and H36b).

TABLE 18

Growth rate and population doubling time during the series of test runs

| | Phase | M781 | H36b | 090 | CJB111 |
|---|---|---|---|---|---|
| $\mu_{F1}$ (h$^{-1}$) | F1 | 0.82 | 0.85 | 0.63 | 0.72 |
| td$_{F1}$ (min) | | 51 | 49 | 60 | 58 |
| $\mu_{F2}$ (h$^{-1}$) | F2 | 0.92 | 0.96 | 0.62 | 1.16 |
| td$_{F2}$ (min) | | 45 | 43 | 67 | 36 |
| $\mu_{F3}$ (h$^{-1}$) | F3 | 0.15 | 0.21 | 0.17 | 0.27 |
| td$_{F3}$ (min) | | 281 | 201 | 242 | 158 |

The final concentration and quantity of cps of the test runs were higher than the pre-test runs when the results each of the 3 strains were compared (see Table 19). The value for the H36b stain was between the values previously obtained for the other strains (0.35 L$^{-1}$ between 0.26 and 0.42 respectively obtained for the first pre-test run of 090 and the second one of M781). The values obtained for the strains M781 and 090 were higher than expected. As such, the cps to biomass ratios for these stains exceeded 10%, which implied that the purification would be facilitated.

TABLE 19

Production and productivity of capsular polysaccharides

|  | M781 | H36b | 090 | CJB111 |
|---|---|---|---|---|
| Final OD$_{590\,nm}$ | 17.2 | 20.9 | 16.5 | 26.55 |
| Final concentration of dried biomass (g/L) | 7.52 | 9.12 | 7.21 | 11.7 |
| Final concentration of cps (g/L) | 1.01 | 0.35 | 0.82 | 0.42 |
| Quantity of produced cps (g) | 216 | 75 | 177 | 90.3 |
| Ratio cps/biomass (%) | 13.4 | 3.8 | 11.4 | 3.6 |

Analysis of the Critical In-Process Controls

The first in-process control was the OD$_{590\,nm}$ of the flask before inoculation, and ranged between 0.80 for strain 090 and 1.50 for strain M781. No lag phase at the beginning of the culture in fermentor was observed. The purity analysis of the flasks culture were confirmed by Gram stain which revealed only Gram positive cocci, and the pooled bottle as well as medium from the fermentor at the end of the culture similarly only revealed Gram positive cocci. The inactivation of the pellet in 0.8 M NaOH was spread on the plates after the 36 hours of inactivation.

The profiles of the variations of parameters (P$_{O2}$, air flow, O$_2$ flow, stir, pH, temperature) during the 4 test runs were comparable to the general profile that was reported in the pre-test runs.

TABLE 20

Results from Pilot Runs (Polysaccharide Purification)

| Parameter | Unit | Limit | Ia Test Run | Ib Test Run | III Test Run | V Test Run |
|---|---|---|---|---|---|---|
| Final product weight | g | N/A | 25.9 | 21.1 | 28.9 | 15.5 |
| TGA (dry weight) | %, w/w | N/A | 93.6 | 90.9 | 91.9 | 90.2 |
| Saccharide titer | μg/mg* | >850 | 1030 | 989 | 959 | 1025 |
| Proteins | μg/mg* | <10 | <5 | <5.5 | <5 | <5 |
| Nucleic acids | μg/mg* | <10 | <0.0006 | <0.002 | 0.007 | <0.00006 |
| Group Polysaccharide | μg/mg* | <10 | <2 | <1.8 | <2 | <2 |
| Free sialic acid | %, m/m | <1 | <0.8 | <0.9 | <0.9 | <0.15 |
| Structural conformity | N/A | conform | conform | conform | conform | conform |
| N-acetylation degree | % | >80 | 92 | 92 | 90 | 103 |
| Kd | N/A | N/A | 0.481 | 0.330 | 0.463 | 0.401 |
| Endotoxins/saccharide | UI/μg | <1 | <0.0005 | <0.001 | 0.0007 | 0.0003 |
| Antifoam | μg/mg | <10 | <10 | <10 | <10 | nd |

*μg/mg of dry weight

TABLE 21

Results from Pilot Runs (Activation/Conjugation)

| | Unit | Limit | Ia Test Run | Ib Test Run | III Test Run | V Test Run |
|---|---|---|---|---|---|---|
| Worked Polysacchar. | g | N/A | 6.64 | 7.19 | 7.0 | 5.08 |
| Worked Product*** | L | N/A | 51 | 68 | 49 | 66 |
| Final Product | Kg | N/A | 3.50 | 3.89 | 4.60 | 1.69 |
| Saccharide concentr. | μg/mL | N/A | 1133 | 999 | 489 | 781 |
| Protein concentration | μg/mL | N/A | 427 | 594 | 384 | 678 |
| Glycosylation Degree | N/A | (1) | 2.7 | 1.7 | 1.3 | 1.2 |
| Free Protein | %, w/w | <5 | <5 | <3 | <5 | <2 |
| Free Saccharide | %, w/w | <25 | 16.2 | 8.9 | 19.6 | <1 |
| Free Sialic acid | %, m/m | <1 | <0.3 | <0.3 | <0.7 | N/A |
| pH | N/A | 6.9-7.5 | 7.2 | 7.1 | 7.2 | 7.2 |
| Identity/Conformity* | N/A | positive | positive | positive | positive | positive |
| NaCNBH3 | ppm | <2 | <2 | <2 | <2 | <2 |
| Kd | N/A | N/A | 0.212 | 0.220 | 0.351 | 0.40 |
| Endotoxins/saccharide | UI/mg** | N/A | 1 | 0.3 | 0.1 | 0.24 |
| Total saccharide | g | N/A | 4.0 | 4.4 | 2.3 | 1.3 |

(1): Ia and Ib: 1.0-3.5; III: 0.5-2.5; V: 0.5-3.0

*by NMR;

**mg of saccharide;

***as equivalent fermentation volume

TABLE 22

Forecast Yields for 1000L upscale (based on Pilot Processes)

| Serotype | Polysaccharide expected form a 1000 L batch (according to Pilot Processes) (g) | Purified Polysaccharide expected from a 1000 L culture batch (according to Pilot Processes) (g) | Glycoconjugate Saccharide expected from a 1000 L culture batch (according to Pilot Processes) (g) | Number of 20 µg doses expected from a 1000 L batch (according to Pilot Processes) (Million) | Forecast Number of doses expected from optimized processes (Million) |
|---|---|---|---|---|---|
| Ia | 370 | 140 | 84 | 4.2 | >8 |
| Ib | 370 | 110 | 62 | 3.1 | >6 |
| III | 370 | 125 | 38 | 1.9 | >4 |
| V | 370 | 75 | 20 | 1.0 | >3 |

Fermentation Related Analytical Methods

Determination of Biomass. During fermentation, biomass content is monitored by measurement of the optical density of the culture at a wavelength of 590 nm. Dilutions of the sample have to be prepared in order to read a value of absorbance within the interval 0.300-0.600. Wet weight of harvest is determined after centrifugation for 25 min at 16000×g.

Determination of Capsular polysaccharide content. The serotype-specific capsular polysaccharide of GBS is made of a repeating unit of the following saccharides: NANA: N-acetyl-neuraminic acid or sialic acid; GLUC glucose; GAL: galactose and NAGA: N-acetyl-glucosamine. Sialic acid content can be determined using the chemical method set-up by Svennerholm (Svennerholm L., (1957) Biochem. Biophys. ACTA 24:604-611). The composition of the repeating unit differs with serotype, so a different correction factor has to be applied for each serotype.

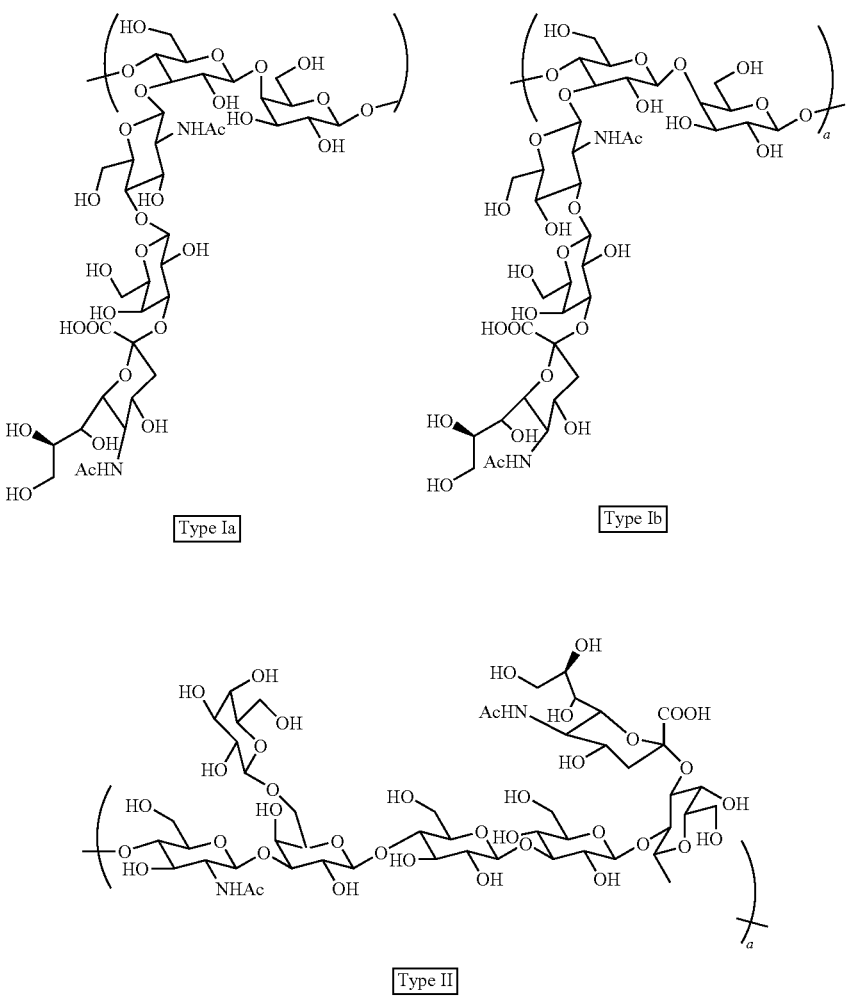

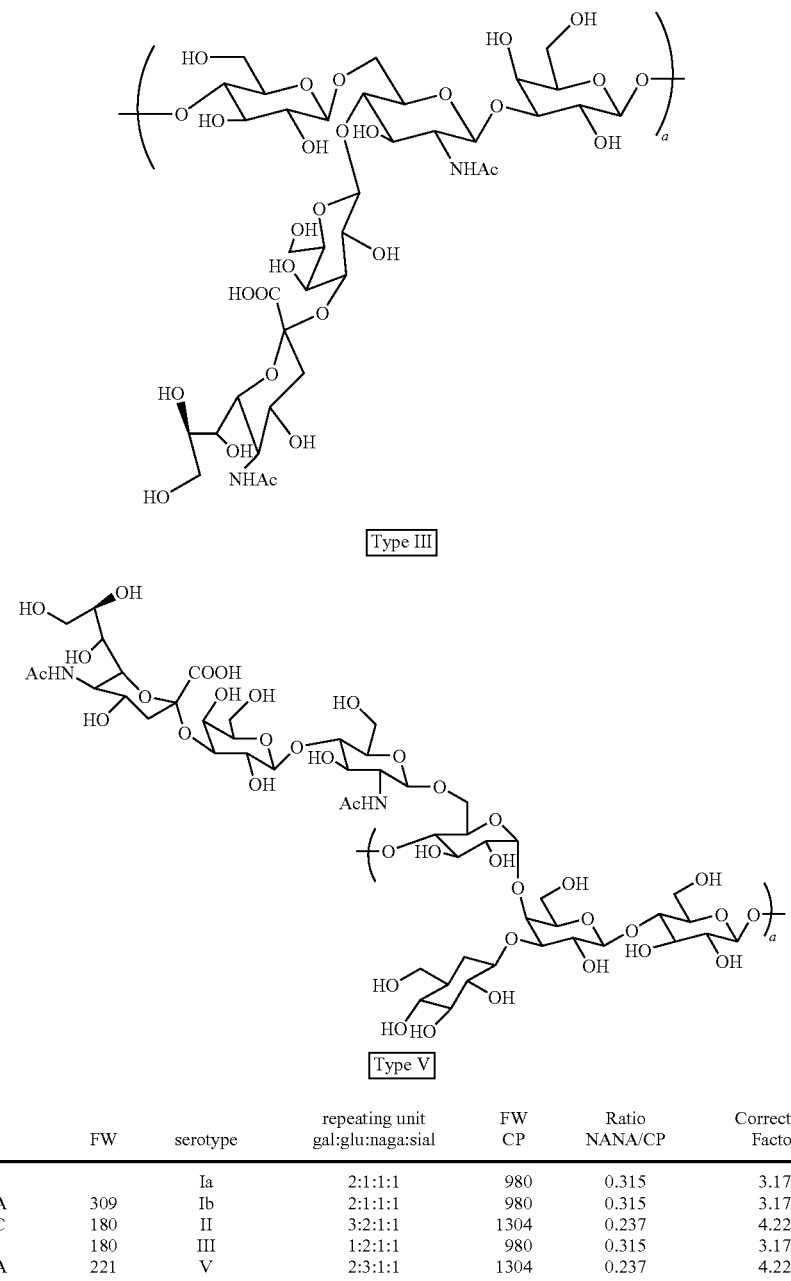

[Type III]

[Type V]

| Sugar | FW | serotype | repeating unit gal:glu:naga:sial | FW CP | Ratio NANA/CP | Correction Factor |
|---|---|---|---|---|---|---|
|  |  | Ia | 2:1:1:1 | 980 | 0.315 | 3.17 |
| NANA | 309 | Ib | 2:1:1:1 | 980 | 0.315 | 3.17 |
| GLUC | 180 | II | 3:2:1:1 | 1304 | 0.237 | 4.22 |
| GAL | 180 | III | 1:2:1:1 | 980 | 0.315 | 3.17 |
| NAGA | 221 | V | 2:3:1:1 | 1304 | 0.237 | 4.22 |

Sample Preparation.

A quantity of 10 OD.mL is centrifuged (16000×g, 5 min, 4° C.). [standardise]

Wash the pellet with 1 mL of PBS and centrifuge (16000× g, 5 min, 4° C.) [wash]

To the pellet is added 500 mcL of NaOH (2N, 65° C., 1 h) [hydrolise]

After 1 hour, neutralize with 500 mcL HCl (2N, 4° C.) [neutralise]

Cell debris are removed by centrifugation (16000×g, 30 min, 4° C.). [purify]

Supernatant is sterilized by filtration (0.22 micron) [sterilise]

100 mL are diluted with 900 mL of $H_2O$ [dilute]

Standard curve preparation. A culture of strain COH1-13 (unencapsulated) is prepared in the same way as the samples. The dilution step is characterised with the addition of a known quantities of sialic acid stock solution to obtain final concentrations of 1, 5, 10, 15, 20 and 30 mg/mL. (100 mL supernatant+x mL sialic acid SS+900-x mL $H_2O$)

Chemical reaction. Starting Materials for the reagent: A=Resorcinol (2%, $H_2O$); B=$CuSO_4.5H_2O$ (0.1M, $H_2O$). Fresh reagent is mixed as follows: 10 mL A+0.25 mL B+$H_2O$ ($V_{fin}$=20 mL)->+HCl (37%)=100 mL). Reagent once mixed is stable for 1 week at 4° C. Add 1 mL of reagent to 1 mL of diluted sample, incubate for 40 min at 90° C., read absorbance at 564 nm.

Quantification. Determine quantity of NANA in sample using standard curve.

Apply correction factor of the serotype. [specific CP content (mg/LOD)]

Multiply with OD of culture. [volumetric CP content (mcg/mL or mg/L)]

Multiply with volume of harvest [total CP produced (mg)]

Example 6-Purification

This example shows an exemplary purification protocol which provides much higher levels of purity than have previously been possible for capsular polysaccharides Isolation and Purification of GBS Type Ia, Ib, III and V Polysaccharides Native GBS Type V polysaccharide were extracted and purified from bacteria using the process steps:

Bacterial fermentation: GBS Type V strain (e.g., CJB111) was grown complex medium. Any method of culture may be used, though fermentative culture as disclosed herein is preferred.

Inactivation of fermentation biomass and polysaccharide extraction (base treatment): If necessary, the biomass may be heated to bring it to room temperature. Sodium hydroxide (4 M) was added to the recovered biomass to a final concentration of 0.8 M and mixed to homogeneity. The suspension was subsequently incubated at 37° C. for 36 hours with mixing.

Neutralization of biomass: After extraction with base treatment, TRIS-base 1 M (121.14 g/mol) was added to a final concentration of 50 mM (52.6 mL per 1 L of base mixture) and the suspension was mixed to homogeneity. The pH of the mixture was adjusted to 7.8 with HCl (6 M) (1:1 dilution of the concentrated acid).

Alcohol precipitation: 2 M $CaCl_2$ was added to a final concentration of 0.1 M (52.6 mL per 1 L of neutralized mixture) and the suspension was mixed to homogeneity. Ethanol (96% (v/v)) was added to a final concentration of 30% (v/v) ethanol (428 mL per 1 L) and the suspension was mixed to homogeneity.

Tangential microfiltration: The supernatant from the alcohol precipitation was recovered by a tangential microfiltration on a 0.2 µm cellulose membrane (Sartorius Sartocon Hydrosart 0.1 m2) against a dialysis buffer comprising: NaCl (0.5 M)+$CaCl_2$ (0.1 M)+Ethanol 30% (v/v) buffered at pH 7.8. Ten dialysis volumes were used for the microfiltration. The permeate was filtered using a 0.45/0.2 µm filter to sterilize the permeate (Sartorius Sartobran filter). Note: as an alternative, the retentate can be clarified by centrifugation (retaining the supernatant fluid) and stored at 2-8° C.

Tangential diafiltration 30 kDa: To eliminate particulate matter formed during storage, the material was filtered with a 0.45/0.2 µm filter (Sartobran filter). The material was diafiltered on 30 kDa cellulose membrane (Sartorius Sartocon Hydrosart 0.1 m²) against 25 volumes of TRIS 50 mM+NaCl 0.5 M buffered at pH 8.8 and then against 10 volumes of $Na_2CO_2$ 0.3 M+NaCl 0.3 M buffered at pH 8.8. Pressure setting: $\Delta P[P_{in}-P_{out}]<0.7$ bar, $TMP[(P_{in}+P_{out})/2]>1.0$ (e.g., $P_{in}=2$ bar, $P_{out}=1$ bar). The retentate was filter sterilized using a 0.45/0.2 µm filter (Sartorius Sartobran filter). The material was then stored at 2-8° C. until needed (max 15 days).

Depth filtration: A depth filtration on CUNO BioCap 2000 1300 cm² capsule (or CUNO Z-Carbon R52SP filter for smaller scale preparation) was applied to remove residual protein contaminants. The number of capsules or filters used was defined on the base of the ratio: 0.5 cm² per mg of residual proteins.

Example with CUNO capsules: Using a peristaltic pump, the capsule was washed with >9.0 L of $Na_2CO_3$ 300 mM+NaCl 0.3 M buffered at pH 8.8 at flow rate of 350±50 mL/min. If the volume of the material was less than 1.6 L, the suspension was diluted to the right volume with $Na_2CO_3$ 0.3 M+NaCl 0.3 M buffered at pH 8.8. The material was filtered, and the filter was subsequently washed with 2.5 L of $Na_2CO_3$ 0.3 M+NaCl 0.3 M buffered at pH 8.8. The material obtained from the different capsules was combined. The collected material was filtered on new capsules (⅕ of the previous number) and washed with 2.5 L of $Na_2CO_3$ 0.3 M+NaCl 0.3 M buffered at pH 8.8. The material was filter sterilized using a 0.45/0.2 µm filter (Sartorius Sartobran filter). The material was stored at 2-8° C. until needed (max 15 days).

Re—N-Acetylation of polysaccharide: The material was diluted to 2 mg of polysaccharide/mL (estimated by resorcinol sialic acid assay) with $Na_2CO_3$ (0.3)M+NaCl (0.3 M) buffered at pH 8.8. Stock solution of acetic anhydride was prepared at the following proportions: 8.3 mL of acetic anhydride+8.3 mL of Ethanol 96%+983.4 mL of water. Fresh acetic anhydride stock solution was added to the polysaccharide solution diluted to 2 mg/mL to a ratio of >22:1 acetic anhydride:polysaccharide repeating unit. The material was incubated with mixing for 2 hours at room temperature. The pH was checked at the end of 2 hours to verify that is was ~8.8.

Purification of the re-N-acetylated polysaccharide by tangential diafiltration 30 kDa: To eliminate the particulate formed during the storage, the material is filtered against a 0.45/0.2 µm filter (Sartobran filter). Note: clarification by centrifugation is also acceptable. The material was dia-filtered on 30 kDa cellulose membrane (Sartocon Hydrosart 0.1 m2) against 13 volumes of sodium acetate 10 mM with a pressure setting of $\Delta P[P_{in}-P_{out}]<0.7$ bar, $TMP[(P_{in}+P_{out})/2]>1.0$ (e.g., $P_{in}=2$ bar, $P_{out}=1$ bar). The material was filter sterilized with a 0.45/0.2 µm filter (Sartorius Sartobran filter). The material was stored at 2-8° C. until needed (max 15 days).

Recovery of polysaccharide: $CaCl_2$ 2 M was added to obtain a final concentration of 0.1 M (52.6 mL per 1 L of neutralized mixture) and the suspension was mixed to homogeneity. Ethanol (96% (v/v)) was added to a final concentration of 80% (v/v) (ratio of 4 L per 1 L of solution) and the suspension was mixed to homogeneity. The precipitate was washed (2-3 times) with fresh ethanol 96% (~50 mL each). The precipitate was collected by centrifugation at 3000×g for 10 min and dried to a powder under vacuum.

Analytical Methods

Wet-chemical assays: The saccharide content was determined by the sialic acid wet-chemical assay (Svennerholm, L. Biochem. Biophys. Acta 1957, 24, 604). The sample was hydrolyzed in HCl at 80° C. 90 minutes, neutralized with NaOH and injected in a DIONEX™ system. Data are processed by CHROMELEON™ Software. The saccharides were eluted using a seven minute linear gradient of 90:10 to 60:40 0.1 M NaOH, 0.1 M NaAcetate:0.1 M NaOH, 0.5 M $NaNO_3$ on a CarboPac PA1 column with PA1 guard at a flow rate of 1.0 ml/min.

Free sialic acid was determined by injecting the polysaccharide sample solubilized in water at 1.0 mg/ml without hydrolyzing the sample. In this way it was possible to separate free from bound sialic acid. FIG. 29 is an overlay of a polysaccharide sample and standard (gray line) at 0.5 µg/ml. In the polysaccharide sample, free sialic acid is not detected. The peak in the regeneration step was the polysaccharide not hydrolyzed. Free sialic acid is an important parameter because it is related with immune response.

The residual protein content was determined by a MicroBCA™ commercial kit (Pierce). The residual nucleic acid content was determined following the method published by Sheldon, E. L.; et al. Biochem. Biophys. Res. Comm. 1989, 156(1), 474.

The residual Group B polysaccharide content determined by determining the rhamnose residues and using a method based on HPAEC-PAD analysis. Rhamnose is a specific saccharide in the group B carbohydrate that is not found in the Type polysaccharides and it was used to determine the concentration of contaminant carbohydrate residue after capsular polysaccharide purification. The sample assayed was purified GBS type III polysaccharide in FIG. 30. The sample did not present a rhamnose peak indicating the absence of other carbohydrate contaminants. The gray chromatogram was obtained by adding rhamnose standard to the sample. Samples and standards were hydrolyzed in TFA 2N at 100° C. for 3.0 hours, then evaporated in SpeedVac and reconstituted with 450 µl of H2O. Rhamnose standard curve range is 1.0-10.0 µg/ml. The chromatographic conditions were: a Carbo-Pac PA1 column with PA1 guard with a flow rate of 1.0 ml/min of NaOH 12 mM for 15 minutes followed by 5 minutes of regeneration with NaOH 500 mM and then re-equilibration in NaOH 12 mM for 25 minutes.

Chromatographic analysis: The approximate molecular weights of the Type polysaccharides were estimated by HPLC on a SUPEROSE™ 6 HR 10/30 column (GE Healthcare) equilibrated with PBS and calibrated with dextrans.

NMR analysis: Samples of purified polysaccharides were prepared by dissolving the powder in 1 mL of deuterium oxide (D2O, Aldrich) to a uniform concentration. Aliquots (750 µL) of the samples were transferred to 5-mm NMR tubes (Wilmad). $^1$H NMR experiments were recorded at 25° C. on Bruker 600 MHz spectrometer, and using 5-mm broadband probe (Bruker). For data acquisition and processing, XWIN-NMR software package (Bruker) was used. 1-D proton NMR spectra were collected using a standard one-pulse experiment with 32 scans. The transmitter was set at the HDO frequency (4.79 ppm). $^1$H NMR spectra were obtained in quantitative matter using a total recycle time to ensure a full recovery of each signal (5× Longitudinal Relaxation Time T1).

2-D homo- and hetero-correlation NMR spectrum were recorded to assign the 1-D proton NMR profiles (See, FIGS. 25-28). The peak assignment was also confirmed by comparison with published data (Michon, F.; Chalifour, R.; Feldman, R.; Wessels, M.; Kasper, D. L.; Gamian, A.; Pozsgay, V.; Jennings, H. J. Infect Immun 1991, 59, 1690 and related papers).

Results and Discussion

This procedure provides a novel simple, fast and effective method for purifying Type polysaccharides from streptococcal bacteria. It is advantageous that the process does not involve the use of DNAse, RNAse and protease treatments. The products are recovered in high yields, whereas all the main potential contaminants (proteins, nucleic acids and Group B polysaccharide) are reduced lower than 1% w/w. The new purification method can be used for manufacturing of clinical and commercial materials derived from these capsular polysaccharides.

The product purity was confirmed as reported in Table 24.

TABLE 24

Summary of the product purity of GBS Type Ia, Ib, III and V polysaccharides

| PS Type | PS Content[1] (µg/mg powder) | Protein Residual Content[2] (µg/mg powder) | Nucleic Acid Residual content[3] (µg/mg powder) | Group B PS Residual Content[4] (µg/mg powder) |
|---|---|---|---|---|
| Type Ia 090 | 935 | 3 | <10 | <10 |
| Type Ib H36B | 757 | 9 | <10 | <10 |
| Type III M781 | 746 | 1 | <10 | <10 |
| Type V CJB111 | 785 | 3 | <10 | <10 |

([1] Sialic acid wet-chemical assay; [2] MicroBCA protein commercial kit assay; [3] Nucleic acid assay; [4] Group B polysaccharide assay).

Average molecular weights for the Type polysaccharides, estimated by Size Exclusion Chromatography, were ~200 kDa for the Type Ia, Ib and ~100 kDa for the Type III and V. The structural identity of GBS Type Ia, Ib, III and V polysaccharide was confirmed by 1H NMR spectroscopy (FIGS. 25-28).

Example 7-Purification

This example shows a further exemplary purification protocol which provides much higher levels of purity than have previously been possible for capsular polysaccharides.

Isolation and Purification of GBS Type Ia, Ib, III and V polysaccharides

Native GBS Type V polysaccharide were extracted and purified from bacteria using the following process steps:

Bacterial fermentation: GBS Type V strain (e.g., CJB111) was grown in complex medium. Any method of culture may be used, although fermentative culture as disclosed herein is preferred.

Inactivation of fermentation biomass and polysaccharide extraction (base treatment): If necessary, the biomass may be heated to bring it to room temperature. Sodium hydroxide (4 M) was added to the recovered biomass to a final concentration of 0.8 M and mixed to homogeneity. The suspension was subsequently incubated at 37° C. for 36 hours with mixing.

Neutralization of biomass: After extraction with base treatment, TRIS-base 1 M (121.14 g/mol) was added to a final concentration of 50 mM (52.6 mL per 1 L of base mixture) and the suspension was mixed to homogeneity. The pH of the mixture was adjusted to 7.8 with HCl (6 M) (1:1 dilution of the concentrated acid).

Alcohol precipitation: 2 M $CaCl_2$ was added to a final concentration of 0.1 M (52.6 mL per 1 L of neutralized mixture) and the suspension was mixed to homogeneity. Ethanol (96% (v/v)) was added to a final concentration of 30% (v/v) ethanol (428 mL per 1 L) and the suspension was mixed to homogeneity.

Tangential microfiltration: The supernatant from the alcohol precipitation was recovered by a tangential microfiltration on a 0.2 µm cellulose membrane (Sartorius Sartocon Hydrosart 0.1 m2) against a dialysis buffer comprising: NaCl (0.5 M)+$CaCl_2$ (0.1 M)+ethanol 30% (v/v) buffered at pH 7.8. Ten dialysis volumes were used for the microfiltration. The permeate was filtered using a 0.45/0.2 µm filter to sterilize the permeate (Sartorius Sartobran filter). Note: as an alternative, the retentate can be clarified by centrifugation (retaining the supernatant fluid) and stored at 2-8° C.

Tangential diafiltration 30 kDa: To eliminate particulate matter formed during storage, the material was filtered with a 0.45/0.2 µm filter (Sartobran filter). The material was purified by a first diafiltration step using a 30 kDa cellulose membrane (Sartorius Sartocon Hydrosart 0.6 m$^2$) against 20 volumes of TRIS 50 mM, NaCl 0.5 M at pH 8.8 and then against 10 volumes of Na phosphate 10 mM at pH 7.2. Pressure setting: $P_{in}$=3 bar, $P_{out}$=1 bar). The retentate of the first diafiltration step was diluted to 10 kg and then treated with an acetic acid/sodium acetate solution at pH 4.0 (2 L). The suspension obtained from this treatment was filtered using GFPlus 0.45 µm capsules (Sartorius) in order to remove precipitate and then filtered once again using a 0.2 µm membrane filter (Sartobran Sartorius). The pH was maintained at a value of 4.4±0.1. The filtered product was then diafiltered again against Na$_2$CO$_3$ 0.3M, NaCl 0.3 M at pH 8.8. After further filtration using a 0.45/0.2 filter, the material was stored at 2-8° C. (for a maximum of 15 days) until needed.

Adherent filtration with CUNO capsules: Filtration was carried out using CUNO Z-Carbon R53SLP8 cartridges. Using a peristaltic pump, the cartridges were assembled in a dedicated holder and then washed with >20.0 L of WFI at a flow rate of 580±40 mL/min. The cartridges were then washed with >20.0 L of Na$_2$CO$_3$ 0.3 M, NaCl 0.3 M at pH 8.8 at the same flow rate. If the volume of the material was less than 20 L, then it was diluted to the desired volume with Na$_2$CO$_3$ 0.3 M, NaCl 0.3 M buffered at pH 8.8. The material was then filtered and collected in a sterile bag. The holder was filled with 20 L of Na$_2$CO$_3$ 0.3 M, NaCl 0.3 M at pH 8.8 and filtration conducted to collect 6 L of filtered product. The material was then filtered using a 0.45/0.2 µm filter. The material was stored at 2-8° C. (for a maximum of 15 days) until needed.

Re—N-acetylation of polysaccharide: Z-Carbon filtered material was treated with an acetic anhydride/ethanol solution to allow re-N-acetylation. The reactive mixture needed to treat 1 L of polysaccharide solution was prepared using the following proportions: 4.15 mL of acetic anhydride+4.15 mL of ethanol 96%. The reaction solution was incubated under stirring for 2 hours at room temperature. The pH was checked at the end of 2 hours to verify that it was about 7.

Purification of the re-N-acetylated polysaccharide by tangential diafiltration 30 kDa: The material was diafiltered on 30 kDa cellulose membranes (0.1 m$^2$ Sartocon Hydrosart) against 13 volumes of potassium phosphate 10 mM at pH 7.2 with a pressure setting of $\Delta P[P_{in}-P_{out}]$<0.7 bar, TMP[($P_{in}$+$P_{out}$)/2]>1.0 (e.g., $P_{in}$=2 bar, $P_{out}$=1 bar). The material was then filtered using a 0.45/0.2 µm filter. The material was stored at −20° C. until needed.

ADDITIONAL REFERENCES

1. Ada & Isaacs (2003) *Clin Microbiol Infect* 9:79-85.
2. Shen et al. (2001) *Vaccine* 19:850-61.
3. Palazzi et al. (2004) *J. Infect. Dis.* 190:558-64.
4. Merritt et al. (2000) *J. Biotech.* 81:189-97.
5. Dassy & Fournier (1996) *Infect. Immunol.* 64:2408-14.
6. Suarez et al. (2001) *Appl. Env. Microbiol.* 67:969-71.
7. Wicken et al. (1983) *J. Bact.* 153:84-92.
8. Paoletti et al. (1996) *Infect. Immunol.* 64:1220-26.
9. Ross et al. (1999) *J. Bact.* 181:5389-94.
10. Paoletti et al. (1999) *J. Infect. Dis.* 180:892-95.
11. Terleckyj et al. (1975) *Infect. Immunol.* 11:649-55.
12. Willett & Morse (1966) *J. Bacteriol.* 91(6):2245-50.
13. Merritt et al. (1978) *J. Clin. Microbiol.* 8:105-07.
14. WO95/29986.
15. WO98/32873.
16. Frash (1990) p. 123-145 of *Advances in Biotechnological Processes* vol. 13 (eds. Mizrahi & Van Wezel).
17. EP 0072513.
18. UK 0502096.1 (patent application); WO2006/082527.
19. U.S. Pat. No. 6,248,570.
20. Deng et al. (2000) *J. Biol. Chem.* 275:7497-7504.
21. Inzana (1987) *Infect. Immun.* 55:1573-79.
22. Ramsay et al. (2001) *Lancet* 357(9251):195-96.
23. Lindberg (1999) *Vaccine* 17 Suppl. 2:S28-36.
24. Buttery & Moxon (2000) *J R Coll Physicians Land* 34:163-68.
25. Ahmad & Chapnick (1999) *Infect. Dis. Clin. North Am.* 13:113-33, vii.
26. Goldblatt (1998) *J. Med. Microbiol.* 47:563-7.
27. EP 0477508.
28. U.S. Pat. No. 5,306,492.
29. WO98/42721.
30. Dick et al. in *Conjugate Vaccines* (eds. Cruse et al.) Karger, Basel, 1989, 10:48-114.
31. Hermanson *Bioconjugate Techniques*, Academic Press, San Diego (1996) ISBN: 0123423368.
32. Anonymous (January 2002) Research Disclosure, 453077.
33. Anderson (1983) *Infect. Immun.* 39(1):233-8.
34. Anderson et al. (1985) *J. Clin. Invest.* 76(1):52-59.
35. EP 0372501A.
36. EP 0378881A.
37. EP 0427347A.
38. WO93/17712.
39. WO94/03208.
40. WO98/58668.
41. EP 0471177A.
42. WO91/01146.
43. Falugi et al. (2001) *Eur. J. Immunol.* 31:3816-24.
44. Baraldo et al. (2004) *Infect. Immun.* 72:4884-87.
45. EP 0594610A.
46. WO00/56360.
47. WO02/091998.
48. Kuo et al. (1995) Infect. Immun. 63:2706-13.
49. WO01/72337.
50. WO00/61761.
51. WO04/041157.
52. WO99/42130.
53. WO04/011027.
54. Lees et al. (1996) *Vaccine* 14:190-98.
55. WO95/08348.
56. U.S. Pat. No. 4,882,317.
57. U.S. Pat. No. 4,695,624.
58. Porro et al. (1985) Mol. Immunol. 22:907-19.
59. EP 0208375A.
60. WO00/10599.
61. Gever et al. *Med. Microbiol. Immunol.*, 165:171-288 (1979).
62. U.S. Pat. No. 4,057,685.
63. U.S. Pat. No. 4,673,574; U.S. Pat. No. 4,761,283; U.S. Pat. No. 4,808,700.
64. U.S. Pat. No. 4,459,286.
65. U.S. Pat. No. 4,965,338.
66. U.S. Pat. No. 4,663,160.
67. U.S. Pat. No. 4,761,283.
68. U.S. Pat. No. 4,356,170.
69. Lei et al. (2000) *Dev. Biol. (Basel)* 103:259-64.
70. WO00/38711; U.S. Pat. No. 6,146,902.
71. Wessels et al. (1998) *Infect. Immun.* 66:2186-92.
72. Lamb et al. (2000) *Dev. Biol. (Basel)* 103:251-58.
73. Lamb et al. (2000) *Journal of Chromatography A* 894: 311-18.

74. D'Ambra et al. (2000) Dev. Biol. (Basel) 103:241-42.
75. Gennaro (2000) *Remington: The Science and Practice of Pharmacy.* 20th edition, ISBN: 0683306472.
76. *Vaccine Design.* (1995) eds. Powell & Newman. ISBN: 030644867X. Plenum.
77. WO00/23105.
78. WO90/14837.
79. U.S. Pat. No. 5,057,540.
80. WO96/33739.
81. EP 0109942A.
82. WO96/11711.
83. WO00/07621.
84. Barr et al. (1998) *Advanced Drug Delivery Reviews* 32:247-71.
85. Sjolanderet et al. (1998) *Advanced Drug Delivery Reviews* 32:321-38.
86. Niikura et al. (2002) *Virology* 293:273-80.
87. Lenz et al. (2001) *J. Immunol.* 166:5346-55.
88. Pinto et al. (2003) *J. Infect. Dis.* 188:327-38.
89. Gerber et al. (2001) *Virology* 75:4752-60.
90. WO03/024480.
91. WO03/024481.
92. Gluck et al. (2002) *Vaccine* 20:B10-B16.
93. EP 0689454A.
94. Johnson et al. (1999) *Bioorg. Med. Chem. Lett.* 9:2273-78.
95. Evans et al. (2003) *Expert Rev. Vaccines* 2:219-29.
96. Meraldi et al. (2003) *Vaccine* 21:2485-91.
97. Pajak et al. (2003) *Vaccine* 21:836-42.
98. Kandimalla et al. (2003) *Nucleic Acids Research* 31:2393-2400.
99. WO02/26757.
100. WO99/62923.
101. Krieg (2003) *Nature Medicine* 9:831-35.
102. McCluskie et al. (2002) *FEMS Immunology and Medical Microbiology* 32:179-85.
103. WO98/40100.
104. U.S. Pat. No. 6,207,646.
105. U.S. Pat. No. 6,239,116.
106. U.S. Pat. No. 6,429,199.
107. Kandimalla et al. (2003) *Biochemical Society Transactions* 31 (part 3):654-58.
108. Blackwell et al. (2003) *J. Immunol.* 170:4061-68.
109. Krieg (2002) *Trends Immunol.* 23:64-65.
110. WO01/95935.
111. Kandimalla et al. (2003) *BBRC* 306:948-53.
112. Bhagat et al. (2003) *BBRC* 300:853-61.
113. WO03/035836.
114. WO95/17211.
115. WO98/42375.
116. Beignon et al. (2002) *Infect. Immun.* 70:3012-19.
117. Pizza et al. (2001) *Vaccine* 19:2534-41.
118. Pizza et al. (2000) *Int. J. Med. Microbiol.* 290:455-61.
119. Scharton-Kersten et al. (2000) *Infect. Immun.* 68:5306-13.
120. Ryan et al. (1999) *Infect Immun.* 67:6270-80.
121. Partidos et al. (1999) *Imnunol. Lett.* 67:209-16.
122. Peppoloni et al. (2003) *Expert Rev Vaccines* 2:285-293.
123. Pine et al. (2002) J. Control Release 85:263-70.
124. Domenighini et al. (1995) Mol. Microbiol. 15:1165-67.
125. WO99/40936.
126. WO99/44636.
127. Singh et al. (2001) *J. Cont. Release* 70:267-76.
128. WO99/27960.
129. U.S. Pat. No. 6,090,406.
130. U.S. Pat. No. 5,916,588.
131. EP 0626169A.
132. WO99/52549.
133. WO01/21207.
134. WO01/21152.
135. Andrianov et al. (1998) Biomaterials 19:109-15.
136. Payne et al. (1998) *Adv. Drug Delivery Review* 31:185-96.
137. Stanley (2002) Clin. Exp. Dermatol. 27:571-77.
138. Jones (2003) *Curr. Opin. Investig. Drugs* 4:214-18.
139. WO99/11241.
140. WO94/00153.
141. WO98/57659.
142. EP 0835318, EP 0735898 and EP 0761231 (patent applications).
143. Almeida & Alpar (1996) *J. Drug Targeting* 3:455-67.
144. Agarwal & Mishra (1999) Indian J. Exp. Biol. 37:6-16.
145. *Vaccines* (2004) eds. Plotkin & Orenstein. ISBN 0-7216-9688-0.
146. Bell (2000) *Pediatr. Infect. Dis. J.* 19:1187-88.
147. Iwarson (1995) *APMIS* 103:321-26.
148. Gerlich et al. (1990) *Vaccine* 8 Suppl:S63-68 & 79-80.
149. Gustafsson et al. (1996) *N. Engl. J. Med.* 334:349-55.
150. Rappuoli et al. (1991) *TIBTECH* 9:232-38.
151. Sutter et al. (2000) *Pediatr. Clin. North Am.* 47:287-308.
152. Zimmerman & Spann (1999) *Am. Fam. Physician* 59:113-18, 125-26.
153. McMichael (2000) *Vaccine* 19 Suppl 1:S101-107.
154. Schuchat (1999) Lancet 353(9146):51-56.
155. WO02/34771.
156. Dale (1999) *Infect. Dis. Clin. North Am.* 13:227-43, viii.
157. Ferretti et al. (2001) *PNAS USA* 98:4658-63.
158. Kuroda et al. (2001) *Lancet* 357(9264):1225-40, 1218-19.
159. Kanra et al. (1999) *The Turkish Journal of Pediatrics* 42:421-27.
160. Ravenscroft et al. (2000) *Dev. Biol. (Basel)* 103: 35-47.
161. WO97/00697.
162. WO02/00249.
163. WO96/37222; U.S. Pat. No. 6,333,036.
164. WO00/15255.
165. Svennerholm (1957) *Biochem. Biophys. ACTA* 24:604-11.
166. Rubens et al. (1987) *Proc. Natl. Acad. Sci.* 84:7208-12.
167. Group B Streptococcal infections; Edward, M. S., and C. J. Baker, *Infections diseases of the fetus and the newborn infants,* 2001, pp. 1091-1156.
168. Group B streptococcal disease in non pregnant adults; Farley, M. M., *Clinical Infections diseases,* 2001, 33:556-561.
169. Vaccination against Group B *Streptococcus*; Health Paul T. and Feldman Robert G. *Expert Rev. Vaccines* 4(2), 2005, 207-218.
170. Prevention of perinatal group B streptococcal disease: a public health perspective; Schumat A. Witmey C. G., Zangwill K. M., Centers for Disease Control and prevention, 1996, *MMWE* 45 (RR-7), 1-24.
171. Correlation of maternal antibody deficiency with susceptibility to neonatal group B Streptococcal infection; Baker C. J., Kasper D. L., *N. England J. Med.,* 1976, 294/753-6.
172. Regulation of cell component production by growth rate in the Group B *Streptococcus*; Robin A. Ross, Lawrence C. Madoff, and Lawrence C. Paoletti, *Journal of Bacteriology,* October 1999, Vol. 181, W17, pp. 5389-94.
173. Cell growth rate regulates expression of GBS type III capsular polysaccharide; Lawrence C. Paoletti, Robin A. Ross, and Kenneth D. Johnson, *Infection and Immunity,* pril 196, Vol. 64, No. 4, pp. 1220-1226.

174. Growth of Several Cariogenic strains of oral streptococci in a Chemically defined Medium; B. Terleckyj, N. P. Willett and G. D. Shockman, *Infection and Immunity*, April 1975, Vol. 11, No. 4, pp. 649-55.
175. The sialic acids; George W. Jourdian, Lawrence Dean, and Saul Roseman, *The Journal of Biological Chemistry*, Vol 246, No. 2, Issue of Jan. 25, 1971, pp. 480-85.
176. Quantitative estimation of sialic acids/a colorimetric resorcinol hydrochloric acid method; Lars Svennerholm, *Biochimica and Biophysoca Acta,* 1957, Vol. 24.
177. Yeast extract: production, properties and components; Rolf Sommer, Paper given at the 9th International Symposium of Yeasts, Sydney, August 1996.
178. Pigment production by *Streptococcus agalactiae* in Quasi-Defined Media; Fraile et al., *Applied and Environmental Microbiology*, Jan. 22, 2001, Vol. 67, No. 1, pp. 473-74.
179. Requirement for growth of *Streptococcus agalactiae* in a chemically defined medium; Norman P. Willet, Guy F. Morse and Sharon A. Carlisle, *Journal of Bacteriology*, October 1967, Vol 94(no. 4), pp. 1247-48.
180. Tettelin et al. (2002) *Proc. Natl. Acad. Sci. USA,* 10.1 073/pnas. 182380799.
181. International patent application WO02/34771.
182. Terpe et al., "Overview of tag protein fusions: from molecular and biochemical fundamentals to commercial systems", Appl Microbiol Biotechnol (2003) 60:523-533.
183. WO99/27961.
184. WO02/074244.
185. WO02/064162.
186. WO03/028760.
187. Gennaro (2000) *Remington: The Science and Practice of Pharmacy.* 20th ed., ISBN: 0683306472.
188. *Vaccine design: the subunit and adjuvant approach* (1995) Powell & Newman. ISBN 0-306-44867-X.
189. WO00/23105.
190. WO00/07621.
191. Barr, et al., "ISCOMs and other saponin based adjuvants", Advanced Drug Delivery Reviews (1998) 32:247-271. See also Sjolander, et al., "Uptake and adjuvant activity of orally delivered saponin and ISCOM vaccines", Advanced Drug Delivery Reviews (1998) 32:321-338.
192. Niikura et al., "Chimeric Recombinant Hepatitis E Virus-Like Particles as an Oral Vaccine Vehicle Presenting Foreign Epitopes", Virology (2002) 293:273-280.
193. Lenz et al., "Papillomarivurs-Like Particles Induce Acute Activation of Dendritic Cells", Journal of Immunology (2001) 5246-5355.
194. Pinto, et al., "Cellular Immune Responses to Human Papillomavirus (HPV)-16 L1 Healthy Volunteers Immunized with Recombinant HPV-16 L1 Virus Like Particles", Journal of Infectious Diseases (2003) 188:327-338.
195. Gerber et al., "Human Papillomavirus Virus-Like Particles Are Efficient Oral Immunogens when Coadministered with *Escherichia coli* Heat-Labile Enterotoxin Mutant R192G or CpG", Journal of Virology (2001) 75(10):4752-4760.
196. Gluck et al., "New Technology Platforms in the Development of Vaccines for the Future", Vaccine (2002) 20:B10-B16.
197. Johnson et al. (1999) *Bioorg Med Chem Lett* 9:2273-2278
198. Meraldi et al., "OM-174, a New Adjuvant with a Potential for Human Use, Induces a Protective Response with Administered with the Synthetic C-Terminal Fragment 242-310 from the circumsporozoite protein of *Plasmodium berghei*", Vaccine (2003) 21:2485-2491.
199. Pajak, et al., "The Adjuvant OM-174 induces both the migration and maturation of murine dendritic cells in vivo", Vaccine (2003) 21:836-842.
200. Kandimalla, et al., "Divergent synthetic nucleotide motif recognition pattern: design and development of potent immunomodulatory oligodeoxyribonucleotide agents with distinct cytokine induction profiles", Nucleic Acids Research (2003) 31(9): 239 3-2400.
201. Krieg, "CpG motifs: the active ingredient in bacterial extracts?", Nature Medicine (2003) 9(7): 831-835.
202. McCluskie, et al., "Parenteral and mucosal prime-boost immunization strategies in mice with hepatitis B surface antigen and CpG DNA", FEMS Immunology and Medical Microbiology (2002) 32:179 185.
203. Kandimalla, et al., "Toll-like receptor 9: modulation of recognition and cytokine induction by novel synthetic CpG DNAs", Biochemical Society Transactions (2003) 31 (part 3): 654-658.
204. Blackwell, et al., "CpG-A-Induced Monocyte IFN-gamma-Inducible Protein-10 Production is Regulated by Plasmacytoid Dendritic Cell Derived IFN-alpha", J. Immunol. (2003) 170(8):4061 4068.
205. Krieg, "From A to Z on CpG", TRENDS in Immunology (2002) 23(2): 64-65.
206. Kandimalla, et al., "Secondary structures in CpG oligonucleotides affect immunostimulatory activity", BBRC (2003) 306:948-953.
207. Kandimalla, et al., "Toll-like receptor 9: modulation of recognition and cytokine induction by novel synthetic GpG DNAs", Biochemical Society Transactions (2003) 31(part 3):664-658.
208. Bhagat et al., "CpG penta and hexadeoxyribonucleotides as potent immunomodulatory agents" BBRC (2003) 300: 853-861.
209. Singh et al. (2001) *J. Cont. Rele.* 70:267-276.
210. WO99/27960.
211. WO99/52549.
212. WO01/21207.
213. WO01/21152.
214. Andrianov et al., "Preparation of hydrogel microspheres by coacervation of aqueous polyphophazene solutions", Biomaterials (1998) 19(1-3):109-115.
215. Payne et al., "Protein Release from Polyphosphazene Matrices", Adv. Drug. Delivery Review (1998) 31(3):185-196.
216. Stanley, "Imiqulmod and the imidazoquinolones: mechanism of action and therapeutic potential" Clin Exp Dermatol (2002) 27(7):571-577.
217. Jones, "Resiquimod 3M", Curr Opin Investig Drugs (2003) 4(2):214-218.
218. WO99/11241.
219. WO98/57659.
220. European patent applications 0835318, 0735898 and 0761231.
221. Ramsay et al. (2001) *Lancet* 357(9251): 195-196.
222. Lindberg (1999) *Vaccine* 17 Suppl 2:S28-36.
223. Buttery & Moxon (2000) *J R Coll Physicians Lond* 34:163-168.
224. Ahmad & Chapnick (1999) *Infect Dis Clin North Am* 13: 113 133, vii.
225. Goldblatt (1998) J. Med. Microbiol. 47:563-567.
226. European patent 0 477 508.
227. U.S. Pat. No. 5,306,492.
228. International patent application WO98/42721.
229. *Conjugate Vaccines* (eds. Cruse et al.) ISBN 3805549326, particularly vol. 10:48-114.

230. Hermanson (1996) Bioconjugate Techniques ISBN: 0123423368 or 012342335X.
231. *Research Disclosure*, 453077 (January 2002)
232. EP-A-0372501
233. EP-A-0378881
234. EP-A-0427347
235. WO93/17712
236. WO94/03208
237. WO98/58668
238. EP-A-0471177
239. WO00/56360
240. WO91/01146
241. WO00/61761
242. WO01/72337
243. Robinson & Torres (1997) *Seminars in Immunology* 9:271-283.
244. Donnelly et al. (1997) *Annu Rev Immunol* 15:617-648.
245. Scott-Taylor & Dalgleish (2000) *Expert Opin Investig Drugs* 9:471-480.
246. Apostolopoulos & Plebanski (2000) *Curr Opin Mol. Ther.* 2:441-447.
247. Ilan (1999) *Curr Opin Mol. Ther.* 1:116-120.
248. Dubensky et al. (2000) *Mol. Med.* 6:723-732.
249. Robinson & Pertmer (2000) *Adv Virus Res* 55: 1-74.
250. Donnelly et al. (2000) *Am J Respir Crit. Care Med* 162(4 Pt 2):S190-193.
251. Davis (1999) *Mt. Sinai J. Med.* 66:84-90.
252. *Current Protocols in Molecular Biology* (F. M. Ausubel et al., eds., 1987) Supplement 30.
253. Smith & Waterman (1981) *Rev. Appl. Math.* 2: 482-489.
254. U.S. Pat. No. 6,372,223.
255. WO00/15251.
256. WO01/22992.
257. Hehme et al. (2004) *Virus Res.* 103(1-2):163-71.
258. U.S. Pat. No. 6,355,271.
259. WO00/23105.
260. *Vaccine Design: The Subunit and Adjuvant Approach* (eds. Powell & Newman) Plenum Press 1995 (ISBN 0-306-44867-X).
261. U.S. Pat. No. 5,057,540.
262. WO05/02620.
263. WO96/33739.
264. EP-A-0109942.
265. U.S. Pat. No. 4,578,269.
266. WO96/11711.
267. U.S. Pat. No. 6,352,697.
268. WO00/07621 and U.S. Pat. No. 6,506,386.
269. WO04/04762.
270. Barr et al. (1998) *Advanced Drug Delivery Reviews* 32:247-271.
271. Sjolanderet et al (1998) *Advanced Drug Delivery Reviews* 32:321-338.
272. Pizza et al. (2000) *Int J Med Microbiol* 290:455-461.
273. WO95/17211.
274. WO98/42375.
275. Singh et al. (2001) *J Cont Release* 70:267-276.
276. WO99/27960.
277. U.S. Pat. No. 6,090,406.
278. U.S. Pat. No. 5,916,588.
279. EP-A-0626169.
280. WO99/52549.
281. WO01/21207.
282. WO01/21152.
283. WO02/72012.
284. Signorelli and Hadden (2003) *Int Immunopharmacol* 3(8):1177-86.
285. WO04/64715.
286. Cooper (1995) *Pharm Biotechnol* 6:559-80.
287. *Vaccine Adjuvants: Preparation Methods and Research Protocols* (Volume 42 of *Methods in Molecular Methods* series). ISBN: 1-59259-083-7. Ed. O'Hagan.
288. WO05/89837.
289. U.S. Pat. No. 6,692,468.
290. WO00/07647.
291. WO99/17820.
292. U.S. Pat. No. 5,971,953.
293. U.S. Pat. No. 4,060,082.
294. EP-A-0520618.
295. WO98/01174.
296. WO90/14837.
297. Podda and Del Giudice (2003) *Expert Rev Vaccines* 2:197-203.
298. Podda (2001) *Vacccine* 19:2673-2680.
299. Allison and Byars (1992) *Res Immunol* 143:519-25.
300. Hariharan et al. (1995) *Cancer Res* 55:3486-9.
301. WO95/11700.
302. U.S. Pat. No. 6,080,725.
303. WO05/097181.
304. Han et al. (2005) *Impact of Vitamin E on Immune Function and Infectious Diseases in the Aged at Nutrition, Immune functions and Health* EuroConference, Paris, 9-10 Jun. 2005.
305. U.S. Pat. No. 6,630,161.
306. WO02/097072.
307. Hayden et al. (1998) *J Clin Invest* 101(3):643-9.
308. Tassignon et al. (2005) *J Immunol Meth* 305:188-98.
309. Myers et al. (1990) pages 145-156 of Cellular and molecular aspects of endotoxin reactions.
310. Ulrich (2000) Chapter 16 (pages 273-282) of reference 108.
311. Johnson et al. (1999) *J Med Chem* 42:4640-9.
312. Baldrick et al. (2002) *Regulatory Toxicol Pharmacol* 35:398-413.
313. U.S. Pat. No. 4,680,338.
314. U.S. Pat. No. 4,988,815.
315. WO92/15582.
316. Stanley (2002) *Clin Exp Dermatol* 27:571-577.
317. Wu et al. (2004) *Antiviral Res.* 64(2):79-83.
318. Vasilakos et al. (2000) *Cell Immunol.* 204(1):64-74.
319. U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293.
320. Jones (2003) *Curr Opin Investig Drugs* 4:214-218.
321. WO2004/060308.
322. WO2004/064759.
323. U.S. Pat. No. 6,924,271.
324. U.S. Patent App. No. 2005/0070556.
325. U.S. Pat. No. 5,658,731.
326. U.S. Pat. No. 5,011,828.
327. WO2004/87153.
328. U.S. Pat. No. 6,605,617.
329. WO02/18383.
330. WO2004/018455.
331. WO03/082272.
332. PCT/US2005/022769.
333. Johnson et al. (1999) *Bioorg Med Chem Lett* 9:2273-2278.
334. Evans et al. (2003) *Expert Rev Vaccines* 2:219-229.
335. Andrianov et al. (1998) *Biomaterials* 19:109-115.

336. Payne et al. (1998) *Adv Drug Delivery Review* 31:185-196.
337. Thompson et al. (2003) *Methods in Molecular Medicine* 94:255-266.
338. Kandimalla et al. (2003) *Nucleic Acids Research* 31:2393-2400.
339. WO02/26757.
340. WO99/62923.
341. Krieg (2003) *Nature Medicine* 9:831-835.
342. McCluskie et al. (2002) *FEMS Immunology and Medical Microbiology* 32:179-185.
343. WO98/40100.
344. U.S. Pat. No. 6,207,646.
345. U.S. Pat. No. 6,239,116.
346. U.S. Pat. No. 6,429,199.
347. Kandimalla et al. (2003) *Biochemical Society Transactions* 31 (part 3):654-658.
348. Blackwell et al. (2003) *J Immunol* 170:4061-4068.
349. Krieg (2002) *Trends Immunol* 23:64-65.
350. WO01/95935.
351. Kandimalla et al. (2003) *BBRC* 306:948-953.
352. Bhagat et al. (2003) *BBRC* 300:853-861.
353. WO03/035836.
354. WO01/22972.
355. Thompson et al. (2005) *J Leukoc Biol* 78: 'The low-toxicity versions of LPS, MPL® adjuvant and RC529, are efficient adjuvants for CD4+ T cells'.
356. UK patent application GB A 2220211.
357. WO 94/21292.
358. WO94/00153.
359. WO95/17210.
360. WO96/26741.
361. WO93/19780.
362. WO03/011223.
363. Meraldi et al. (2003) *Vaccine* 21:2485-2491.
364. Pajak et al. (2003) *Vaccine* 21:836-842.
365. U.S. Pat. No. 6,586,409.
366. Wong et al. (2003) *J Clin Pharmacol* 43(7):735-42.
367. U.S. Pat. App. No. 2005/0215517.

We claim:

1. A method for purifying a capsular polysaccharide from *Streptococcus agalactiae* comprising a step of filtration using an adherent filter, wherein the adherent filter binds contaminants that may be present in the capsular polysaccharide.

2. The method of claim 1, wherein the method does not include a step of cationic detergent treatment to precipitate the capsular polysaccharide followed by a step of re-solubilization of the capsular polysaccharide.

3. The method of claim 1, wherein the adherent filter is a protein adherent filter.

4. The method of claim 1, wherein the adherent filter is a carbon filter.

5. The method of claim 1, wherein the step of filtration using the adherent filter is preceded by:
   (i) alcoholic precipitation of contaminating proteins and/or nucleic acids; and
   (ii) diafiltration.

6. The method of claim 1, wherein the step of filtration using the adherent filter is followed by:
   (iv) re-N-acetylation;
   (v) diafiltration.

7. A method for production of a purified capsular polysaccharide comprising:
   (a) providing a crude isolate containing a capsular polysaccharide;
   (b) removing an alcohol precipitate formed by contacting the crude isolate with an alcohol solution;
   (c) filtering to remove smaller molecular weight compounds while retaining the capsular polysaccharide; and
   (d) removing protein contaminants with a protein adherent filter to produce the purified capsular polysaccharide.

8. The method of claim 7, further comprising step (e) re-N-acetylating the purified capsular polysaccharide.

9. The method of claim 8, further comprising step (f) precipitating the purified capsular polysaccharide.

10. The method of claim 9, further comprising step (g) formulating a vaccine with the capsular polysaccharide as a component.

11. The method of claim 7, wherein step (b) comprises addition of an alcohol solution to a concentration sufficient to precipitate nucleic acid contaminants but not the capsular polysaccharide.

12. The method of claim 11, wherein said alcohol solution comprises ethanol.

13. The method of claim 12, wherein said alcohol solution is added to a concentration of between about 10% and about 50% ethanol.

14. The method of claim 13, wherein said alcohol solution is added to a concentration of about 30% ethanol.

15. The method of claim 11, wherein said alcohol solution further comprises $CaCl_2$.

16. The method of claim 7, wherein the protein adherent filter is an activated carbon filter.

17. The method of claim 7, wherein the capsular polysaccharide is a *Streptococcus agalactiae* capsular polysaccharide.

* * * * *

UNITED STATES PATENT AND TRADEMARK OFFICE
CERTIFICATE OF CORRECTION

PATENT NO.       : 8,445,239 B2
APPLICATION NO. : 12/747914
DATED            : May 21, 2013
INVENTOR(S)      : Costantino et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 315 days.

Signed and Sealed this
Eighth Day of September, 2015

Michelle K. Lee
*Director of the United States Patent and Trademark Office*